(12) United States Patent  (10) Patent No.: US 9,138,462 B2
Rau et al.  (45) Date of Patent: Sep. 22, 2015

(54) PRODRUGS COMPRISING AN INSULIN LINKER CONJUGATE

(75) Inventors: Harald Rau, Heidelberg (DE); Felix Cleemann, Heidelberg (DE); Ulrich Hersel, Heidelberg (DE); Silvia Kaden-Vagt, Heidelberg (DE); Torben Lessman, Mannheim (DE); Thomas Wegge, Heidelberg (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/387,940

(22) PCT Filed: Jul. 30, 2010

(86) PCT No.: PCT/EP2010/061159
§ 371 (c)(1),
(2), (4) Date: Mar. 30, 2012

(87) PCT Pub. No.: WO2011/012718
PCT Pub. Date: Feb. 3, 2011

(65) Prior Publication Data
US 2012/0184489 A1 Jul. 19, 2012

(30) Foreign Application Priority Data

Jul. 31, 2009 (EP) .................................... 09167027
Oct. 29, 2009 (EP) .................................... 09174525
Dec. 15, 2009 (EP) .................................... 09179336
Dec. 18, 2009 (EP) .................................... 09179818

(51) Int. Cl.
*A61K 38/28* (2006.01)
*A61P 3/10* (2006.01)
*C07K 14/62* (2006.01)
*A61K 47/48* (2006.01)

(52) U.S. Cl.
CPC ........... *A61K 38/28* (2013.01); *A61K 47/48215* (2013.01); *C07K 14/62* (2013.01); *Y10T 428/13* (2015.01); *Y10T 428/2982* (2015.01)

(58) Field of Classification Search
CPC . A61K 38/28; A61K 47/48215; C07K 14/62; Y10T 428/2982; Y10T 428/13
See application file for complete search history.

(56) References Cited

U.S. PATENT DOCUMENTS

| 5,424,286 | A  | 6/1995  | Eng |
| 5,514,379 | A  | 5/1996  | Weissleder et al. |
| 5,634,943 | A  | 6/1997  | Villain et al. |
| 6,271,345 | B1 | 8/2001  | Waldmann et al. |
| 6,506,724 | B1 | 1/2003  | Hiles et al. |
| 6,537,569 | B2 | 3/2003  | Cruise |
| 6,602,952 | B1 | 8/2003  | Bentley et al. |
| 7,157,555 | B1 | 1/2007  | Beeley et al. |
| 7,393,953 | B2 | 7/2008  | Zhao et al. |
| 7,585,831 | B2 | 9/2009  | Lang |
| 7,585,837 | B2 | 9/2009  | Shechter et al. |
| 7,879,588 | B2 | 2/2011  | Vetter et al. |
| 7,968,085 | B2 | 6/2011  | Hersel et al. |
| 8,377,917 | B2 | 2/2013  | Hersel et al. |
| 2001/0048947 | A1 | 12/2001 | Rowe et al. |
| 2003/0023023 | A1 | 1/2003  | Harris et al. |
| 2003/0078314 | A1 | 4/2003  | Johnson et al. |
| 2003/0083389 | A1 | 5/2003  | Kao et al. |
| 2003/0166833 | A1 | 9/2003  | Lutolf et al. |
| 2003/0220245 | A1 | 11/2003 | Hubbell et al. |
| 2004/0023842 | A1 | 2/2004  | Pathak et al. |
| 2006/0002890 | A1 | 1/2006  | Hersel et al. |
| 2006/0115865 | A1 | 6/2006  | Ouyang et al. |
| 2007/0207210 | A1 | 9/2007  | Brown et al. |
| 2007/0275030 | A1 | 11/2007 | Muratoglu et al. |
| 2008/0187568 | A1 | 8/2008  | Sawhney |
| 2008/0220047 | A1 | 9/2008  | Sawhney et al. |
| 2008/0241102 | A1 | 10/2008 | Hersel et al. |

(Continued)

FOREIGN PATENT DOCUMENTS

DE 10 2008 003 566 A1 7/2009
DE 10 2008 003 568 A1 7/2009

(Continued)

OTHER PUBLICATIONS

Muller, Prodrug Approaches for Enhancing the Bioavailability of Drugs eith Low Solubility, Chemistry & Biodiversity, 2009, 6, pp. 2071-2083.*
Beaumont, et, al, Design of Ester Prodrugs to Enhance Oral Absorption of Poorly Permeable Compounds: Challenges to the Discovery Scientist, Current Drug Metabolism, 2003, 4, 461-485.*
Hyo-Kyung Han, Targeted Prodrug Design to Optimize Drug Delivery, AAPS Pharmsci 2000; 2 (1) article 6 pp. 1-11.*
Yashveer Singh et al, Recent Trends in Targeted Anticancer Prodrug and Conjugate Design, Curr Med Chem. 2008; 15(18): 1802-1826.*
Testa B., Prodrug Research: Futile or Fertile?, Biochem. Pharm., 2004, 68, pp. 2097-2106.*

(Continued)

*Primary Examiner* — Julie Ha
*Assistant Examiner* — Li Ni Komatsu
(74) *Attorney, Agent, or Firm* — Morrison & Foerster LLP

(57) ABSTRACT

The present invention relates to a prodrug or a pharmaceutically acceptable salt thereof comprising an insulin linker conjugate D-L$^1$, wherein D is insulin; and -L$^1$ is:

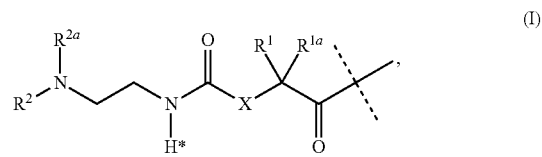

(I)

wherein the dashed line indicates the attachment to one of the amino groups of the insulin by forming an amide bond. The invention further relates to pharmaceutical compositions comprising said prodrugs as well as their use as a medicament for treating or preventing diseases or disorders which can be treated by insulin.

27 Claims, 10 Drawing Sheets

(56) References Cited

U.S. PATENT DOCUMENTS

| | | |
|---|---|---|
| 2008/0293827 A1 | 11/2008 | Lee et al. |
| 2009/0030102 A1 | 1/2009 | Nelles et al. |
| 2010/0291021 A1 | 11/2010 | Vetter et al. |
| 2011/0009315 A1 | 1/2011 | Hersel et al. |
| 2011/0053848 A1 | 3/2011 | Cleemann et al. |
| 2011/0112021 A1 | 5/2011 | Rau et al. |
| 2012/0058084 A1 | 3/2012 | Rau et al. |
| 2012/0156259 A1 | 6/2012 | Rau et al. |
| 2012/0183616 A1 | 7/2012 | Sprogoe et al. |
| 2012/0184489 A1 | 7/2012 | Rau et al. |
| 2012/0253071 A1 | 10/2012 | Rau et al. |
| 2013/0189328 A1 | 7/2013 | Rau et al. |

FOREIGN PATENT DOCUMENTS

| | | |
|---|---|---|
| EP | 0 214 826 A2 | 3/1987 |
| EP | 0 368 187 A2 | 5/1990 |
| EP | 0 375 437 A2 | 6/1990 |
| EP | 0 678 522 A1 | 10/1995 |
| EP | 0 885 961 A1 | 12/1998 |
| EP | 1 670 265 A1 | 6/2006 |
| EP | 2017288 A1 | 1/2009 |
| EP | 2 596 805 A1 | 5/2013 |
| JP | 2005239736 A2 | 5/2005 |
| JP | 2005-239736 A | 9/2005 |
| WO | 89/10937 A1 | 11/1989 |
| WO | WO 92/00321 A1 | 1/1992 |
| WO | WO9317669 A1 | 9/1993 |
| WO | WO 97/04796 A1 | 2/1997 |
| WO | WO 99/14259 A1 | 3/1999 |
| WO | WO 99/25354 A2 | 5/1999 |
| WO | WO 99/25727 A2 | 5/1999 |
| WO | WO 99/25728 A1 | 5/1999 |
| WO | 99/30727 A1 | 6/1999 |
| WO | WO 99/34833 A1 | 7/1999 |
| WO | WO 99/40788 A1 | 8/1999 |
| WO | WO0021572 A2 | 4/2000 |
| WO | WO0044808 A1 | 8/2000 |
| WO | WO0069900 A2 | 11/2000 |
| WO | WO0147562 A2 | 7/2001 |
| WO | 01/85180 A1 | 11/2001 |
| WO | WO0217880 A2 | 3/2002 |
| WO | WO02083180 A1 | 10/2002 |
| WO | 02/094200 A2 | 11/2002 |
| WO | WO02089789 A1 | 11/2002 |
| WO | WO02094200 A2 | 11/2002 |
| WO | 03/035244 A1 | 5/2003 |
| WO | WO03035244 A1 | 5/2003 |
| WO | WO03049677 A2 | 6/2003 |
| WO | 03/098142 A1 | 11/2003 |
| WO | WO03101425 A2 | 12/2003 |
| WO | WO03104426 A2 | 12/2003 |
| WO | WO2004043493 A1 | 5/2004 |
| WO | WO2004089280 A2 | 10/2004 |
| WO | WO2004108070 A2 | 12/2004 |
| WO | WO2005034909 A2 | 4/2005 |
| WO | WO2005099768 A2 | 10/2005 |
| WO | WO2005099769 A2 | 10/2005 |
| WO | WO2006003014 A2 | 1/2006 |
| WO | 2006/038462 A1 | 4/2006 |
| WO | WO2006038462 A1 | 4/2006 |
| WO | WO2006047451 A2 | 5/2006 |
| WO | WO2006073396 A1 | 7/2006 |
| WO | WO 2006/115865 A1 | 11/2006 |
| WO | WO2006136586 A2 | 12/2006 |
| WO | WO2007053946 A1 | 5/2007 |
| WO | WO2007082088 A2 | 7/2007 |
| WO | WO2007140312 A2 | 12/2007 |
| WO | WO2008/015099 A2 | 2/2008 |
| WO | WO2008015099 A2 | 2/2008 |
| WO | WO2008034122 A2 | 3/2008 |
| WO | WO2008116913 A2 | 10/2008 |
| WO | WO2008125655 A1 | 10/2008 |
| WO | WO2008/148839 A2 | 12/2008 |
| WO | WO2008148839 A2 | 12/2008 |
| WO | WO2009/010428 A1 | 1/2009 |
| WO | WO2009010428 A1 | 1/2009 |
| WO | WO 2009/095479 A2 * | 8/2009 ............ A61K 47/48 |
| WO | WO2009095479 | 8/2009 |
| WO | WO2009102952 A2 | 8/2009 |
| WO | WO2009134336 A1 | 11/2009 |
| WO | WO2011012715 A1 | 2/2011 |
| WO | WO2011012718 A1 | 2/2011 |
| WO | WO2011012719 A1 | 2/2011 |
| WO | WO2011051406 A1 | 5/2011 |
| WO | WO2012035139 A1 | 3/2012 |

OTHER PUBLICATIONS

Ettmayer, P. et al, Lessons Learned from Marketed and Investigational Prodrugs,J. Med. Chem., 2004, 47 (10), pp. 2393-2404.*

Definition of derivatives and analogues, from http://cancerweb.ncl.ac.uk/cgi-bin/omd?query=derivative and http://cancerweh.ncl.ac.uk/cgi-hin/omd?analogue, pp. 1-5, accessed Jul. 7, 2005.*

Definition of mimetics, from http://www.thefreedictionary.com/p/mimetic, pp. 1-2, accessed Oct. 11, 2013.*

Definition of moiety, from http://dictionary.reference.com/browse/moieties, pp. 1-3, accessed Aug. 26, 2010.*

Definition of the like, from http://www.thefreedictionary.com/p/the%20like, p. 1, accessed Oct. 15, 2013.*

Diabetes Mellitus, from Merck Manual, pp. 1-22, accessed Apr. 2, 2013.*

Human insulin amino acid sequence, from http://dailymed.nlm.nih.gov/dailymed/fda/fdaDrugXsl.cfm?id=7043, p. 1, accessed Oct. 16, 2013.*

Wathier et al, Dendritic Macromers as in Situ Polymerizing Biomaterials for Securing Cataract Incisions, J. Am. Chem. Soc. 2004, 126, pp. 12744-12745.*

Izutsu, Stabilization of Therapeutic Proteins by Chemica I and Physica I Methods, from Therapeutic proteins, methods and protocols, Edited by C. Mark Smales and David C. James, Humana press, 2005, pp. 1-8.*

Crosslinking Technical Handbook, from Thermo Scientific, published on Apr. 2009, pp. 1-48.*

International Preliminary Report on Patentability dated Jan. 31, 2012 issued in PCT/EP2010/061159.

Antczak et al., "A New Acivicin Prodrug Designed for Tumor-Targeted Delivery", "Bioorganic & Medicinal Chemistry", 2001, pp. 2843-2848, vol. 9, Publisher: Elsevier Science Ltd.

Attwood et al., "Influence of gamma irradiation on the rheological properties of gels of the poloxamine, Synperonic T908", International Journal of Pharmaceutics, vol. 70, No. 1-2, 1991, pp. 147-152.

"Beaumont et al., Design of Ester Prodrugs to Enhance Oral Absorption of Poorly Permeable Compounds: Challenges to theDiscovery Scientist, Current Drug Metabolism, 2003, 4, 461-485."

Bernkop-Schnurch, 1997, Journal of Controlled release 47 (1997) 113-121.

Bhatt et al., "Synthesis and in Vivo Antitumor Activity of Poly(L-glutamic acid) Conjugates of 20(S)- Camptothecin", "J. Med. Chem.", 2003, p. 190-193, vol. 46.

Boas et al., "Dendrimers in drug research", Chem. Soc. Rev., 2004, pp. 43-63, vol. 33.

Cadee et al., "Release of recombinant human interleukin-2 from dextran-based hydrogels", J. Controlled Release, 2002, 1-13, vol. 78.

Caliceti et al., "Pharmacokinetic and biodistribution properties of poly( ethylene glycol)- protein conjugates", Advanced Drug Delivery, 2003, 1261-1277, vol. 55.

Cavallaro et al., "Polymeric Prodrug for Release of an Antitumoral Agent by Specific Enzymes", Bioconjugate Chemistry, 2001, 143-151, vol. 12.

Cheng et al., "Synthesis of Linear, Beta-Cyclodextrin-Based Polymers and Their Camptothecin Conjugates", Bioconjugate Chemistry, 2003, 1007-1017, vol. 14.

Choi et al, "Control of Blood Glucose by Novel GLP-1 Delivery Using Biodegradable Triblock Copolymer of PLGA-PEG-PLGA in Type 2 Diabetic Rats," Pharmaceutical Research, vol. 21, No. 5, pp. 827-831 (2004).

(56) References Cited

OTHER PUBLICATIONS

Christensen et al, Lixisenatide, a novel GLP-1 receptor agonist for the treatment of type 2 diabetes mellitus, I Drugs, 2009, 12, pp. 503-513.
Defronzo et al., "Effects of Exenatide (Exendin-4) on Glycemic Control and Weight Over 30 Weeks in Metformin-Treated Patients With Type 2 Diabetes", Diabetes Care, May 2005, pp. 1092-1100, vol. 28, No. 5.
Definition of derivatives and analogues, from http://cancerweb.ncl.ac.uk!cgi-bin/omd?query=derivative and http://cancerweh.ncl.ac.uk!cgi-hin/omd?analogue, pp. 1-5, accessed Jul. 7, 2005.
Definition of the like, from http://www.thefreedictionary.com/p/the%20like, p. 1, accessed Jan. 15, 2013.
Domb et al., "Chemical interactions between drugs containing reactive amines with hydrolyzable insoluble biopolymers in aqueous solutions," Pharm. Res. 11(6) (1994) 865-868.
Duncan et al., "Polymer-drug conjugates, PDEPT and PELT: basic principles for design and transfer from the laboratory to clinic", J. Control. Release, 2001, 74:135-146.
Dupre et al., "Exendin-4 Normalized Postcibal Glycemic Excursions in Type I Diabetes", J Clin. Endocrinol. Metab., 2004, pp. 3469-3473, vol. 89, No. 7, US.
Edwards et al., "Exendin-4 reduces fasting and postprandial glucose and decreases energy intake in healthy volunteers", Am. J. Physiol. Endocrinol. Metab. 2001, pp. 155-161, vol. 281, US.
Ellman et al., "A new and rapid colorimetric determinationof acetylcholinesterase activity," Biochem. Pharmacol., 1961, 7, 88-95.
Eng et al., "Isolation and characterization of exendin-4, an exendin-3 analogue, from heloderma suspectum venom," J. Bio. Chem., 1992, 7402-7405, vol. 267, No. 11.
English et al., "Orally effective acid prodrugs of the β-lactamase inhibitor sulbactam," J. Med. Chem., 1990, 344-347, vol. 33.
Esfand et al., "Poly(amidoamine) (PAMAM) dendrimers: from biomimicry to drug delivery and biomedical applications", Drug Discov. Today, 2001, pp. 427-436, vol. 6, No. 8
Franssen et al., "Controlled release of a model protein from enzymatically degrading dextran microspheres," J. Control. Release, 59(2):219-228, 1999.
Garman et al., "The Preparation and Properties of Novel Reversible Polymer-Protein Conjugates", FEBS Lett., 1987, 223(2):361-365.
Goke et al., "Exendin-4 Is a High Potency Agonist and Truncated Exendin-(9-39)-amide an Antagonist at the Glucagon-like Peptide 1-(7-36)-amide Receptor ofInsulin-secreting B-Cells", J. of Biolo. Chern., Sep. 15, 1993, pp. 19650-19655, vol. 268, No. 26, US.
Gomes et al.,"Cyclization-activated prodrugs." Molecules (Basel, Switzerland) 2007, vol. 12, No. 11, 2007, pp. 2484-2506.
Grayson et al., "Convergent Dendrons and Dendrimers: from Synthesis to Applications", Chern. Rev., 2001, pp. 3819-3867, vol. 101, Berkeley, CA, US.
Greenwald et al., "A New Aliphatic Amino Prodrug System for the Delivery of Small Molecules and Proteins Utilizing Novel PEG Derivatives", "J. Med. Chem.", 2004, pp. 726-734, vol. 47, Publisher: American Chemical Society.
Greenwald et al., "Drug Delivery Systems Based on Trimethyl Lock Lactonization Poly( ethylene glycol) Prodrugs of Amino-Containing Compounds", "J. Med. Chem.", 2000, pp. 475-487, vol. 43, Publisher: American Chemical Society.
Greenwald et al., "Drug Delivery Systems Employing 1,4- or 1,6-Eiimination: Poly( ethylene glycol) Prodrugs of Amine-Containing Compounds", "J. Med. Chem.", 1999, pp. 3657-3667, vol. 42, Publisher: American Chemical Society.
Greig, et al: New therapeutic strategies and drug candidates for neurodegenerative diseases: p53 and TNF-alpha inhibitors, and GLP-1 receptor agonists. Annals of the New York Academy of Sciences, vol. 1035, 2004, pp. 290-315.
Gude et al., "An accurate method for the quantitation of Fmoc-derivatized solid phase," (2002) Letters in Peptide Science 9(4): 203-206.

Gutniak et al., "Antidiabetogenic effect of glucagon-like peptide-! (7-36)amide in normal subjects and patients with diabetes mellitus", NE J. of Med., May 14, 1992, pp. 1316-1322, vol. 326, No. 20.
Han, Targeted Prodrug Design to Optimize Drug Delivery, AAPS PharmSci 2000, 2, article 6, pp. 1 to 11.
Hayashi et al., "Development of oligoarginine-drug conjugates linked to new peptidic self-cleavable spacers toward effective intestinal absorption" Bioorganic and Medicinal Chemistry Letters Sep. 15, 2007 GB, vol. 17, No. 1a, Sep. 15, 2007, pp. 5129-5132.
Hennink et al., "Novel crosslinking methods to design hydrogels", "Advanced Drug Delivery Reviews", 2002, pp. 13-36, vol. 54, Publisher: Elsevier Science B.V.
Herman (Ed.), "Biodegradable Polymers, Medical Applications", Encyclopedia of Polymer Science and Technology, 2004, pp. 263-285, vol. 5, John Wiley & Sons, Inc., Hoboken, NJ.
Hinds et al., Effects of PEG conjugation of insulin properties, Advanced Drug Delivery Reviews vol. 54, 2002, 505-530.
Hinds et al., Journal of Controlled Release, 2005 (104), 447-460.
Hoffman, "Hydrogels for biomedical applications", "Advanced Drug Delivery Reviews", 2002, pp. 312, vol. 43, Publisher: Elsevier Science B.V.
Huynh et al., "Controlled release of insulin from pH/temperature-sensitive injectable pentablock copolymer hydrogel", Journal of Controlled Release, vol. 137, No. 1, 2009 pp. 20-24.
Huynh et al., "Functionalized injectable hydrogels for controlled insulin delivery" Biomaterials (Jun. 2008) pp. 2527-2534, vol. 29, No. 16.
Young et al., "Glucose-Lowering and Insulin-Sensitizing Actions ofExendin-4: Studies in Obese Diabetic (ob/ob, db/db) Mice, Diabetic Fatty Zucker Rats, and Diabetic Rhesus Monkeys (*Macaca mulatta*)", Diabetes, May 1999, pp. 1026-1034, vol. 48.
Zhao et al., "Novel degradable poly(ethylene glycol) hydrogels for controlled release of protein," J. Pharm. Sciences, 1998, 1450-1458, vol. 87, No. 11.
Zhu et al., "Stabilization of proteins encapsulated in injectable poly (lactide-co-glycolide)," Nat. Biotechnol. 18 (2000) 52-57.
Auzanneau et al. , "Synthesis, characterization, and biocompatability ofPEGA resins", "Journal of Peptide Science", May 1995, pp. 31-44, vol. 1.
Belcheva et al., "Crosslinked Poly( ethylene oxide) for drug release systems", Macromol. Symp., 1996, pp. 193-211, vol. 103, Huethig & WepfVerlag, Zug, Switzerland.
Bundgaard et al. "Hydrolysis and Rearrangement of Phthalamic Acid Derivatives and Assessment of Their Potential as Prodrug Forms for Amines" Acta Pharmaceutica Nordica, Elsevier Science Publishers, Amsterdam, NL, vol. 2, No. 5, 1990, pp. 333-342.
Dimitrov et al., "Preparation and Characterization of Polyethylene Oxide Hydrogels with Cytisine", Acta Pharmaceutica Turcica, 2004, pp. 49-54, vol. 46.
Olofsson et al., recent advances in crosslinked dendritic networks, Applied Polymer Science, 2013, 39876, pp. 1-13.
Wathier et al., Dendritic macromers as in situ polymerizing biomaterials for securing, J. Am. Chem. Soc., 2004 vol. 126, pp. 12744-12746.
Fehse et al., "Exenatide Augments First- and Second-Phase Insulin Secretion in Response to Intravenous Glucose in Subjects with Type 2 Diabetes", J Clin. Endocrinol. Metab., 2005, pp. 5991-5997, vol. 90, No. 11, us.
Nathan et al., Diabetologia (2008) 51 :8-11.
Jeong et al., "Thermogelling biodegradable copolymer aqueous solutions for injectable protein delivery and tissue engineering", "Biomacromolecules", 2002, pp. 865-868, vol. 3.
Kanjickal et al., "Effects of sterilization on poly( ethylene glycol) hydrogels", J. Biomed. Mater. Res. Part A., Jan. 9, 2008, pp. 608-617, Wiley InterSciencc (www.interscience.wiley.com).
Kim et al., "Effects of Once-Weekly Dosing of a Long-Acting Release Formulation ofExenatide on Glucose Control and Body Weight in Subjects With Type 2 Diabetes", Diabetes Care, Jun. 2007, pp. 1487-1493, vol. 30, No. 6.
Lee et al., "Drug Delivery Systems Employing 1 ,6-Eiimination: Releasable Poly( ethylene glycol) Conjugates of Proteins", "Bioconjugate Chemistry", 2001, pp. 163-169, vol. 12, Publisher: American Chemical Society.

(56) References Cited

OTHER PUBLICATIONS

Lee et al., "Synthesis, Characterization, and Pharmacokinetic Studies of PEGylated Glucagon-like Peptide-1", Bioconjug. Chem., 2005, pp. 377-382, vol. 16, No. 2.
Lin et al., "Glucagon-like peptide-1 functionalized PEG hydrogels promote survival and function of encapsulated pancreatic beta-cells," Biomacromolecules vol. 10. No. 9, 2009 pp. 2460-2467.
Linnebjerg, et al: "Exenatide: Effect of injection time on postprandial glucose in patients with Type 2 diabetes".Diabetic Medicine, vol. 23, No. 3, 2006, pp. 240-245.
Lucke et al., Pharm. Res. 19 (2002) 175-181.
Luo et al., "A hyaluronic acid-laxol antitumor bioconjugate targeted to cancer cells", "Biomacromolecules", 2000, pp. 208-218, vol. 1.
Markussen et al., J. Biol. Chem. 1991, 266, 18814-18818.
Material Safety Data Sheet-40 kDa Methoxy Poly(Ethylene Glycol) Maleimido-Propionamide, ChiroTech Technology.Ltd.-Product No. 008-016, No. 1, 2 pp. (Feb. 14, 2005).
Matsumura et al., "A New Concept for Macromolecular Therapeutics in Cancer Chemotherapy: Mechanism of Tumoritropic Accumulation of . . . ", "Cancer Research", Dec. 1986, pp. 6387-6392, vol. 46.
Minkov et al., "Structural Studies of Radiation-corsslinked Poly( ethylene oxide)", J. Polymer Sci: Part B: Polymer Phys., 1989, pp. 621-642, vol. 27, John Wiley & Sons, Inc., Hoboken, NJ.
Muller, Prodrug Approaches for Enhancing the Bioavailability of Drugs with Low Solubility, Chemistry & Biodiversity, 2009, 6, 2071-2083.
Na et al., "Monitoring of peptide acylation inside degrading PLGA microspheres by capillary electrophoresis and MALDI-TOF mass spectrometry", "Journal of Controlled Release", 2003, pp. 291-299, vol. 92, Publisher: Elsevier B. V.
Nauck et al., "Glucagon-like peptide I and its derivatives in the treatment of diabetes", Regulatory Peptides, 2005, pp. 135-148, vol. 128.
Peppas et al., "Hydrogels in pharmaceutical formulations", Eur. J. Pharm. Biopharm., 2000, pp. 27-46, vol. 50.
Perez-Tilve et al., "Exendin-4 Potently Decreases Ghrelin Levels in Fasting Rats", Diabetes, Jan. 2007, pp. 143-151, vol. 56.
Prestwich, et al: "Controlled chemical modification of hyaluronic acid: synthesis, applications, and biodegradation of hydrazide derivatives" Journal of Controlled Release, vol. 53, No. 1-3, 1998, pp. 93-103.
Ratner, et al: "Long-term effects of exenatide therapy over 82 weeks on glycaemic control and weight in over-weight metformin-treated patients with type 2 diabetes mellitus." Diabetes, Obesity & Metabolism, vol. 8, No. 4, p. 419-428, 2006.
Rosiak et al., "Hydrogels and their medical applications", Nuclear Instruments and Methods in Physics Research B, 1999, pp. 56-64, vol. 151, Elsevier Science, BY, Netherlands.
Rosiak et al., "Synthesis of hydrogels by irradiation of polymers in aqueous solution", Radiation Physics and Chemistry, 1999, pp. 139-151, vol. 55, Elsevier Science Ltd., Netherlands.
Rouquerol et al. , "Recommendations for the characterization of porous solids", "Pure and Applied Chemistry", 1994, pp. 1739-1758, vol. 66, No. 8.
Satchi-Fainaro et al., "PDEPT: Polymer-Directed Enzyme Prodrug Therapy. 2. HPMA Copolymer-bela-lactamase and HPMA Copolymer-C-Oax as a Model . . . ", "Bioconjugate Chemistry", 2003, pp. 797-804, vol. 14, Publisher: American Chemical Society.
Sawhney et al., "Bioerodible Hydrogels Based on Photopolymerized Poly( ethylene glycol)-co-poly(alpha- hydroxy acid) Diacrylate Macromers", "Macromolecules", 1993, pp. 581-587, vol. 26.
Shafer et al., "Participation of a Neighboring Amide Group in the Decomposition of Esters and Amides of Substituted Phthalamic Acids" J. Org. Chem, 28(7):1899-1901, 1963.
Shan et al., "Prodrug Strategies Based on Intramolecular Cyclization Reactions", J. Pharm. Sci., 86(7):765-777, 1997.
Shao et al., Stabilization of pH-induced degradationof porcine insulin in biodegradable polyester microspheres, Pharm. Dev. Technol. 4(4):633-642, 1999.
Shao et al., "Porcine insulin biodegradable polyester microspheres: stability and in vitro release characteristics," Pharm. Dev. Technol. 5(1):1-9, 2000.
Shechter et al., "[2-Sulfo-9-fluorenylmethoxycarbonylh-exendin-4-a long-acting glucose-lowering prodrug", Biochem, Biophys. Res. Commun., 2003, pp. 386-391, vol. 305.
Shechter et al., "Reversible pegylation of insulin facilitates its prolonged action in vivo," Eur. J. Pharm. Biopharm. 2008(70), 19-28.
Singh et al., Recent Trends in Targeted Anticancer Prodrug and Conjugate Design, Curr. Med. Chem. 2008, 15(18): 1802-1826.
Sintzel et al., "Influence of irradiation sterilization on polymers used as drug carriers—A review", Drug Dev. Ind. Pharm., 23(9):857-878, 1997.
Sohma et al., "Development of water-soluble prodrugs of the HIV-1 protease inhibitor KNI-727: Importance of the conversion time for higher gastrointestinal absorption of prodrugs based on spontaneous chemica 1 cleavage." J. Med. Chem., 46(19):4124-4135, 2003.
Surini et al., "Release phenomena of insulin from an implantable device composed of a polyion complex of chitosan and sodium hyaluronate", J. Control. Release, 2003, 291-301, vol. 90(3).
Testa et al., "Hydrolysis in Drug and Prodrug Metabolism- Chemistry, Biochemistry and Enzymology", 2002, pp. 1-780, Publisher: Wiley-VCH.
Testa, Prodrug Research: Futile or Fertile?, Biochem. Pharm. 2004, 68, 2097-2106.
Tsubery et al., "Prolonging the action of protein and peptide drugs by a novel approach of reversible polyethylene glycol modification", J. Biol. Chem., Sep. 10, 2004, pp. 38118-38124, vol. 279, No. 37.
Wiwattanapatapee et al., "Dendrimers conjugates for colonic delivery of 5-aminosalicylic acid", J. Control. Release, 2003, 1-9, vol. 88.
Ettmayer, et al. "Lessons Learned from Marketed and Investigational Prodrugs", J. Med. Chem. 2004, 47(10), 2393-2404.
Office Action issued in U.S. Appl. No. 13/387,959 dated Nov. 28, 2014.
Final Office Action issued in U.S. Appl. No. 10/960,851 as mailed on Oct. 5, 2009.
Final Office Action issued in U.S. Appl. No. 10/960,851 as mailed on Oct. 18, 2010.
Non Final Office Action issued in U.S. Appl. No. 10/960,851 as mailed on Dec. 29, 2008.
Non Final Office Action issued in U.S. Appl. No. 10/960,851 as mailed on Feb. 18, 2010.
Notice of Allowance issued in U.S. Appl. No. 10/960,851 as mailed on Mar. 3, 2011.
Restriction Requirement issued in U.S. Appl. No. 10/960,851 as mailed on Jul. 24, 2007.
Restriction Requirement issued in U.S. Appl. No. 10/960,851 as mailed on Jun. 23, 2008.
Supplemental Notice of Allowability issued in U.S. Appl. No. 10/960,851 as mailed on Apr. 26, 2011.
Non Final Office Action issued in U.S. Appl. No. 12/663,628 as mailed on Dec. 5, 2013.
Non Final Office Action issued in U.S. Appl. No. 12/663,628 as mailed on May 10, 2013.
Restriction Requirement issued in U.S. Appl. No. 12/663,628 as mailed on Nov. 26, 2012.
Restriction Requirement issued in U.S. Appl. No. 12/663,628 as mailed on Oct. 3, 2012.
Non Final Office Action issued in U.S. Appl. No. 12/865,693 as mailed on Jan. 16, 2014.
Non Final Office Action issued in U.S. Appl. No. 12/865,693 as mailed on Jul. 18, 2013.
Restriction Requirement issued in U.S. Appl. No. 12/865,693 as mailed on Jan. 9, 2013.
Non Final Office Action issued in U.S. Appl. No. 13/111,777 as mailed on Dec. 27, 2013.
Restriction Requirement issued in U.S. Appl. No. 13/111,777 as mailed on Oct. 16, 2012.
Final Office Action issued in U.S. Appl. No. 13/387,959 as mailed on Apr. 10, 2014.
Non Final Office Action issued in U.S. Appl. No. 13/387,959 as mailed on Aug. 30, 2013.

(56) References Cited

OTHER PUBLICATIONS

Restriction Requirement issued in U.S. Appl. No. 13/387,959 as mailed on Jul. 10, 2013.
Restriction Requirement issued in U.S. Appl. No. 13/387,971 as mailed on Nov. 22, 2013.
Final Office Action issued in U.S. Appl. No. 13/505,214 as mailed on Apr. 3, 2014.
Non Final Office Action issued in U.S. Appl. No. 13/505,214 as mailed on Nov. 26, 2013.
Non Final Office Action issued in U.S. Appl. No. 13/822,170 as mailed on Mar. 3, 2014.
Restriction Requirement issued in U.S. Appl. No. 13/822,170 as mailed on Nov. 22, 2013.
Belikov, "Fannazevticheskaya Khimiya", M., Vysshaya shoka, 1993, t. I, str. 43-47 (= Pham1accutical Chemistry, Moscow, High School, 1993, vol. 1 p. 43-47) (article in Russian with English abstract).
Harkevich, "Farmakologiya", M., Medizina, 1987, str.47-48 (= Pharmacology, Moscow, Medicine, 1987, p. 47-48) with Engl (article in Russian with English abstract).
Harkevich, "Farmakologiya", M., Medizina, 1987, str.50-52 (=Pharmacology, Moscow, Medicine, 1987, p. 50-52). (article in Russian with English abstract).
International Search Report corresponding to PCT/EP2005/007316, dated Oct. 16, 2006.
International Search Report corresponding to PCT/EP2008/056981, dated Jun. 26, 2009.
International Search Report corresponding to PCT/EP2009/051079, dated Jul. 22, 2009.
International Search Report corresponding to PCT/EP2010/061155, dated Nov. 26, 2010.
International Search Report issued in PCT/EP2010/061159 as mailed on Nov. 17, 2010.
International Search Report issued in PCT/EP2010/061160 as mailed on Nov. 16, 2010.
International Search Report corresponding to PCT/EP2010/066404, dated Dec. 10, 2010.
International Search Report issued in PCT/EP2011/066097 as mailed on Feb. 27, 2012.
Jarry et al., Chem. Pharm. Bull., 50(10), 1335-1340, 2002.
Kudrin, "Problemy vzaimodeistviya lekarstvennykh veshestv", Farmaziya, 1983, No. 2, str. 71 (= Problems of Interaction of medicinal substances, Pharmacy, 1983, No. 2, p. 71). (article in Russian with English abstract).
Nektar, Inc., "Nektar Molecule Engineering- Polyethylene Dlycol and Derivatives for Advanced PEGylation", "Nektar Advanced PEGylation (Catalog 2004)", 2003.
Physicians' Desk Reference 57th Edition, 2003, pp. 2768-2772.

\* cited by examiner

PRODRUGS COMPRISING AN INSULIN LINKER CONJUGATE

CROSS REFERENCE TO RELATED APPLICATIONS

The instant application is a §371 of International Patent Application PCT/EP2010/061159 filed on Jul. 30, 2010; and claims priority to European Patent Application No. EP 09167027.3 filed on Jul. 31, 2009, European Patent Application No. EP 09179818.1 filed on Dec. 18, 2009, European Patent Application No. EP 09179336.4 filed on Dec. 15, 2009, and EP 09174525.7 filed on Oct. 29, 2009.

BACKGROUND

The present invention relates to prodrugs, pharmaceutical compositions comprising said prodrugs as well as their use as a medicament for treating or preventing diseases or disorders which can be treated by insulin.

Insulin therapy is characterized by a high need for keeping the insulin drug release within very strict levels as the therapeutic window is narrow, and the adverse effects of hyperinsulinemia can potentially be life threatening. Numerous insulin preparations have been commercialized, with different action profiles to suit specific needs of the diabetic population. Fast acting insulin analogs are administered just before meals, in order to control the peak in plasma glucose following food ingestion, whereas long acting insulin analogs are typically given once or twice a day to provide a steady basal insulin level.

Therefore, there is a clear need for novel long acting preparations of insulin, that continuously release insulin throughout the entire period between administrations.

WO-A 2006/003014 describes a hydrogel capable of releasing insulin with the possibility of reduced dosing frequency as compared to standard daily basal insulin injections. However, the insulin is released at a rate too fast for ensuring strict insulinotropic control for periods extending 2 days. In fact the insulin is released with a half life of approximately 30 hours, meaning that the prodrug must be administered at least every 30 hours in order for the peak to trough ratio to be below 2 at steady state.

The concept of preparing a reversible polymer prodrug conjugate of insulin has been explored by Shechter et al. and described in scientific articles and patent applications (e.g. European Journal of Pharmaceutics and Biopharmaceutics 2008(70), 19-28 and WO-A 2004/089280). The insulin is conjugated to a 40 kDa PEG polymer through a fluorenyl-linker. Hydrolysis of said linker molecule releases insulin with a half life of approximately 30 hours, meaning that the prodrug must be administered at least every 30 hours in order for the peak to trough ratio to be below 2 at steady state.

Other attempts of reducing the insulin dosing frequency have been made. Hinds et al., Journal of Controlled Release, 2005 (104), 447-460, describe a method of producing a once weekly insulin, by first permanently PEGylating the insulin molecule and then subsequently microencapsulating the PEGylated insulin in PLGA microparticles. In this case, the insulin was subjected to substantial structural modification through permanent modification by a high molecular weight polymer entity. Such high molecular weight modified insulins may exhibit reduced efficacy by diminished receptor binding and may also exhibit injeciton site reactions such as lipoatrophy due to the extended presence of high concentrations of the high molecular weight insulin in the subcutaneous tissue. Furthermore, such PEGylated insulins will exhibit a lower distribution volume, which is of particular disadvantage in the treatment of diabetes.

Nevertheless, PEGylation of insulin apparently serves to protect the peptide from deterioration in the PLGA polymer formulation. The effect of PEGylation to protect peptides from acylation in a degrading PLGA formulation was demonstrated for octreotide by D. H. Na et al., AAPS PharmSciTech 2003, 4 (4) Article 72.

PLGA encapsulation of proteins has been shown to cause side reactions of the polymer esters with peptide or protein amino groups. Lactic acid acylation products have been observed after exposure of the formulations to buffered solutions at neutral pH (G. Zhu et al., Nature Biotechnology 18 (2000) 52-57; A. J. Domb et al., Pharm. Res. 11 (1994) 865-868; A. Lucke et al., Pharm. Res. 19 (2002) 175-181).

Specifically for insulin, detrimental effects of polymer formulations have been demonstrated by P. G. Shao et al., Pharm. Dev. Technol. 4 (1999) 633-642 (see also P. G. Shao et al., Pharm. Dev. Technol. 5 (2000) 1-9).

Furthermore, insulin is known to readily undergo side reactions that are related to the presence of three disulfide bridges in the molecule. For instance, insulin may be split into A and B chains by disulfide bond cleavage or dimers or oligomers may be formed due to disulfide interchange reactions. Such disulfide reshuffling is particularly likely, if insulin molecules are forced into close contact in a random way. This intrinsic lability of the insulin molecule has significantly hampered progress in long-acting depot development and prevented the use of other polymer formulations where insulin is encapsulated in a way similar to an amorphous precipitate which is well known to give rise to various degradation products arising from extensive disulfide exchange.

Therefore the challenge remains to develop long-acting insulin without compromising the insulin pharmcacodynamics by permanent attachment of a high molecular weight entity or by causing structural damage to the molecule while during its presence in the depot.

Thus an object of the present invention is to provide an insulin containing prodrug that meets at least partially the above requirements.

SUMMARY

The object is achieved by a prodrug or a pharmaceutically acceptable salt thereof comprising an insulin linker conjugate D-L$^1$, wherein
D is insulin moiety; and
L$^1$ is:

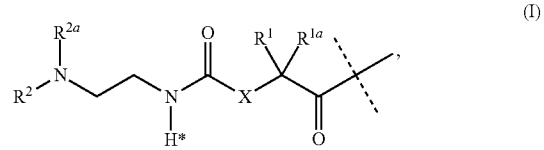

wherein the dashed line indicates the attachment to one of the amino groups of the insulin by forming an amide bond;
X is C(R$^3$R$^{3a}$); or N(R$^3$);
R$^{1a}$, R$^{3a}$ are independently selected from the group consisting H, NH(R$^{2b}$), N(R$^{2b}$)C(O)R$^4$ and C$_{1-4}$ alkyl;
R$^1$, R$^2$ R$^{2a}$, R$^{2b}$, R$^3$, R$^4$ are independently selected from the group consisting of H and C$_{1-4}$ alkyl,
wherein L$^1$ is substituted with one L$^2$-Z and optionally further substituted, provided that the hydrogen marked with the asterisk in formula (I) is not replaced by a substituent and wherein L² is a single chemical bond or a spacer; and Z is a hydrogel.

It was now surprisingly discovered, that a prodrug of the present invention may provide insulin release from a subcutaneous depot in structurally intact form over time periods of at least 2 days between administrations. As a further advantage structural integrity of the released insulin may be provided by a well-hydrated polymer matrix minimizing intermolecular contact of insulin molecules and sustained release may be enabled by means of a self-cleaving prodrug linker between the insulin and the polymer matrix.

Thus it should be possible to administer insulin in form of a prodrug of the present invention less frequently than current long acting insulins. Further advantages should be a small peak to trough ratio, which greatly reduce the risk of hypoglycemic episodes. This may help patients to reduce the frequency of injections, while being able to maintain optimal control the plasma levels of insulin and consequently blood glucose.

BRIEF DESCRIPTION OF THE FIGURES

FIG. 1a: UPLC chromatogram of insulin-linker conjugate 12a.

DETAILED DESCRIPTION

Figure 1A:
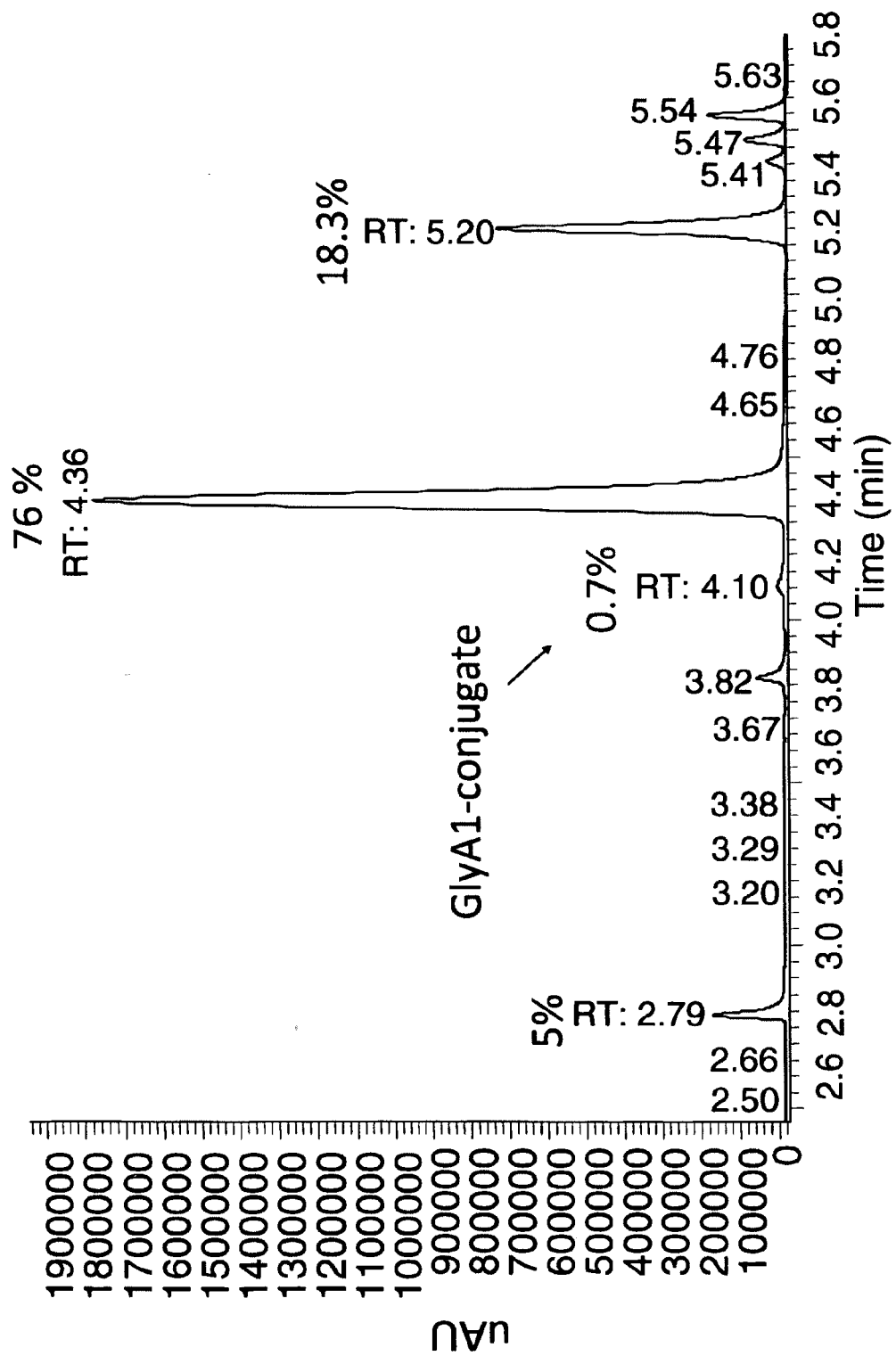

"Insulin" according to the present invention means recombinant human insulin, Lantus®, insulin glargine, insulin detemir, insulin glulisine, insulin aspart, insulin lispro, insulin conjugated to low-molecular-weight PEG. Low-molecular-weight PEG has a molecular weight smaller than 10 kDa.

Insulin bound to a non-biologically active linker is referred to as "insulin moiety".

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues.

The insulin analogues may be such wherein position 28 of the B chain may be modified from the natural Pro residue to one of Asp, Lys, or Iie. In another aspect Lys at position B29 is modified to Pro. Also, Asn at position A21 may be modified to Ala, Gln, Glu, Gly, His, Iie, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

With desB30 insulin", "desB30 human insulin" is meant a natural insulin or an analogue thereof lacking the B30 amino acid residue. Similarly, "desB29desB30 insulin" or desB29desB30 human insulin" means a natural insulin or an analogue thereof lacking the B29 and B30 amino acid residues.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

"Non-biologically active linker" means a linker which does not show the pharmacological effects of the drug derived from the biologically active agent.

"Protective groups" refers to a moiety which temporarily protects a chemical functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

"Protected functional groups" means a chemical functional group protected by a protective group.

"Acylating agent" means a moiety of the structure R—(C=O)—, providing the acyl group in an acylation reaction, optionally connected to a leaving group, such as acid chloride, N-hydroxy succinimide, pentafluorphenol and para-nitrophenol.

"Alkyl" means a straight-chain or branched carbon chain. Each hydrogen of an alkyl carbon may be replaced by a substituent.

"Aryl" refers to any substituent derived from a monocyclic or polycyclic or fused aromatic ring, including heterocyclic rings, e.g. phenyl, thiophene, indolyl, napthyl, pyridyl, which may optionally be further substituted.

"Acyl" means a chemical functional group of the structure R—(C=O)—, wherein R is an alkyl or aryl.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

Accordingly, "$C_{1-18}$ alkyl" means an alkyl chain having 1 to 18 carbon atoms and "$C_{8-18}$ alkyl" means an alkyl chain having 8 to 18 carbon atoms. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms, e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-50}$ alkynyl carbon may be replaced by a substituent as further specified. Accordingly, the term "alkynyl" relates to a carbon chaim with at least one carbon carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent. The term "$C_{3-7}$ cycloalkyl" or "$C_{3-7}$ cycloalkyl ring" also includes bridged bicycles like norbonane or norbonene. Accordingly, "$C_{3-5}$ cycloalkyl" means a cycloalkyl having 3 to 5 carbon atoms.

Accordingly, "$C_{3-10}$ cycloalkyl" means a cyclic alkyl having 3 to 10 carbon atoms, e.g. $C_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or unsaturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

In case the insulin prodrugs comprising the compounds according to formula (I) contain one or more acidic or basic groups, the invention also comprises their corresponding pharmaceutically or toxicologically acceptable salts, in particular their pharmaceutically utilizable salts. Thus, the insulin prodrugs comprising the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Insulin prodrugs comprising the compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the insulin prodrugs comprising the compounds of the formula (I) simultaneously contain acidic and basic groups in the molecule, the invention also includes, in addition to the salt forms mentioned, inner salts or betaines (zwitterions). The respective salts according to insulin prodrugs comprising the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the insulin prodrugs comprising the compounds of the formula (I) which, owing to low physiological compatibility, are not directly suitable for use in pharmaceuticals but which can be used, for example, as intermediates for chemical reactions or for the preparation of pharmaceutically acceptable salts.

To enhance physicochemical or pharmacokinetic properties of a drug, such as insulin, in vivo, such drug can be conjugated with a carrier. If the drug is transiently bound to a carrier and/or a linker, such systems are commonly assigned as carrier-linked prodrugs. According to the definitions provided by IUPAC (as given under <http://www.chem.qmul.ac.uk/iupac.medchem>, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in such carrier-linked prodrugs are transient, meaning that they are non-enzymatically hydrolytically degradable (cleavable) under physiological conditions (aqueous buffer at pH 7.4, 37° C.) with half-lives ranging from, for example, one hour to three months.

Suitable carriers are polymers and can either be directly conjugated to the linker or via a non-cleavable spacer. The term "insulin hydrogel prodrug" refers to carrier-linked prodrugs of insulin, wherein the carrier is a hydrogel. The terms "hydrogel prodrug" and "hydrogel-linked prodrug" refer to prodrugs of biologically active agents transiently linked to a hydrogel and are used synonymously. A "hydrogel" may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

"Free form" of a drug refers to the drug in its unmodified, pharmacologically active form, such as after being released from a polymer conjugate.

The terms "drug", "biologically active molecule", "biologically active moiety", "biologically active agent", "active agent", and the like mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Specifically, the terms "drug", "biologically active molecule", "biologically active moiety", "biologically active agent", "active agent", and the like refer to insulin.

A "therapeutically effective amount" of insulin as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

"Stable" and "stability" means that within the indicated storage time the hydrogel conjugates remain conjugated and do not hydrolyze to a substantial extent and exhibit an acceptable impurity profile relating to insulin. To be considered stable, the composition contains less than 5% of the drug in its free form.

The term "pharmaceutically acceptable" means approved by a regulatory agency such as the EMEA (Europe) and/or the FDA (US) and/or any other national regulatory agency for use in animals, preferably in humans.

"Pharmaceutical composition" or "composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

"Dry composition" means that the insulin hydrogel prodrug composition is provided in a dry form in a container. Suitable methods for drying are spray-drying and lyophilization (freeze-drying). Such dry composition of insulin hydrogel prodrug has a residual water content of a maximum of 10%, preferably less than 5% and more preferably less than 2% (determined according to Karl Fischer). The preferred method of drying is lyophilization. "Lyophilized composition" means that the insulin hydrogel polymer prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to bring back the original form of a composition.

"Reconstitution solution" refers to the liquid used to reconstitute the dry composition of a insulin hydrogel prodrug prior to administration to a patient in need thereof.

"Container" means any container in which the insulin hydrogel prodrug composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as arginine, glycine, glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the polymer prodrug. Stabilisation is achieved by strengthening of the protein-stabilising forces, by destabilisation of the denatured state, or by direct binding of excipients to the protein.

"Anti-adsorption agents" refers to mainly ionic or non-ionic surfactants or other proteins or soluble polymers used to coat or adsorb competitively to the inner surface of the composition's container. Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"Sealing a container" means that the container is closed in such way that it is airtight, allowing no gas exchange between the outside and the inside and keeping the content sterile.

The term "reagent" or "precursor" refers to an intermediate or starting material used in the assembly process leading to a prodrug of the present invention.

The term "chemical functional group" refers to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

A "degradable interconnected functional group" is a linkage comprising a biodegradable bond which on one side is connected to a spacer moiety connected to a backbone moiety and on the other side is connected to the crosslinking moiety. The terms "degradable interconnected functional group", "biodegradable interconnected functional group", "interconnected biodegradable functional group" and "interconnected functional group" are used synonymously.

The terms "blocking group" or "capping group" are used synonymously and refer to moieties which are irreversibly connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups.

The term "interconnectable functional group" refers to chemical functional groups, which participate in a radical polymerization reaction and are part of the crosslinker reagent or the backbone reagent.

The term "polymerizable functional group" refers to chemical functional groups, which participate in a ligation-type polymerization reaction and are part of the crosslinker reagent and the backbone reagent.

A backbone moiety may comprise a spacer moiety which at one end is connected to the backbone moiety and on the other side to the crosslinking moiety.

The term "derivatives" refers to chemical functional groups suitably substituted with protecting and/or activation groups or to activated forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

"Non-biologically active linker" means a linker which does not show the pharmacological effects of the drug (D-H) derived from the biologically active moiety.

The terms "spacer", "spacer group", "spacer molecule", and "spacer moiety" are used interchangeably and if used to describe a moiety present in the hydrogel carrier of the invention, refer to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups. Structures shown for backbone reagents, backbone moieties, crosslinker reagents, and crosslinker moieties are thus only representative examples.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

The term "poly(ethylene glycol) based polymeric chain" or "PEG based chain" refers to an oligo- or polymeric molecular chain.

Preferably, such poly(ethylene glycol) based polymeric chain is connected to a branching core, it is a linear poly(ethylene glycol) chain, of which one terminus is connected to the branching core and the other to a hyperbranched dendritic moiety. It is understood that a PEG-based chain may be terminated or interrupted by alkyl or aryl groups optionally substituted with heteroatoms and chemical functional groups.

If the term "poly(ethylene glycol) based polymeric chain" is used in reference to a crosslinker reagent, it refers to a crosslinker moiety or chain comprising at least 20 weight % ethylene glycol moieties.

Preferably, in formula (I) $R^2$ is replaced by $L^2$-Z.
Preferably, in formula (I) $R^1$ is replaced by $L^2$-Z.
Preferably, in formula (I) X is $N(R^3)$.
Preferably, in formula (I) X is $C(R^3R^{3a})$ and $R^{3a}$ is $N(R^{2b})C(O)R^4$.
Preferably, in formula (I) X is $C(R^3R^{3a})$ and $R^{1a}$ is replaced by $L^2$-Z.
Preferably, X is $C(R^3R^{3a})$, $R^{3a}$ is $N(R^{2b})$-$L^2$-Z.

Preferred prodrugs of the present invention comprise an insulin linker conjugate D-$L^1$, wherein $L^1$ of formula (I) is represented by formulae (Ia), (Ib), (Ic) or (Id):

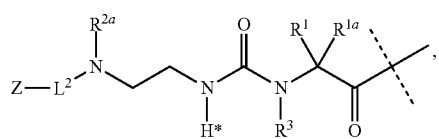

(Ia)

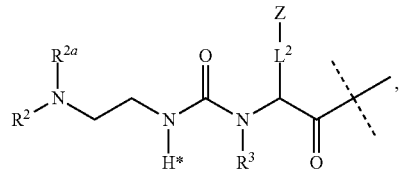

(Ib)

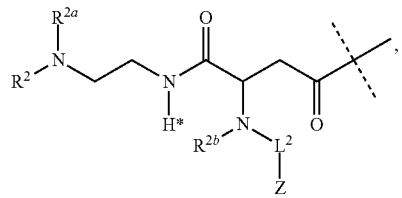

(Ic)

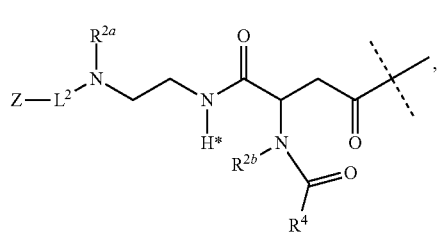

(Id)

wherein $R^1$, $R^{1a}$, $R^2$, $R^{2a}$, $R^{2b}$, $R^3$, $R^4$, $L^2$, Z have the meaning as indicated herein and wherein $L^1$ is optionally further substituted, provided that the hydrogen marked with the asterisk in formula (Ia) to (Id) is not replaced by a substituent.

Preferably, the insulin moiety is attached to $L^1$ through the nitrogen $N^{\alpha A1}$ or through the nitrogen of a lysine side chain of the insulin moiety.

Preferably, the insulin moiety is recombinant human insulin.

As shown in, e.g., formulae (Ia) to (Id) one hydrogen is replaced by the group $L^2$-Z.

In general, $L^2$ can be attached to $L^1$ at any position apart from the replacement of the hydrogen marked with an asterisk in formula (I). Preferably, one of the hydrogens given by $R^1$, $R^{1a}$, $R^2$, $R^{2a}$, $R^{2b}$, $R^3$, $R^{3a}$, $R^4$ directly or as hydrogen of the $C_{1-4}$ alkyl or further groups is replaced by $L^2$-Z.

Furthermore, $L^1$ may be optionally further substituted. In general, any substituent may be used as far as the cleavage principle is not affected. However it is preferred that $L^1$ is not further substituted.

Preferably, one or more further optional substituents are independently selected from the group consisting of halogen; CN; $COOR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $SR^9$; $N(R^9R^{9a})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)OR^{9a}$; $N(R^9)C(O)N(R^{9a}R^{9b})$; $OC(O)N(R^9R^{9a})$; T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

$R^9$, $R^{9a}$, $R^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N ($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein T is optionally substituted with one or more $R^{10}$, which are the same or different;

$R^{10}$ is halogen; CN; oxo (=O); COOR$^{12}$; OR$^{12}$; C(O)R$^{12}$; C(O)N($R^{12}R^{12a}$); S(O)N($R^{12}R^{12a}$); S(O)$_2$R$^{12}$; S(O)R$^{12}$; N($R_{12}$)S(O)$_{2N}$($R^{12a}R^{12b}$); SR$_{12}$; N($R^{12}R^{12a}$); NO$_2$; OC(O)R$^{12}$; N($R^{12}$)C(O)R$^{12a}$; N($R^{12}$)S(O)$_2$R$^{12a}$; N($R^{12}$)S(O)R$^{12a}$; N($R^{12}$)C(O)OR$^{12a}$; N($R^{12}$)C(O)N($R^{12}R^{12a}$); OC(O)N($R^{12}R^{12a}$); or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or at the end of the carbon chain between the carbon and hydrogen.

$L^2$ is a single chemical bond or a spacer. In case $L^2$ is a spacer, it is preferably defined as the one or more optional substituents defined above, provided that $L^2$ is substituted with Z.

Accordingly, when $L^2$ is other than a single chemical bond, $L^2$-Z is COOR$^9$; OR$^9$; C(O)R$^9$; C(O)N($R^9R^{9a}$); S(O)$_2$N($R^9R^{9a}$); S(O)N($R^9R^{9a}$); S(O)$_2$R$^9$; S(O)R$^9$; N($R^9$)S(O)$_2$N($R^{9a}R^{9b}$); SR$^9$; N($R^9R^{9a}$); OC(O)R$^9$; N($R^9$)C(O)R$^{9a}$; N($R^9$)S(O)$_2$R$^{9a}$; N($R^9$)S(O)R$^{9a}$; N($R^9$)C(O)OR$^{9a}$; N($R^9$)C(O)N($R^{9a}R^{9b}$); OC(O)N($R^9R^{9a}$); T; $C_{1-50}$ alkyl; $C_{2-50}$ alkenyl; or $C_{2-60}$ alkynyl, wherein T; $C_{1-60}$ alkyl; $C_{2-60}$ alkenyl; and $C_{2-60}$ alkynyl are optionally substituted with one or more $R^{10}$, which are the same or different and wherein $C_{1-60}$ alkyl; $C_{2-60}$ alkenyl; and $C_{2-60}$ alkynyl are optionally interrupted by one or more groups selected from the group consisting of -T-, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)R$^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

$R^9$, $R^{9a}$, $R^{9b}$ are independently selected from the group consisting of H; Z; T; and $C_{1-60}$ alkyl; $C_{2-60}$ alkenyl; or $C_{2-60}$ alkynyl, wherein T; $C_{1-50}$ alkyl; $C_{2-60}$ alkenyl; and $C_{2-50}$ alkynyl are optionally substituted with one or more $R^{10}$, which are the same or different and wherein $C_{1-60}$ alkyl; $C_{2-60}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)R$^{11}$; —N($R^{11}$)C(O)—; —N($R^{11}$)S(O)$_2$—; N($R^{11}$)S(O)—; —N($R^{11}$)C(O)O—; —N($R^{11}$)C(O)O—; —N($R^{11a}$)—, and —OC(O)N($R^{11}R^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein t is optionally substituted with one or more $R^{10}$, which are the same or different;

$R^{10}$ is Z; halogen; CN; oxo (=O); COOR$^{12}$; OR$^{12}$; C(O)R$^{12}$; C(O)N($R^{12}R^{12a}$); S(O)$_2$N($R^{12}R^{12a}$); S(O)N($R^{12}R^{12a}$); S(O)$_2$R$^{12}$; S(O)R$^{12}$; N($R^{12}$)S(O)$_2$N($R^{12a}R^{12}$); SR$^{12}$; N($R^{12}R^{12a}$); NO$_2$; OC(O)R$^{12}$; N($R^{12}$)C(O)R$^{12a}$; N($R^{12}$)S(O)$_2$R$^{12a}$; N($R^{12}$)S(O)R$^{12a}$; N($R^{12}$)C(O)OR$^{12a}$; N($R^{12}$)C(O)N($R^{12a}R^{12b}$); OC(O)N($R^{12}R^{12a}$); or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; Z; or $C_{1-6}$ alkyl, wherein $C_{1-6}$ alkyl is optionally substituted with one or more halogen, which are the same or different;

provided that only one of $R^9$, $R^{9a}$, $R^{9b}$, $R^{10}$, $R^{11}$, $R^{11a}$, $R^{12}$, $R^{12a}$, $R^{12b}$ is Z.

More preferably, $L^2$ is a $C_{1-20}$ alkyl chain, which is optionally interrupted by one or more groups independently selected from —O—; and C(O)N($R^{3aa}$); optionally substituted with one or more groups independently selected from OH; and C(O)N($R^{3aa}R^{3aaa}$); and wherein $R^{3aa}$, $R^{3aaa}$ are independently selected from the group consisting of H; and $C_{1-4}$ alkyl.

Preferably, $L^2$ has a molecular weight in the range of from 14 g/mol to 750 g/mol.

Preferably, $L^2$ is attached to Z via a terminal group selected from

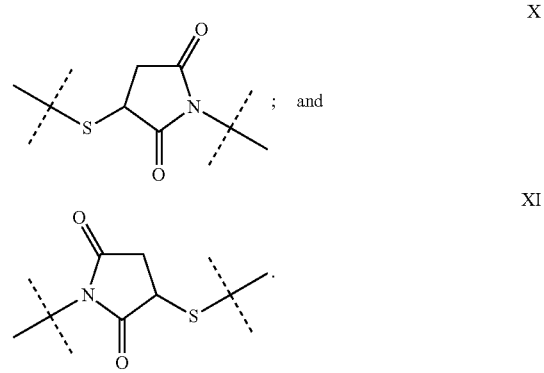

In case $L^2$ has such terminal group it is furthermore preferred that $L^2$ has a molecular weight in the range of from 14 g/mol to 500 g/mol calculated without such terminal group.

Preferably, the covalent attachment formed between the linker and hydrogel Z is a permanent bond.

Preferably, the hydrogel Z is a biodegradable polyethylene glycol (PEG) based water-insoluble hydrogel. The term "PEG based" as understood herein means that the mass proportion of PEG chains in the hydrogel is at least 10% by weight, preferably at least 25%, based on the total weight of the hydrogel. The remainder can be made up of other spacers and/or oligomers or polymers, such as oligo- or polylysines.

Moreover the term "water-insoluble" refers to a swellable three-dimensionally crosslinked molecular network froming the hydrogel. The hydrogel if suspended in a large surplus of water or aqueous buffer of physiological osmolality may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

According to this invention, the hydrogel may be composed of backbone moieties interconnected by hydrolytically degradable bonds.

Preferably, L² is connected to a backbone moiety

Preferably, the backbone moiety has a molecular weight in the range of from 1 kDa to 20 kDa, more preferably from 1 kDa to 15 kDa and even more preferably from 1 kDa to 10 kDa. The backbone moieties are preferably also PEG-based comprising one or more PEG chains.

In a hydrogel carrying drug-linker conjugates according to the invention, a backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups. Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups and hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

In such carrier-linked prodrugs according to the invention, it is desirable that almost all drug release (>90%) has occurred before a significant amount of release of the backbone moieties (<10%) has taken place. This can be achieved by adjusting the carrier-linked prodrug's half-life versus the degradation kinetics of the hydrogel according to the invention.

Preferentially, a backbone moiety is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may be comprised of poly- or oligoalcohols in bound form, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be comprised of poly- or oligoamines such as ornithine, diaminobutyric acid, trilysine, tetralysine, pentalysine, hexalysine, heptalysine, octalysine, nonalysine, decalysine, undecalysine, dodecalysine, tridecalysine, tetradecalysine, pentadecalysine or oligolysines, polyethyleneimines, polyvinylamines in bound form.

Preferably, the branching core extends three to sixteen PEG-based polymeric chains, more preferably four to eight. Preferred branching cores may be comprised of pentaerythritol, ornithine, diaminobutyric acid, trilysine, tetralysine, pentalysine, hexalysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a linear poly(ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferably, a PEG-based polymeric chain is a suitably substituted polyethylene glycol derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from <http://www.jenkemusa.com> on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 1 kDa to 15 kDa and even more preferably 1 kDa to 10 kDa.

It is understood that the terminal amine groups of the above mentioned multi-arm molecules are present in bound form in the backbone moiety to provide further interconnected functional groups and reactive functional groups of a backbone moiety.

It is preferred that the sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties are comprised of trilysine, tetralysine, pentalysine, hexalysine, heptalysine in bound form, most preferred trilysine, pentalysine or heptalysine, ornithine, diaminobutyric acid in bound form.

Most preferably, the hydrogel carrier of the present invention is characterized in that the the backbone moiety has a quarternary carbon of formula $C(A-Hyp)_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected functional groups and reactive functional groups.

Preferably, each A is independently selected from the formula $-(CH_2)_{n1}(OCH_2CH_2)_nX-$, wherein n1 is 1 or 2; n is an integer in the range of from 5 to 50; and X is a chemical functional group covalently linking A and Hyp.

Preferably, A and Hyp are covalently linked by an amide linkage.

Preferably, the dendritic moiety Hyp is a hyperbranched polypeptide. Preferably, the hyperbranched polypeptide comprises lysine in bound form. Preferably, each dendritic moiety Hyp has a molecular weight in the range of from 0.4 kDa to 4 kDa. It is understood that a backbone moiety $C(A-Hyp)_4$ can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

The reaction of polymerizable functional groups a backbone reagent, more specifically of Hyp with the polymerizable functional groups of polyethyleneglycol based crosslinker reagents results in a permanent amide bond.

Preferably, $C(A-Hyp)_4$ has a molecular weight in the range of from 1 kDa to 20 kDa, more preferably 1 kDa to 15 kDa and even more preferably 1 kDa to 10 kDa.

One preferred backbone moiety is shown below, dashed lines indicate interconnecting biodegradable linkages to crosslinker moieties and n is an integer of from 5 to 50:

The terms "hydrolytically degradable", "biodegradable" or "hydrolytically cleavable", "auto-cleavable", or "self-cleavage", "self-cleavable", "transient" or "temporary" refers within the context of the present invention to bonds and linkages which are non-enzymatically hydrolytically degradable or cleavable under physiological conditions (aqueous buffer at pH 7.4, 37° C.) with half-lives ranging from one hour to three months, including, but are not limited to, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like.

If present in a hydrogel according to the invention as degradable interconnected functional group, preferred biodegradable linkages are carboxylic esters, carbonates, phosphoesters and sulfonic acid esters and most preferred are carboxylic esters or carbonates.

Permanent linkages are non-enzymatically hydrolytically degradable under physiological conditions (aqueous buffer at pH 7.4, 37° C.) with half-lives of six months or longer, such as, for example, amides.

To introduce the hydrolytically cleavable bonds into the hydrogel carrier of the invention, the backbone moieties can be directly linked to each other by means of biodegradable bonds.

In one embodiment, the backbone moieties of the biodegradable hydrogel carrier may be linked together directly, i.e. without crosslinker moieties. The hyperbranched dendritic moieties of two backbone moieties of such biodegradable hydrogel may either be directly linked through an interconnected functional group that connects the two hyperbranched dendritic moieties. Alternatively, two hyperbranched dendritic moieties of two different backbone moieties may be interconnected through two spacer moieties connected to a backbone moiety and on the other side connected to a crosslinking moiety separated by an interconnected functional groups.

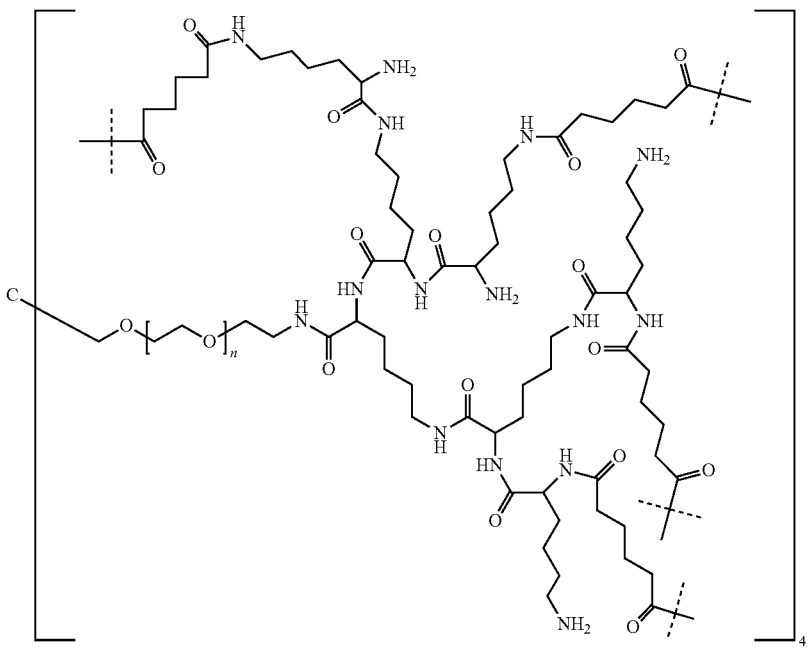

Biodegradability of the hydrogels according to the present invention is achieved by introduction of hydrolytically degradable bonds.

Alternatively, backbone moieties may be linked together through crosslinker moieties, each crosslinker moiety is terminated by at least two of the hydrolytically degradable bonds. In addition to the terminating degradable bonds, the crosslinker moieties may contain further biodegradable bonds. Thus, each end of the crosslinker moiety linked to a backbone moiety comprises a hydrolytically degradable bond, and additional biodegradable bonds may optionally be present in the crosslinker moiety.

Preferably, the biodegradable hydrogel carrier is composed of backbone moieties interconnected by hydrolytically degradable bonds and the backbone moieties are linked together through crosslinker moieties.

The biodegradable hydrogel carrier may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

Preferably, crosslinker moieties have a molecular weight in the range of from 60 Da to 5 kDa, more preferably, from 0.5 kDa to 4 kDa, even more preferably from 1 kDa to 4 kDa, even more preferably from 1 kDa to 3 kDa. In one embodiment, a crosslinker moiety consists of a polymer.

In addition to oligomeric or polymeric crosslinking moieties, low-molecular weight crosslinking moieties may be used, especially when hydrophilic high-molecular weight backbone moieties are used for the formation of a biodegradable hydrogel according to the invention.

Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each m ethylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

In one embodiment, monomers constituting the polymeric crosslinker moieties are connected by biodegradable bonds. Such polymeric crosslinker moieties may contain up to 100 biodegradable bonds or more, depending on the molecular weight of the crosslinker moiety and the molecular weight of the monomer units. Examples for such crosslinker moieties are poly(lactic acid) or poly(glycolic acid) based polymers. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each m ethylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

In a preferred embodiment of the present invention the crosslinker moiety consists of PEG, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties connected to a backbone moiety and on the other side is connected to a crosslinking moiety consist of 3 to 12 carbon atoms, most preferably between 5 and 8 carbon atoms and may be substituted at one or more carbon atom. Preferred substituents are alkyl groups, hydroxyl groups or amido groups or substituted amino groups. One or more of the aliphatic dicarboxylic acid's methylene groups may optionally be substituted by 0 or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

One preferred crosslinker moiety is shown below; dashed lines indicate interconnecting biodegradable linkages to backbone moieties:

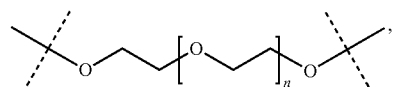

wherein n is an integer of from 5 to 50.

Preferably, the hydrogel carrier is composed of backbone moieties interconnected by hydrolytically degradable bonds.

More preferably, the backbone moieties comprise a branching core of the following formula:

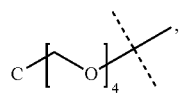

wherein the dashed line indicates attachment to the remainder of the backbone moiety.

More preferably, the backbone moieties comprise a structure of the following formula:

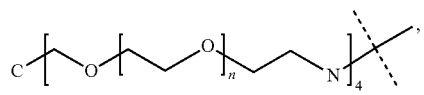

wherein n is an integer of from 5 to 50 and the dashed line indicates attachment to the remainder of the backbone moiety.

Preferably, backbone moiety comprises a hyperbranched moiety Hyp.

More preferably, the backbone moiety comprises a hyperbranched moiety Hyp of the following formula:

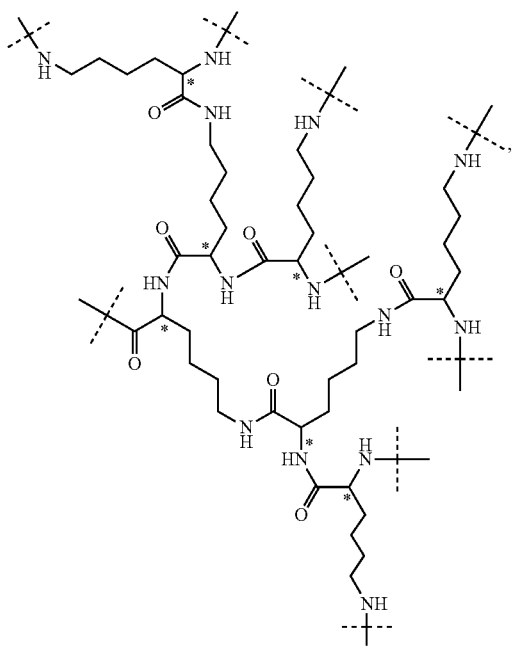

wherein the dashed lines indicate attachment to the rest of the molecule and carbon atoms marked with asterisks indicate S-configuration.

Preferably, the backbone moieties are attached to at least one spacer of the following formula:

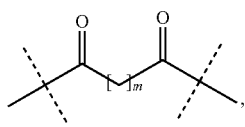

wherein one of the dashed lines indicates attachment to the hyperbranched moiety Hyp and the second dashed line indicates attachment to the rest of the molecule; and wherein m is an integer of from 2 to 4.

Preferably, the backbone moieties are linked together through crosslinker moieties having the following structure

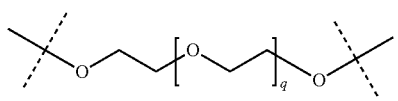

wherein
q is an integer from 3 to 100, preferably from 5 to 50.

In hydrogel prodrugs of the invention, the hydrolysis rate of the biodegradable bonds between backbone moieties and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable hydrogel carrier according to the invention.

Preferably, $L^2$ is attached to Z through a thiosuccinimide group which in turn is attached to the hydrogel's backbone moiety through a spacer, such as an oligoethylene glycol chain. Preferably, the linkage of this spacer chain to the backbone moiety is a permanent bond, preferably an amide bond.

Biodegradability of the hydrogels according to the present invention is achieved by introduction of hydrolytically degradable bonds.

For interconnected functional groups, the term "hydrolytically degradable" refers within the context of the present invention to linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are carboxylic esters, carbonates, phosphoesters and sulfonic acid esters and most preferred are carboxylic esters or carbonates. It is understood that for in vitro studies accelerated conditions like, for example, pH 9, 37° C., aqueous buffer, may be used for practical purposes.

Permanent linkages are non-enzymatically hydrolytically degradable under physiological conditions (aqueous buffer at pH 7.4, 37° C.) with half-lives of six months or longer, such as, for example, amides.

The degradation of the biodegradable hydrogel carrier according to the invention is a multi-step reaction where a multitude of degradable bonds is cleaved resulting in degradation products which may be water-soluble or water-insoluble. However, water-insoluble degradation products may further comprise degradable bonds so that they can be cleaved in that water-soluble degradation products are obtained. These water-soluble degradation products may comprise one or more backbone moieties. It is understood that released backbone moieties may, for instance, be permanently conjugated to spacer or blocking or linker groups or affinity groups and/or prodrug linker degradation products and that also water-soluble degradation products may comprise degradable bonds.

The structures of the branching core, PEG-based polymeric chains, hyperbranched dendritic moieties and moieties attached to the hyperbranched dendritic moieties can be inferred from the corresponding descriptions provided in the sections covering the hydrogel carriers of the present invention. It is understood that the structure of a degradant depends on the type of hydrogel according to the invention undergoing degradation.

The total amount of backbone moieties can be measured in solution after complete degradation of the hydrogel according to the invention, and during degradation, fractions of soluble backbone degradation products can be separated from the insoluble hydrogel according to the invention and can be quantified without interference from other soluble degradation products released from the hydrogel according to the invention. A hydrogel object according to the invention may be separated from excess water of buffer of physiological osmolality by sedimentation or centrifugation. Centrifugation may be performed in such way that the supernatant provides for at least 10% of the volume of the swollen hydrogel according to the invention. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods.

Preferably, water-soluble degradation products may be separated from water-insoluble degradation products by filtration through 0.45 μm filters, after which the water-soluble degradation products can be found in the flow-through.

Water-soluble degradation products may also be separated from water-insoluble degradation products by a combination of a centrifugation and a filtration step.

For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

In such hydrogel-linked insulin prodrugs according to the invention, it is desirable that almost all insulin release (>90%) has occurred before a significant amount of release of the backbone degradation products (<10%) has taken place. This can be achieved by adjusting the hydrogel-linked insulin prodrug's half-life versus the hydrogel degradation kinetics.

Preferably, are insulin prodrugs have the structure of formula (IIa) or (IIb)

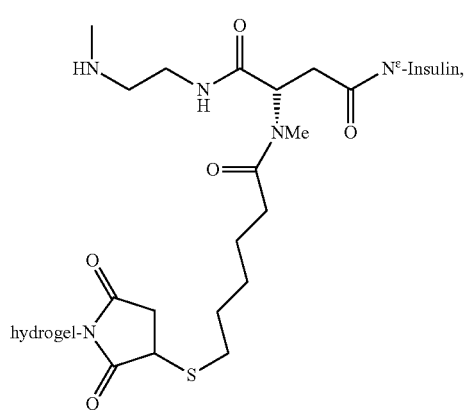
(IIa)

wherein $N^\epsilon$-Insulin refers to insulin connected via one lysine side chain; or

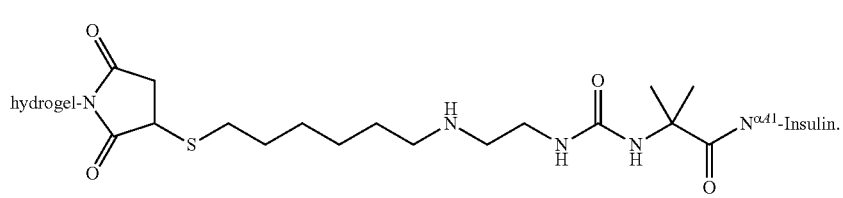
(IIb)

Preferably, the hydrogel in (IIa) or (IIb) is a biodegradable polyethylene glycol (PEG) based water-insoluble hydrogel.

Preferably, the hydrogel in (IIa) or (IIb) is composed of backbone moieties interconnected by hydrolytically degradable bonds.

More preferably, the backbone moieties comprise a branching core of the following formula:

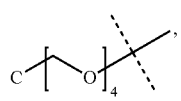

wherein the dashed line indicates attachment to the remainder of the backbone moiety.

More preferably, the backbone moieties comprise a structure of the following formula:

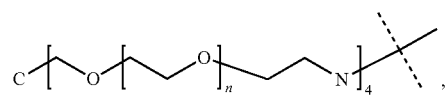

wherein n is an integer of from 5 to 50 and the dashed line indicates attachment to the rest of the molecule.

Preferably, backbone moiety comprises a hyperbranched moiety Hyp.

More preferably, the backbone moiety comprises a hyperbranched moiety Hyp of the following formula:

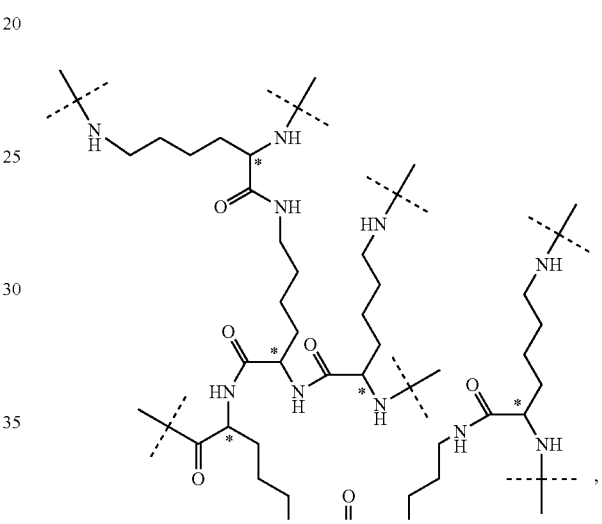

-continued

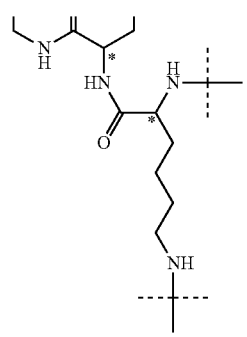

wherein the dashed lines indicate attachment to the rest of the molecule and carbon atoms marked with asterisks indicate S-configuration.

Preferably, the backbone moieties are attached to at least one spacer of the following formula:

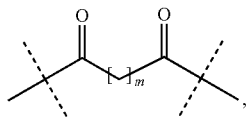

wherein one of the dashed lines indicates attachment to the hyperbranched moiety Hyp and the second dashed line indicates attachment to the rest of the molecule; and wherein m is an integer of from 2 to 4.

Preferably, the backbone moieties are attached to at least one spacer of the following formula:

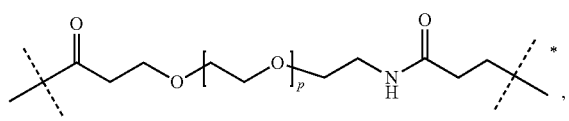

wherein the dashed line marked with the asterisk indicates the bond between the hydrogel and the N of the thiosuccinimide group,
wherein the other dashed line indicates attachment to Hyp, and
wherein p is an integer of from 0 to 10.

Preferably, the backbone moieties are linked together through crosslinker moieties having the following structure

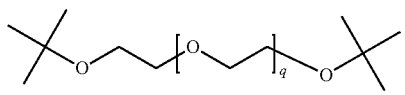

wherein
q is an integer from 3 to 100;

The hydrolysis rate of the biodegradable bonds between backbone and crosslinker moieties is determined by the number and type of connected atoms adjacent to the PEG-ester carboxy group. For instance by selecting from succinic, adipic or glutaric acid for PEG ester formation it is possible to vary the degradation half-lives of the crosslinker.

The hydrogel-linked insulin prodrug of the present invention can be prepared starting from the hydrogel of the present invention by convenient methods known in the art. It is clear to a practitioner in the art that several routes exist. For example the prodrug linker mentioned above to which the biologically active moiety is covalently attached can be reacted with the reactive functional groups of the hydrogel of the present invention with or with already bearing the active moiety in part or as whole.

In a preferable method of preparation, the hydrogel is generated through chemical ligation reactions. The hydrogel may be formed from two macromolecular educts with complementary functionalities which undergo a reaction such as a condensation or addition. One of these starting materials is a crosslinker reagent with at least two identical functional groups and the other starting material is a homomultifunctional backbone reagent. Suitable functional groups present on the crosslinker reagent include terminal amino, carboxylic acid and derivatives, maleimide and other alpha,beta unsaturated Michael acceptors like vinylsulfone, thiol, hydroxyl groups. Suitable functional groups present in the backbone reagent include but are not limited to amino, carboxylic acid and derivatives, maleimide and other alpha,beta unsaturated Michael acceptors like vinylsulfone, thiol, hydroxyl groups.

If the crosslinker reagent reactive functional groups are used substoichiometrically with respect to backbone reactive functional groups, the resulting hydrogel will be a reactive hydrogel with free reactive functional groups attached to the backbone structure.

Optionally, the prodrug linker may be first conjugated to insulin and the resulting insulin-prodrug linker conjugate may then react with the hydrogel's reactive functional groups. Alternatively, after activation of one of the functional groups of the prodrug linker, the linker-hydrogel conjugate may be contacted with insulin in the second reaction step and excess insulin may be removed by filtration after conjugation of the insulin to the hydrogel-bound prodrug linker.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably from 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or five lysines would be attached to each arm of a 8-arm PEG. In another embodiment, the multi-arm PEG derivative is a tetra- or octa carboxy PEG. In this case, the dendritic moieties may be generated from glutaric or aspartic acid, and the resulting backbone reagent would carry 32 carboxy groups. It is understood that all or a fraction of the backbone reagent's functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

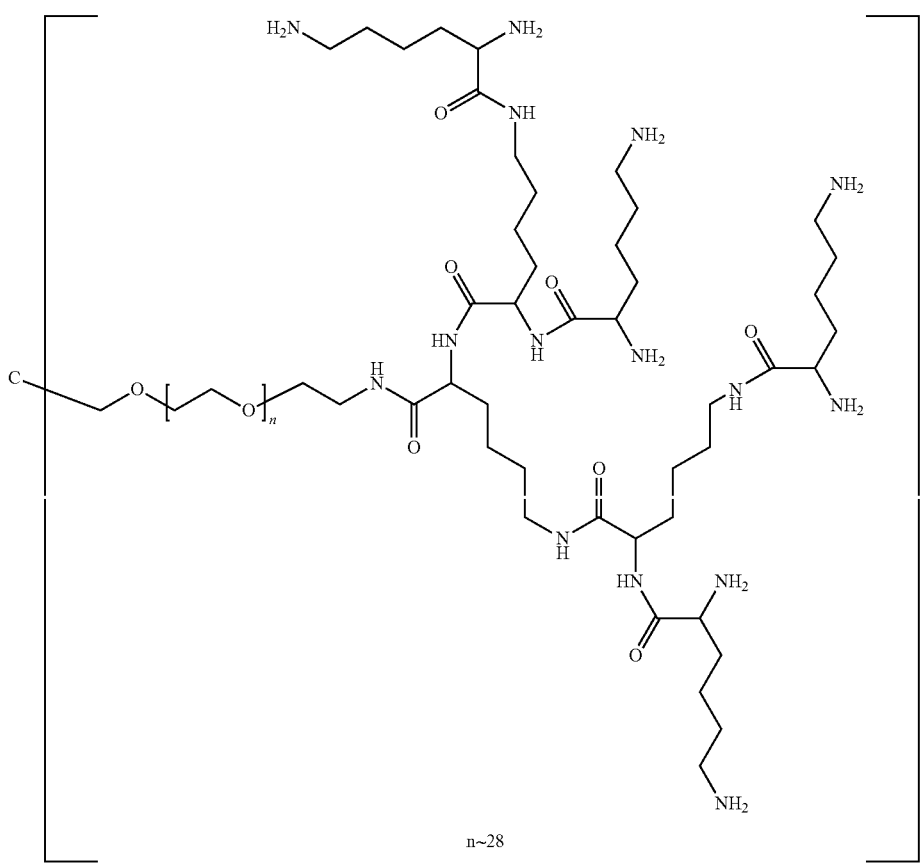

Synthesis of the crosslinker reagent starts from a linear PEG chain with a molecular weight ranging from 0.2 to 5 kDa, more preferably from 0.6 to 2 kDa, which is esterified with a half ester of a dicarboxylic acid, most adipic acid or glutaric acid. Preferred protecting group for half ester formation is the benzylic group. The resulting bis dicarboxylic acid PEG half esters are converted into more reactive carboxy compounds such as acyl chlorides or active esters, eg pentafluorophenyl or N-hydroxysuccinimide esters, most preferred N-hydroxysuccinimde esters, of which preferred selected structure is shown below.

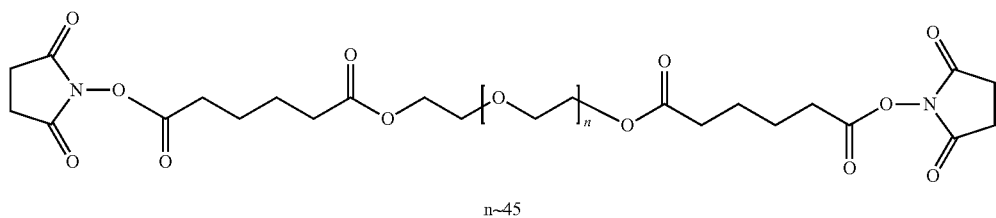

Alternatively, the bis dicarboxylic acid PEG half esters may be activated in the presence of a coupling agent such as DCC or HOBt or PyBOP.

In an alternative embodiment the backbone reagent carries carboxy groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker functional groups, backbone and crosslinker are dissolved in DMSO and a suitable emulgator with an appropriately selected HLB value, preferably Arlacel P135, is employed to form an inverse emulsion using a mechanical stirrer and controlling the stirring speed. Polymerization is initiated by the addition of a suitable base, preferably by N,N,N',N'-tetramethylethylene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

Further, such hydrogel according to the invention may be functionalized with a spacer carrying a different reactive functional group than provided by the hydrogel. For instance maleimide reactive functional groups may be introduced into the hydrogel by coupling a suitable heterobifunctional spacer such as Mal-PEG6-NHS to the hydrogel. Such functionalized hydrogel can be further conjugated to insulin-linker reagents, carrying a reactive thiol group on the linker moiety to form hydrogel-linked insulin prodrugs according to the present invention.

After loading the insulin-linker conjugate to the functionalized maleimido group-containing hydrogel, all remaining functional groups are capped with a suitable blocking reagent, such as mercaptoethanol, to prevent undesired side-reactions.

In a preferred embodiment of the invention, an insulin-linker conjugate carrying a free thiol group connected to the linker moiety, is reacted with a maleimide-functionalized hydrogel at temperatures between room temperature and 4° C., more preferred at room temperature, in a buffered aqueous solution of pH 2-5, preferably pH 2.5-4.5, more preferably pH 3.0-4.0. Subsequently, the corresponding resulting insulin-linker-hydrogel conjugate is treated with mercaptoethanol at temperatures between room temperature and 4° C., more preferred at room temperature, in a buffered aqueous solution of pH 2-5, preferably pH 2.5-4.0, more preferably pH 2.5-3.5. In another preferred embodiment of the invention, an insulin-linker conjugate carrying a maleimide group connected to the linker moiety, is reacted with a thiol-functionalized hydrogel at temperatures between room temperature and 4° C., more preferred at room temperature, in a buffered aqueous solution of pH 2-5, preferably pH 2.5-4.5, more preferably pH 3.0-4.0. Subsequently, the corresponding resulting insulin-linker-hydrogel conjugate is treated with a low molecular weight compound comprising a maleimide group, preferably a maleimide-containing compound of 100 to 300 Da, e.g. N-ethyl-maleimide, at temperatures between room temperature and 4° C., more preferred at room temperature, in a buffered aqueous solution of pH 2-5, preferably pH 2.5-4.0, more preferably pH 2.5-3.5.

Another aspect of the present invention is a process comprising the steps of
  (a) contacting an aqueous suspension comprising maleimide-functionalized hydrogel microparticles with a solution comprising an insulin-linker reagent carrying thiol groups at temperatures between room temperature and 4° C. in a buffered aqueous solution of pH 2-5, resulting in an insulin-linker-hydrogel conjugate;
  (b) optionally, treating the insulin-linker-hydrogel conjugate from step (a) with a thiol-containing compound of 34 Da to 500 Da at temperatures between room temperature and 4° C. in a buffered aqueous solution of pH 2-5.

Another aspect of the present invention is a process comprising the steps of
  (a) contacting an aqueous suspension comprising thiol-functionalized hydrogel microparticles with a solution comprising an insulin-linker reagent carrying maleimide groups at temperatures between room temperature and 4° C. in a buffered aqueous solution of pH 2-5, resulting in an insulin-linker-hydrogel conjugate;
  (b) optionally, treating the insulin-linker-hydrogel conjugate from step (a) with a maleimide-containing compound of 100 to 300 Da at temperatures between room temperature and 4° C. in a buffered aqueous solution of pH 2-5.

A particularly preferred method for the preparation of a prodrug of the present invention comprises the steps of
  (a) reacting a compound of formula $C(A'-X^1)_4$, wherein $A'-X^1$ represents A before its binding to Hyp or a precursor of Hyp and $X^1$ is a suitable functional group, with a compound of formula $Hyp'-X^2$, wherein $Hyp'-X^2$ represents Hyp before its binding to A or a precursor of Hyp and $X^2$ is a suitable functional group to react with $X^1$;
  (b) optionally reacting the resulting compound from step (a) in one or more further steps to yield a compound of formula $C(A-Hyp)_4$ having at least four functional groups;
  (c) reacting the at least four functional groups of the resulting compound from step (b) with a polyethyleneglycol based crosslinker precursor, wherein the active ester groups of the crosslinker precursor are used in a sub-stoichiometric amount compared to the total number of reactive functional groups of $C(A-Hyp)_4$ to yield a hydrogel;
  (d) reacting remaining un-reacted functional groups (representing the reactive functional groups of the backbone comprised in the hydrogel) in the hydrogel backbone of step (c) with a covalent conjugate of biologically active moiety and transient prodrug linker or first reacting the un-reacted functional groups with the transient prodrug linker and subsequently with the biologically active moiety;
  (e) optionally capping remaining un-reacted functional groups to yield a prodrug of the present invention.

Specifically, hydrogels for the insulin prodrugs of the present invention are synthesized as follows:

For bulk polymerization, backbone reagent and crosslinker reagent are mixed in a ratio amine/active ester of 2:1 to 1.05:1.

Both backbone reagent and crosslinker reagent are dissolved in DMSO to give a solution with a concentration of 5 to 50 g per 100 mL, preferably 7.5 to 20 g per 100 ml and most preferably 10 to 20 g per 100 ml.

To effect polymerization, 2 to 10% (vol.) N,N,N',N'-tetramethylethylene diamine (TMEDA) are added to the DMSO solution containing crosslinker reagent and backbone reagent and the mixture is shaken for 1 to 20 sec and left standing. The mixture solidifies within less than 1 min.

Such hydrogel according to the invention is preferably comminuted by mechanical processes such as stirring, crushing, cutting pressing, or milling, and optionally sieving.

For emulsion polymerization, the reaction mixture is comprised of the dispersed phase and the continuous phase.

For the dispersed phase, backbone reagent and crosslinker reagent are mixed in a ratio amine/active ester of 2:1 to 1.05:1 and are dissolved in DMSO to give a to give a solution with a concentration of 5 to 50 g per 100 mL, preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per mL dispersed phase, more preferably 5 to 20 mg per mL dispersed phase, most preferably 10 mg per mL dispersed phase.

The emulsifier has an HLB-value of 3 to 8. Preferably, the emulsifier is a triester of sorbitol and a fatty acid or an poly(hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, Cithrol DPHS (Cithrol DPHS, former Arlacel P135, Croda International Plc).

Droplets of the dispersed phase are generated by stirring with an axial flow impeller with a geometry similar to stirrers such as Isojet, Intermig, Propeller (EKATO Rühr- and Mischtechnik GmbH, Germany)), most preferably similar to Isojet with a diameter of 50 to 90% of the reactor diameter. Preferably, stirring is initated before addition of the dispersed phase. Stirrer speed is set to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N,N',N'-tertramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 µm and a 32 µM deck to give hydrogel microparticles according to the invention.

Another aspect of the present invention are insulin-linker conjugates of formula (IIIa) and (IIIb)

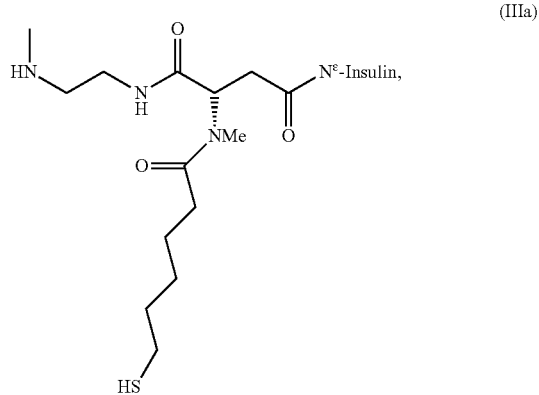

(IIIa)

wherein $N^\epsilon$-Insulin refers to insulin connected via one lysine side chain; and

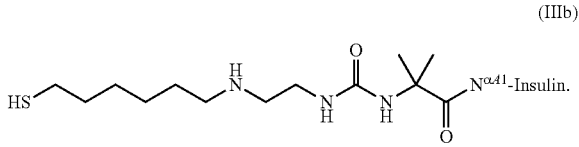

(IIIb)

Another aspect of the present invention are insulin-linker reagents D-L*, wherein
D represents an insulin moiety; and
L* is a non-biologically active linker reagent represented by formula (IV),

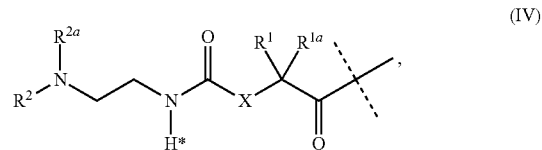

(IV)

wherein the dashed line indicates the attachment to one of the amino groups of the insulin by forming an amide bond;

X is $C(R^3R^{3a})$; or $N(R^3)$;

$R^{1a}$, $R^{3a}$ are independently selected from the group consisting H, $NH(R^{2b})$, $N(R^{2b})C(O)R^4$ tom and $C_{1-4}$ alkyl;

$R^1$, $R^2$ $R^{2a}$, $R^{2b}$, $R^3$, $R^4$ are independently selected from the group consisting of H and $C_{1-4}$ alkyl, wherein L* is substituted with one $L^{2*}$ and optionally further substituted, provided that the hydrogen marked with the asterisk in formula (IV) is not replaced by a substituent and wherein $L^{2*}$ is a spacer connected to L* and comprising a chemical functional group intended for conjugation to a reactive biodegradable hydrogel;

Preferably, $R^2$ in formula (IV) is replaced by $L^{2*}$.
Preferably, $R^1$ in formula (IV) is replaced by $L^{2*}$.
Preferably, X in formula (IV) is $N(R^3)$.
More preferably, X in formula (IV) is $C(R^3R^{3a})$ and $R^{3a}$ is $N(R^{2b})C(O)R^4$.
More preferably, X in formula (IV) is $C(R^3R^{3a})$ and $R^{3a}$ is replaced by $L^{2*}$.
Even more preferably, X in formula (IV) is $C(R^3R^{3a})$, $R^{1a}$ is $N(R^{2b})$-$L^{2*}$.
Preferably, L* in formula (IV) is not further substituted.
Preferably, $L^{2*}$ in formula (IV) comprises a thiol group.
Preferably, $L^{2*}$ in formula (IV) comprises a maleimide group.

The hydrogel for the prodrug of the present invention can be obtained from the preparation methods in form of microparticles. In a preferred embodiment of the invention, the reactive hydrogel is a shaped article such as a mesh or a stent. Most preferably, the hydrogel is formed into microparticulate beads which can be administered as subcutaneous or intramuscular injection by means of a standard syringe. Such soft beads may have a diameter of between 1 and 500 micrometer.

Preferably, the microparticles have a diameter of between 10 and 100 micrometer if suspended in an isotonic aqueous formulation buffer, most preferably a diameter of between 20 and 100 micrometer, most preferably a diameter of between 25 and 80 micrometer.

Preferably, the microparticles can be administered by injection through a needle smaller than 0.6 mm inner diameter, preferably through a needle smaller than 0.3 mm inner diameter, more preferably through a needle smaller than 0.225 mm inner diameter, even more preferably through a needle smaller than 0.175 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the biodegradable hydrogel according to the invention swollen in a liquid at a certain concentration (w/v) and at a certain temperature, a needle of a given inner diameter connected to the outlet of such syringe, and the time required to extrude a certain volume of the biodegradable hydrogel according to the invention from the syringe through the needle.

In order to provide for injectability, a volume of 1 mL of the insulin prodrugs according to the invention swollen in water to a concentration of at least 5% (w/v) and contained in a syringe holding a plunger of a diameter of 4.7 mm can be extruded at room temperature within 10 seconds by applying a force of less than 50 Newton.

Preferably injectability is achieved for an insulin prodrug according to the invention swollen in water to a concentration of ca. 10% (w/v).

Furthermore a one-step process is provided to selectively acylate single free ε-amino groups found in the B-chain of insulin and its analoga with an acylating agent containing a protected thiol or other functional group. For recombinant human insulin, insulin glargine and insuline aspart the site of acylation is the ε-amino group of LysB29, in the case of insulin Lispro the site of acylation is the ε-amino group of LysB28, and in the case of insulin glulisine the site of acylation is the ε-amino group of LysB3. It is understood that this process is not limited to the before-mentioned insulin and insulin analoga, but can be applied to other insulin analoga as long as they contain ε-amino groups and the person skilled in the art will be able to identify the corresponding lysine residue suitable for acylation.

Thus another aspect of the present invention is a process for acylating the ε-amino group of insulin or an insulin analog, having one or more free α-amino groups and the free ε-amino group with an acylating agent containing one or more protected functional groups, which comprises reacting the insulin or insulin analog with a soluble acylating agent containing one or more protected functional groups at a pH of 8.0 to below 9.0 in a polar solvent. It is understood that only such protective groups are to be used that are stable in the before mentioned conditions.

The reaction is carried out by reacting an acylating agent, such as a linker reagent, which contains one or more protected functional groups, with the ε-amino group of the insulin or insulin analog under basic conditions with a pH ranging from about 8.00 to below 9.0, preferably, from 8.0 to 8.9, more preferably, from 8.3 to 8.7 in a polar solvent, such as aqueous mixtures of, for example, methanol, ethanol, propanol, isopropanol, DMSO, DMF, NMP, dimethylacetamid, acetonitrile.

Another aspect of the present invention is an insulin compound characterized by having an acyl group linked to the ε-nitrogen of insulin or an insulin analog and wherein such acyl group has one or more protected functional groups.

Another aspect of the present invention is a pharmaceutical composition comprising a prodrug of the present invention or a pharmaceutically acceptable salt thereof together with a pharmaceutically acceptable excipient. The pharmaceutical composition is further described in the following paragraphs.

The composition of insulin-hydrogel prodrug may be provided as a suspension composition or as a dry composition. Preferably, the pharmaceutical composition of insulin-hydrogel prodrug is a dry composition. Suitable methods of drying are, for example, spray-drying and lyophilization (freeze-drying). Preferably, the pharmaceutical composition of insulin-hydrogel prodrug is dried by lyophilization.

Preferably, the insulin hydrogel prodrug is sufficiently dosed in the composition to provide therapeutically effective amount of insulin for at least three days in one application. More preferably, one application of the insulin hydrogel prodrug is sufficient for one week.

The pharmaceutical composition of insulin-hydrogel prodrug according to the present invention contains one or more excipients.

Excipients used in parenteral compositions may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The compositions of insulin-hydrogel prodrugs according to the present invention contain one or more than one excipient, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum (iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride (iv) Stabilizers: Stabilisation is achieved by strengthening of the protein-stabilising forces, by destabilisation of the denatured stater, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used (v) Anti-adsorption agents: Mainly ionic or inon-ionic surfactants or other proteins or soluble polymers are used to coat or adsorb competitively to the inner surface of the composition's or composition's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Lyo- and/or cryoprotectants: During freeze- or spray drying, excipients may counteract the destabilising effects caused by hydrogen bond breaking and water removal. For this purpose sugars and polyols may be used but corresponding positive effects have also been observed for surfactants, amino acids, non-aqueous solvents, and other peptides. Trehalose is particulary efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid (viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a tri-block of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(x) Other auxiliary agents: such as wetting agents, viscosity modifiers, antibiotics, hyaluronidase.

Acids and bases such as hydrochloric acid and sodium hydroxide are auxiliary agents necessary for pH adjustment during manufacture.

Preferably, the composition of insulin-hydrogel prodrug contains one or more than one viscosifier and/or viscosity modifying agent.

The term "excipient" preferably refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the therapeutic, preferably in purified form, together with a suitable amount of excipient so as to provide the form for proper administration to the patient. The formulation should suit the mode of administration.

In a general embodiment a pharmaceutical composition of the present invention whether in dry form or as a suspension or in another form may be provided as single or multiple dose composition.

In one embodiment of the present invention, the dry composition of insulin-hydrogel prodrug is provided as a single dose, meaning that the container in which it is supplied contains one pharmaceutical dose.

Thus in another aspect of the present invention the composition is provided as a single dose composition.

Preferably, the suspension composition is a multiple dose composition, meaning that it contains more than one therapeutic dose. Preferably, a multiple dose composition contains at least 2 doses. Such multiple dose composition of insulin-hydrogel can either be used for different patients in need thereof or is intendend for use in one patient, wherein the remaining doses are stored after the application of the first dose until needed.

In another aspect of the present invention the composition is comprised in a container. Preferably the container is a dual-chamber syringe. Especially the dry composition according to the present invention is provided in a first chamber of the dual-chamber syringe and reconstitution solution is provided in a second chamber of the dual-chamber syringe.

Prior to applying the dry composition of insulin-hydrogel prodrug to a patient in need thereof, the dry composition is reconstituted. Reconstitution can take place in the container in which the dry composition of insulin-hydrogel prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials. If the insulin-hydrogel prodrug composition is provided as single dose, the reconstituion solution may contain one or more preservative and/or antimicrobial. Preferably, the reconstitution solution is sterile water. If the composition of insulin-hydrogel prodrug is a multiple dose composition, it is prefered that the reconstitution solution contains one or more preservative and/or antimicrobial, such as, for example, benzylalcohol and cresol.

An additional aspect of the present invention relates to the method of administration of a reconstituted insulin hydrogel prodrug composition. The insulin hydrogel prodrug composition can be administered by methods of injection or infusion, including intradermal, subcutaneous, intramuscular, intravenous, intraosseous, and intraperitoneal.

A further aspect is a method of preparing a reconstituted composition comprising a therapeutically effective amount of an insulin hydrogel prodrug, and optionally one or more pharmaceutically acceptable excipients, wherein the insulin is transiently linked to a hydrogel, the method comprising the step of
  contacting the composition of the present invention with a reconstitution solution.

Another aspect is a reconstituted composition comprising a therapeutically effective amount of a insulin hydrogel prodrug, and optionally one or more pharmaceutically acceptable excipients, wherein the insulin is transiently linked to a hydrogel obtainable by the method above.

Another aspect of the present invention is the method of manufacturing a dry composition of insulin-hydrogel prodrug. In one embodiment, such suspension composition is made by
  (i) admixing the insulin-hydrogel prodrug with one or more excipients,
  (ii) transferring amounts equivalent to single or multiple doses into a suitable container,
  (iii) drying the composition in said container, and
  (iv) sealing the container.

Suitable containers are vials, syringes, dual-chamber syringes, ampoules, and cartridges.

Another aspect is a kit of parts. When the administration device is simply a hypodermic syringe then the kit may comprise the syringe, a needle and a container comprising the dry insulin-hydrogel prodrug composition for use with the syringe and a second container comprising the reconstitution solution. In more preferred embodiments, the injection device is other than a simple hypodermic syringe and so the separate container with reconstituted insulin-hydrogel prodrug is adapted to engage with the injection device such that in use the liquid composition in the container is in fluid connection with the outlet of the injection device. Examples of administration devices include but are not limited to hypodermic syringes and pen injector devices. Particularly preferred injection devices are the pen injectors in which case the container is a cartridge, preferably a disposable cartridge.

A preferred kit of parts comprises a needle and a container containing the composition according to the present invention and optionally further containing a reconstitution solution, the container being adapted for use with the needle. Preferably, the container is a dual-chamber syringe.

In another aspect, the invention provides a cartridge containing a composition of insulin-hydrogel prodrug as hereinbefore described for use with a pen injector device. The cartridge may contain a single dose or multiplicity of doses of insulin.

In one embodiment of the present invention the suspension composition of insulin-hydrogel prodrug does not only comprise an insulin-hydrogel prodrug and one or more than one excipients, but also other biologically active agents, either in their free form or as prodrugs. Preferably, such additional one or more biologically active agent is a prodrug, more preferably a hydrogel prodrug. Such biologically active agents include, but are not limited to, compounds of the following classes:
  (i) Sulfonylureas, such as, for example, chlorpropamide, tolazamide, tolbutamide, glyburide, glipizide, glimepiride, and the like,
  (ii) Meglitinides, such as, for example, repaglinide,
  (iii) Glucagon-like Peptide-1(GLP-1) and it's mimetics, Glucose-insulinotropic peptide (GIP) and it's mimetics, Exendin and it's mimetics, and Dipeptyl Protease Inhibitors (DPPIV),
  (iv) Biguanides, such as, for example, metformin,
  (v) Thiazolidinediones, such as, for example, rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, and the like
  (vi) GW2570, and the like,
  (vii) Retinoid-X receptor (RXR) modulators, such as, for example, targretin, 9-cis-retinoic acid, and the like,
  (viii) Other insulin sensitizing agents, such as, for example, INS-1, PTP-1B inhibitors, GSK3 inhibitors, glycogen phosphorylase a inhibitors, fructose-1,6-bisphosphatase inhibitors, and the like,
  (ix) Insulins, including regular or short-acting, intermediate-acting, and long-acting insulins, inhaled insulin and insulin analogues, such as insulin molecules with minor differences in the natural amino acid sequence
  (x) Small molecule mimics of insulin, including, but not limited to L-783281, TE-17411, and the like,
  (xi) Na-glucose co-transporter inhibitors, such as T-1095, T-1095A, phlorizen, and the like,
  (xii) Amylin agonists which include, but are not limited to pramlintide, and the like,
  (xiii) Glucagon antagonists such as AY-279955, and the like.

In addition to antidiabetic agents, bioactive compounds may be anti-obesity agents such as orlistat, a pancreatic lipase inhibitor, which prevents the breakdown and absorption of fat; or sibutramine, an appetite suppressant and inhibitor of the reuptake of serotonin, norepinephrine and dopamine in the brain, growth factors increasing fat mobilization (eg, growth hormone, IGF-1, growth hormone releasing factor), oxyntomodulin and ghrelin modulators. Other potential bioactive anti-obesity agents include, but are not limited to, appetite-suppressants acting through adrenergic mechanisms such as benzphetamine, phenmetrazine, phentermine, diethylpropion, mazindol, sibutramine, phenylpropanolamine or, ephedrine; appetite-suppressant agents acting through serotonergic mechanisms such as quipazine, fluoxetine, sertraline, fenfluramine, or dexfenfluramine; appetite-suppressant agents acting through dopamine mechanisms, eg, apomorphine; appetite-suppressant agents acting through histaminergic mechanisms (eg, histamine mimetics, H3 receptor modulators); enhancers of energy expenditure such as beta-3 adrenergic agonists and stimulators of uncoupling protein function; leptin and leptin mimetics (eg, meterleptin); neuropeptide Y antagonists; melanocortin-1, 3 and 4 receptor modulators; cholecystokinin agonists; glucagon-like peptide-1 (GLP-1) mimetics and analogues (eg, Exendin); androgens (eg, dehydroepiandrosterone and derivatives such as etiocholandione), testosterone, anabolic steroids (eg, oxandrolone), and steroidal hormones; galanin receptor antagonists; cytokine agents such as ciliary neurotrophic factor; amylase inhibitors; enterostatin agonists/mimetics; orexin/ hypocretin antagonists; urocortin antagonists; bombesin agonists; modulators of protein kinase A; corticotropin-releasing factor mimetics; cocaine- and amphetamine-regulated transcript mimetics; calcitonin-gene related peptide mimetics; and fatty acid synthase inhibitors.

In an alternative embodiment, the insulin-hydrogel prodrug composition according to the present invention is combined with a second biologically active compound in such way that the insulin-hydrogel prodrug is administered to a patient in need thereof first, followed by the administration of the second compound. Alternatively, the insulin-hydrogel composition is administered to a patient in need thereof after another compound has been administered to the same patient.

Yet another aspect of the present invention is a prodrug of the present invention or a pharmaceutical composition of the present invention for use as a medicament.

Yet another aspect of the present invention is a prodrug of the present invention or a pharmaceutical composition of the present invention for use in a method of treating or preventing diseases or disorders which can be treated by insulin.

Such diseases or disorders are e.g. hyperglycemia, pre-diabetes, impaired glucose tolerance, diabetes type I, diabetes type II, syndrome X, obesity, hypertension.

Patients in need of treatment with the long acting insulin compositions described in the present invention are at high risk of developing comorbidities. Accordingly, the combination of the long acting insulin of the present with appropriate bioactive compounds may be used, e.g., for the prevention, delay of progression or treatment of diseases and disorders selected from the group consisting of hypertension (including but not limited to isolated systolic hypertension and familial dyslipidemic hypertension), congestive heart failure, left ventricular hypertrophy, peripheral arterial disease, diabetic retinopathy, macular degeneration, cataract, diabetic nephropathy, glomerulosclerosis, chronic renal failure, diabetic neuropathy, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertriglyceridemia insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

Prevention, delay of progression or treatment of diseases and disorders selected from the group above can be achieved by combination of the long acting insulin composition of the present invention with at least one bioactive compound selected from the drug classes used for treating said conditions, including $AT_1$ receptor antagonists; angiotensin converting enzyme (ACE) inhibitors; renin inhibitors; beta adrenergic receptor blockers; alpha adrenergic receptor blockers; calcium channel blockers; aldosterone synthase inhibitors; aldosterone receptor antagonists; neutral endopeptidase (NEP) inhibitors; dual angiotensin converting enzyme/neutral endopetidase (ACE/NEP) inhibitors; an endothelin receptor antagonists; diuretics; statins; nitrates; anti clotting agents; natriuretic peptides; digitalis compounds; PPAR modulators.

In case the biologically active agents; prodrugs, especially hydrogel prodrugs contain one or more acidic or basic groups, the invention also comprises their corresponding pharmaceutically or toxicologically acceptable salts, in particular their pharmaceutically utilizable salts. Thus, the prodrugs which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the prodrugs simultaneously contain acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

Yet another aspect of the present invention is a method of treating, controlling, delaying or preventing in a mammalian patient, preferably in a human, in need of the treatment of one or more conditions comprising administering to said patient a therapeutically effective amount of a prodrug of the present invention or a pharmaceutical composition of the present invention or a pharmaceutically acceptable salt thereof.

EXAMPLES

Materials and Methods

Recombinant human insulin was obtained from Biocon Ltd., Bangalore, India.

Amino 4-arm PEG 5 kDa was obtained from JenKem Technology, Beijing, P. R. China.

N-(3-maleimidopropyl)-21-amino-4,7,10,13,16,19-hexaoxa-heneicosanoic acid NHS ester (Mal-PEG6-NHS) was obtained from Celares GmbH, Berlin, Germany.

2-Chlorotrityl chloride resin, HATU, N-cyclohexyl-carbodiimide-N'-methyl polystyrene, and amino acids were from Merck Biosciences GmbH, Schwalbach/Ts, Germany, if not stated otherwise. Fmoc(NMe)-Asp(OtBu)-OH was obtained from Bachem AG, Bubendorf, Switzerland. S-Trityl-6-mercaptohexanoic acid was purchased from Polypeptide, Strasbourg, France. Amino acids used were of L configuration if not stated otherwise.

All other chemicals were from Sigma-ALDRICH Chemie GmbH, Taufkirchen, Germany.

Solid phase synthesis was performed on 2-Chlorotrityl chloride (TCP) resin with a loading of 1.3 mmol/g. Syringes equipped with polypropylene frits were used as reaction vessels.

Loading of the first amino acid to resins was performed according to manufacturer's instructions.

Fmoc deprotection:

For Fmoc protecting-group removal, the resin was agitated with 2/2/96 (v/v/v) piperidine/DBU/DMF (two times, 10 min each) and washed with DMF (ten times).

Fmoc deprotection of Fmoc-Aib-loaded resins Fmoc deprotection of immobilized Fmoc-Aib-OH was achieved by stirring the resin in DMF/piperidine 4/1 (v/v) at 50° C. for 20 min (2 times).

Cleavage Protocol for 2-Chlorotrityl Chloride Resin:

Upon completed synthesis, the resin was washed with DCM, dried in vacuo and treated two times for 30 minutes with 6/4 (v/v) DCM/HFIP. Eluates were combined, volatiles were removed under a stream of nitrogen and the resulting crude product was purified by RP-HPLC. HPLC fractions containing product were combined and lyophilized.

Amine containing products obtained as TFA salts were converted to the corresponding HCl salts using ion exchange resin (Discovery DSC-SAX, Supelco, USA). This step was performed in case the residual TFA was expected to interfere with e.g. a subsequent coupling reaction.

RP-HPLC purification:

RP-HPLC was done on a 100×20 mm or 100×40 mm C18 ReproSil-Pur 300 ODS-3 5μ column (Dr. Maisch, Ammerbuch, Germany) connected to a Waters 600 HPLC System and Waters 2487 Absorbance detector. Linear gradients of solution A (0.1% TFA in $H_2O$) and solution B (0.1% TFA in acetonitrile) were used. HPLC fractions containing product were lyophilized.

Flash Chromatography

Flash chromatography purifications were performed on an Isolera One system from Biotage AB, Sweden, using Biotage KP-Sil silica cartridges and n-heptane and ethyl acetate as eluents. Products were detected at 254 nm.

For hydrogel beads, syringes equipped with polypropylene frits were used as reaction vessels or for washing steps.

Analytical Methods

Analytical ultra-performance LC (UPLC) was performed on a Waters Acquity system equipped with a Waters BEH300 C18 column (2.1×50 mm, 1.7 μm particle size) coupled to a LTQ Orbitrap Discovery mass spectrometer from Thermo Scientific.

MS of PEG products showed a series of $(CH_2CH_2O)_n$ moieties due to polydispersity of PEG staring materials. For easier interpretation only one single representative m/z signal is given in the examples. MS of insulin conjugates are reported for representative isotopes and refer to the four-proton adducts $[M+4H]^{4+}$.

Size exclusion chromatography (SEC) was performed using an Amersham Bioscience AEKTAbasic system equipped with a Superdex200 5/150 GL column (Amersham Bioscience/GE Healthcare) equipped with a 0.45 μm inlet filter, if not stated otherwise. 20 mM sodium phosphate, 140 mM NaCl, pH 7.4, was used as mobile phase.

Example 1

Synthesis of Backbone Reagent 1g

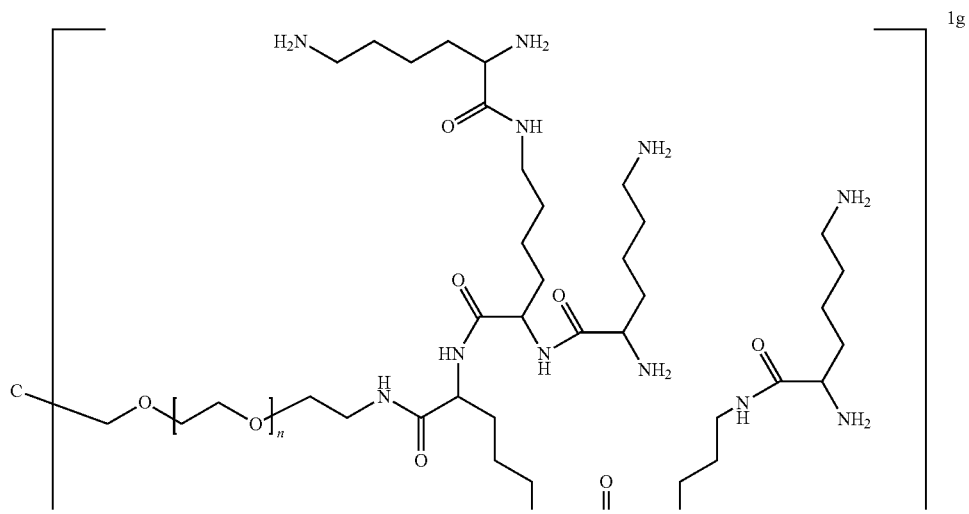

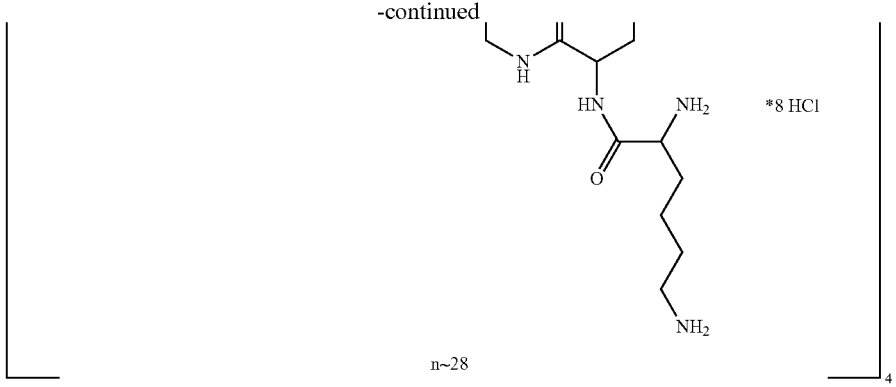

Backbone reagent 1g was synthesized from amino 4-arm PEG5000 1a according to following scheme:

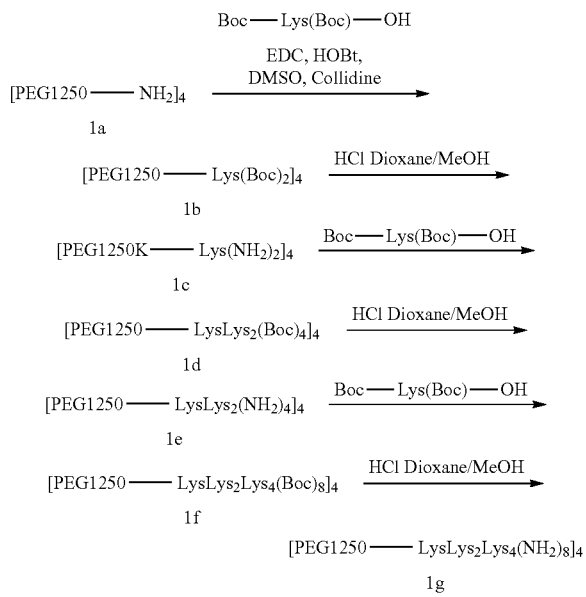

For synthesis of compound 1b, amino 4-arm PEG5000 1a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC HCl (1.15 g, 6.00 mmol), HOBt·H$_2$O (0.96 g, 6.25 mmol), and collidine (5.20 mL, 40 mmol) were added. The reaction mixture was stirred for 30 min at RT.

The reaction mixture was diluted with 1200 mL of dichloromethane and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 1b as colorless oil. Compound 1b was purified by RP-HPLC.

Yield 3.85 g (59%) colorless glassy product 1b.

MS: m/z 1294.4=[M+5H]$^{5+}$ (calculated=1294.6).

Compound 1c was obtained by stirring of 3.40 g of compound 1b (0.521 mmol) in 5 mL of methanol and 9 mL of 4 N HCl in dioxane at RT for 15 min. Volatiles were removed in vacuo. The product was used in the the next step without further purification.

MS: m/z 1151.9=[M+5H]$^{5+}$ (calculated=1152.0).

For synthesis of compound 1d, 3.26 g of compound 1c (0.54 mmol) were dissolved in 15 mL of DMSO (anhydrous). 2.99 g Boc-Lys(Boc)-OH (8.64 mmol) in 15 mL DMSO (anhydrous), 1.55 g EDC HCl (8.1 mmol), 1.24 g HOBt·H$_2$O (8.1 mmol), and 5.62 mL of collidine (43 mmol) were added. The reaction mixture was stirred for 30 min at RT.

Reaction mixture was diluted with 800 ml DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried with Na$_2$SO$_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 1d, which was used in the next step without further purification.

MS: m/z 1405.4=[M+6H]$^{6+}$ (calculated=1405.4).

Compound 1e was obtained by stirring a solution of compound 1d (3.96 g, 0.47 mmol) in 7 mL of methanol and 20 mL of 4 N HCl in dioxane at RT for 15 min. Volatiles were removed in vacuo. The product was used in the next step without further purification.

MS: m/z 969.6=[M+7H]$^{1+}$ (calculated=969.7).

For the synthesis of compound 1f, compound 1e (3.55 g, 0.48 mmol) was dissolved in 20 mL of DMSO (anhydrous). Boc-Lys(Boc)-OH (5.32 g, 15.4 mmol) in 18.8 ml of DMSO (anhydrous), EDC HCl (2.76 g, 14.4 mmol), HOBt·H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product 1f as colorless oil.

Product was dissolved in DCM and precipitated with cooled (−18° C.) diethylther. This step was repeated twice and the precipitate was dried in vacuo.

Yield 4.72 g (82%) colourless glassy product if which was used in the next step without further purification.

MS: m/z 1505.3=[M+8H]$^{8+}$ (calculated=1505.4).

Backbone reagent 1g was obtained by stirring a solution of compound 1f (MW ca 12035 g/mol, 4.72 g, 0.39 mmol) in 20 ml of methanol and 40 mL of 4 N HCl in dioxane at RT for 30 min. Volatiles were removed in vacuo.

Yield 3.91 g (100%), glassy product backbone reagent 1g.

MS: m/z 977.2=[M+9H]$^{9+}$ (calculated=977.4).

Alternative Synthetic Route for 1g

For synthesis of compound 1b, to a suspension of 4-Arm-PEG5000 tetraamine (1a) (50.0 g, 10.0 mmol) in 250 mL of iPrOH (anhydrous), boc-Lys(boc)-OSu (26.6 g, 60.0 mmol) and DIEA (20.9 mL, 120 mmol) were added at 45° C. and the mixture was stirred for 30 min.

Subsequently, n-propylamine (2.48 mL, 30.0 mmol) was added. After 5 min the solution was diluted with 1000 mL of MTBE and stored overnight at −20° C. without stirring. Approximately 500 mL of the supernatant were decanted off and discarded. 300 mL of cold MTBE were added and after 1 min shaking the product was collected by filtration through a glass filter and washed with 500 mL of cold MTBE. The product was dried in vacuo for 16 h.

Yield: 65.6 g (74%) 1b as a white lumpy solid
MS: m/z 937.4=$[M+7H]^{7+}$ (calculated=937.6).

Compound 1c was obtained by stirring of compound 1b from the previous step (48.8 g, 7.44 mmol) in 156 mL of 2-propanol at 40° C. A mixture of 196 mL of 2-propanol and 78.3 mL of acetylchloride was added under stirring within 1-2 min. The solution was stirred at 40° C. for 30 min and cooled to −30° C. overnight without stirring. 100 mL of cold MTBE were added, the suspension was shaken for 1 min and cooled for 1 h at −30° C. The product was collected by filtration through a glass filter and washed with 200 mL of cold MTBE. The product was dried in vacuo for 16 h.

Yield: 38.9 g (86%) 1c as a white powder
MS: m/z 960.1=$[M+6H]^{6+}$ (calculated=960.2).

For synthesis of compound 1d, to a suspension of 1c from the previous step (19.0 g, 3.14 mmol) in 80 ml 2-propanol boc-Lys(boc)-OSu (16.7 g, 37.7 mmol) and DIEA (13.1 mL, 75.4 mmol) were added at 45° C. and the mixture was stirred for 30 min at 45° C. Subsequently, n-propylamine (1.56 mL, 18.9 mmol) was added. After 5 min the solution was precipitated with 600 mL of cold MTBE and centrifuged (3000 $min^{-1}$, 1 min) The precipitate was dried in vacuo for 1 h and dissolved in 400 mL THF. 200 mL of diethyl ether were added and the product was cooled to −30° C. for 16 h without stirring. The suspension was filtered through a glass filter and washed with 300 mL cold MTBE. The product was dried in vacuo for 16 h.

Yield: 21.0 g (80%) 1d as a white solid
MS: m/z 1405.4=$[M+6H]^{6+}$ (calculated=1405.4).

Compound 1e was obtained by dissolving compound 1d from the previous step (15.6 g, 1.86 mmol) in in 3 N HCl in methanol (81 mL, 243 mmol) and stirring for 90 min at 40° C. 200 mL of MeOH and 700 mL of iPrOH were added and the mixture was stored for 2 h at −30° C. For completeness of crystallization, 100 mL of MTBE were added and the suspension was stored at −30° C. overnight. 250 mL of cold MTBE were added, the suspension was shaken for 1 min and filtered through a glass filter and washed with 100 mL of cold MTBE. The product was dried in vacuo.

Yield: 13.2 g (96%) 1e as a white powder
MS: m/z 679.1=$[M+10H]^{10+}$ (calculated=679.1).

For the synthesis of compound 1f, to a suspension of 1e from the previous step, (8.22 g, 1.12 mmol) in 165 ml 2-propanol boc-Lys(boc)-OSu (11.9 g, 26.8 mmol) and DIEA (9.34 mL, 53.6 mmol) were added at 45° C. and the mixture was stirred for 30 min. Subsequently, n-propylamine (1.47 mL, 17.9 mmol) was added. After 5 min the solution was cooled to −18° C. for 2 h, then 165 mL of cold MTBE were added, the suspension was shaken for 1 min and filtered through a glass filter. Subsequently, the filter cake was washed with 4× 200 mL of cold MTBE/iPrOH 4:1 and 1× 200 mL of cold MTBE. The product was dried in vacuo for 16 h.

Yield: 12.8 g, MW (90%) 1f as a pale yellow lumpy solid
MS: m/z 1505.3=$[M+8H]^{8+}$ (calculated=1505.4).

Backbone reagent 1g was obtained by dissolving 4Arm-PEG5kDa(-LysLys$_2$Lys$_4$(boc)$_8$)$_4$ (1f) (15.5 g, 1.29 mmol) in 30 mL of MeOH and cooling to 0° C. 4 N HCl in dioxane (120 mL, 480 mmol, cooled to 0° C.) was added within 3 min and the ice bath was removed. After 20 min, 3 N HCl in methanol (200 mL, 600 mmol, cooled to 0° C.) was added within 15 min and the solution was stirred for 10 min at room temperature. The product solution was precipitated with 480 mL of cold MTBE and centrifuged at 3000 rpm for 1 min. The precipitate was dried in vacuo for 1 h and redissolved in 90 mL of MeOH, precipitated with 240 mL of cold MTBE and the suspension was centrifuged at 3000 rpm for 1 min. The product 1g was dried in vacuo Yield: 11.5 g (89%) as pale yellow flakes.
MS: m/z 1104.9=$[M+8H]^{8+}$ (calculated=1104.9).

Example 2

Synthesis of Crosslinker Reagent 2d

Crosslinker reagent 2d was prepared from adipic acid mono benzyl ester (English, Arthur R. et al., *Journal of Medicinal Chemistry*, 1990, 33(1), 344-347) and PEG2000 according to the following scheme:

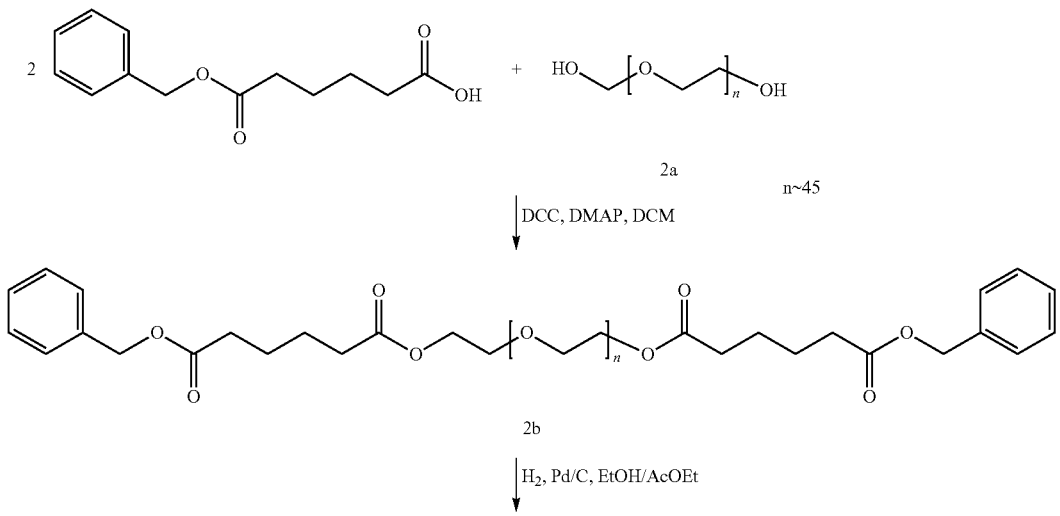

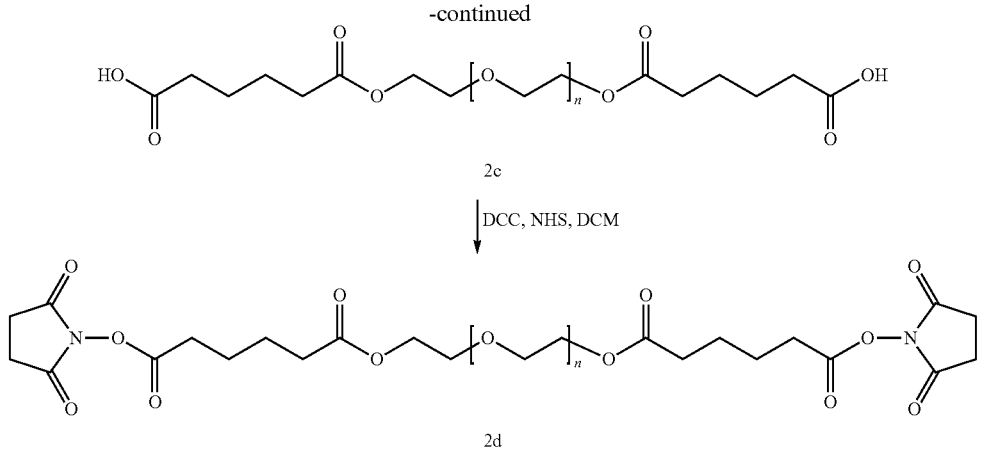

2c

↓ DCC, NHS, DCM

2d

A solution of PEG 2000 (2a) (11.0 g, 5.5 mmol) and benzyl adipate half-ester (4.8 g, 20.6 mmol) in dichloromethane (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by destillation in vacuo. The residue was dissolved in 1000 mL 1/1(v/v) diethyl ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled diethyl ether (−30° C.). The filter cake was dried in vacuo. Yield: 11.6 g (86%) 2b as a colorless solid. The product was used without further purification in the next step.

MS: m/z 813.1=[M+3H]$^{3+}$ (calculated=813.3)

In a 500 mL glass autoclave PEG2000-bis-adipic acid-bis-benzyl ester 2b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo. Yield: 12.3 g (quantitative) 2c as yellowish oil. The product was used without further purification in the next step.

MS: m/z 753.1=[M+3H]$^{3+}$ (calculated=753.2)

A solution of PEG2000-bis-adipic acid half ester 2c (9.43 g, 4.18 mmol), N-hydroxysuccinimide (1.92 g, 16.7 mmol) and dicyclohexylcarbodiimide (3.44 g, 16.7 mmol) in 75 ml of DCM (anhydrous) was stirred over night at room temperature. The reaction mixture was cooled to 0° C. and precipitate was filtered off. DCM was evaporated and the residue was recystallized from THF.

Yield: 8.73 g (85%) crosslinker reagent 2d as colorless solid.

MS: m/z 817.8=[M+3H]$^{3+}$ (calculated=817.9 g/mol).

Example 3

Preparation of Hydrogel Beads (3) and (3a) Containing Free Amino Groups

A solution of 275 mg 1g and 866 mg 2d in 14 mL DMSO was added to a solution of 100 mg Arlacel P135 (Croda International Plc) in 60 mL heptane. The mixture was stirred at 700 rpm with a custom metal stirrer for 10 min at 25° C. to form a suspension. 1.0 mL N,N,N',N'-tetramethyl-ethylenediamine was added to effect polymerization. After 2 h, the stirrer speed was reduced to 400 rpm and the mixture was stirred for additional 16 h. 1.5 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 µm mesh steel sieves. Bead fractions that were retained on the 32, 40, and 50 µm sieves were pooled and washed 3 times with water, 10 times with ethanol and dried for 16 h at 0.1 mbar to give 3 as a white powder.

3a was prepared as described for 3 except for the use of 1200 mg 1g, 3840 mg 2d, 28.6 ml DMSO, 425 mg Arlacel P135, 100 mL heptane and 4.3 ml TMEDA. For workup, 6.6 ml acetic acid were added and then after 10 min 50 mL of water and 50 mL of saturated aqueous sodium chloride solution were added.

Amino group content of hydrogel was determined by conjugation of a fmoc-amino acid to the free amino groups on the hydrogel and subsequent fmoc-determination as described by Gude, M., J. Ryf, et al. (2002) Letters in Peptide Science 9(4): 203-206.

The amino group content of 3 and 3a was determined to be between 0.11 and 0.16 mmol/g.

Example 4

Preparation of Maleimide Functionalized Hydrogel Beads (4) and (4a) and (4Aa) and Determination of Maleimide Substitution

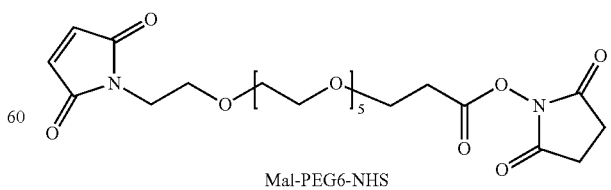

Mal-PEG6-NHS

A solution of 600 mg Mal-PEG6-NHS (1.0 mmol) in 4.5 mL 2/1 (v/v) acetonitrile/water was added to 200 mg dry hydrogel beads 3. 500 µL sodium phosphate buffer (pH 7.4, 0.5 M) was added and the suspension was agitated for 30 min at room temperature. Beads 4 were washed five times each with 2/1 (v/v) acetonitrile/water, methanol and 1/1/0.001 (v/v/v/) acetonitrile/water/TFA.

4a was synthesized as described above except for the use of 3a instead of 3.

Alternatively, hydrogel beads 3a were pre-washed with 99/1 (v/v) DMSO/DIEA, washed with DMSO and incubated for 45 min with a solution of Mal-PEG6-NHS (2.0 eq relative to theoretical amount of amino groups on hydrogel) in DMSO. Beads 4aa were washed two times with DMSO and three times with pH 3.0 succinate (20 mM, 1 mM EDTA, 0.01% Tween-20). The sample was incubated in pH 6.0 sodium phosphate (50 mM, 50 mM ethanolamine, 0.01% Tween-20) for 1 h at RT and washed five times with pH 3.0 sodium succinate (20 mM, 1 mM EDTA, 0.01% Tween-20).

For determination of maleimide content, an aliquot of hydrogel beads 4, 4a, or 4aa, respectively, was lyophilized and weighed out. Another aliquot of hydrogel beads 4, 4a or 4aa, respectively, was reacted with excess mercaptoethanol (in 50 mM sodium phosphate buffer, 30 min at RT), and mercaptoethanol consumption was detected by Ellman test (Ellman, G. L. et al., *Biochem. Pharmacol.*, 1961, 7, 88-95). Maleimide content was determined to be between 0.11 and 0.13 mmol/g dry hydrogel.

Example 5

Synthesis of Linker Reagent 5d

Linker reagent 5d was synthesized according to the following scheme:

hours the solution was poured into diethyl ether (300 mL) and washed three times with 30/1 (v/v) brine/0.1 M NaOH solution (50 ml each) and once with brine (50 mL). The organic phase was dried over $Na_2SO_4$ and volatiles were removed under reduced pressure to obtain the Mmt-protected intermediate (3.18 g, 9.56 mmol).

The Mmt-protected intermediate (3.18 g, 9.56 mmol) was dissolved in anhydrous DCM (30 mL). 6-(Tritylmercapto)-hexanoic acid (4.48 g, 11.47 mmol), PyBOP (5.67 g, 11.47 mmol) and DIEA (5.0 mL, 28.68 mmol) were added and the mixture was agitated for 30 min at RT. The solution was diluted with diethyl ether (250 mL) and washed three times with 30/1 (v/v) brine/0.1 M NaOH solution (50 mL each) and once with brine (50 mL). The organic phase was dried over $Na_2SO_4$ and volatiles were removed under reduced pressure. 5a was purified by flash chromatography.

Yield: 5.69 g (8.09 mmol).

MS: m/z 705.4=$[M+H]^+$ (calculated=705.0).

Synthesis of Linker Reagent Intermediate 5b:

To a solution of 5a (3.19 g, 4.53 mmol) in anhydrous THF (50 mL) was added $BH_3$.THF (1 M solution, 8.5 mL, 8.5 mmol) and the solution was stirred for 16 hours at RT. Further $BH_3$.THF (1 M solution, 14 mL, 14 mmol) was added and stirred for 16 hours at RT. The reaction was quenched by addition of methanol (8.5 mL), N,N-dimethyl-ethylenediamine (3 mL, 27.2 mmol) was added and the solution was heated to reflux and stirred for three hours. The mixture was diluted with ethyl acetate (300 mL) at RT, washed with saturated, aqueous $Na_2CO_3$ solution (2×100 mL) and saturated, aqueous $NaHCO_3$ solution (2×100 mL). The organic phase was dried over $Na_2SO_4$ and volatiles were evaporated at reduced pressure to obtain the crude amine intermediate (3.22 g).

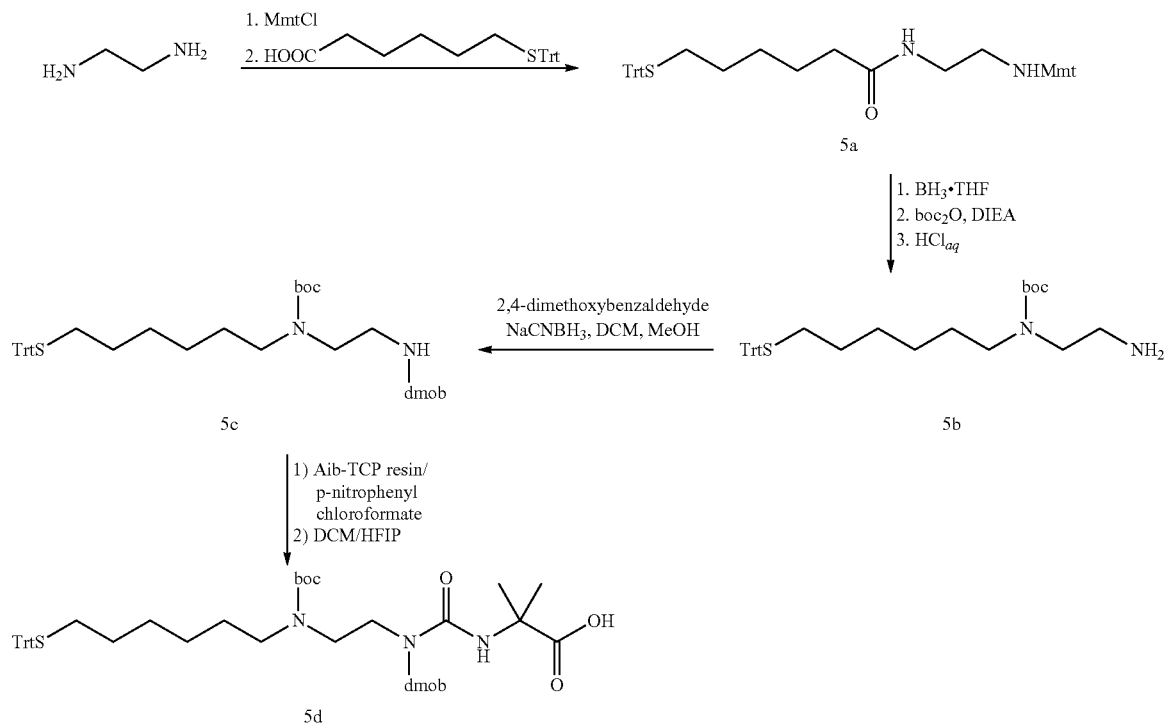

Synthesis of Linker Reagent Intermediate 5a:

4-Methoxytrityl chloride (3 g, 9.71 mmol) was dissolved in DCM (20 mL) and added dropwise to a solution of ethylenediamine (6.5 mL, 97.1 mmol) in DCM (20 mL). After two The amine intermediate was dissolved in DCM (5 mL), $Boc_2O$ (2.97 g, 13.69 mmol) dissolved in DCM (5 mL) and DIEA (3.95 mL, 22.65 mmol) were added and the mixture was agitated at RT for 30 min. The mitxture was purified by flash chromatography to obtain the crude Boc- and Mmt-protected intermediate (3 g).

MS: m/z 791.4=[M+H]$^+$, 519.3=[M-Mmt+H]$^+$ (calculated=791.1).

0.4 M aqueous HCl (48 mL) was added to a solution of the Boc- and Mmt-protected intermediate in acetonitrile (45 mL). The mixture was diluted with acetonitrile (10 ml) and stirred for one hour at RT. Subsequently, the pH value of the reaction mixture was adjusted to 5.5 by addition of 5 M NaOH solution, acetonitrile was removed under reduced pressure and the aqueous solution was extracted with DCM (4×100 mL). The combined organic phases were dried over Na$_2$SO$_4$ and volatiles were removed under reduced pressure. Crude 5b was used without further purification.

Yield: 2.52 g (3.19 mmol).

MS: m/z 519.3=[M+H]$^+$ (MW calculated=518.8 g/mol).

Synthesis of Linker Reagent Intermediate 5c:

5b (780 mg, 0.98 mmol, ~65% purity) and NaCNBH$_3$ (128 mg, 1.97 mmol) were dissolved in anhydrous methanol (13 mL). A solution of 2,4-dimethoxybenzaldehyde (195 mg, 1.17 mmol) in DCM (2 mL) was added, and the mixture was stirred for 2 h at RT. The solvents were evaporated under reduced pressure, and the crude product was dissolved in DCM and washed with saturated NaCO$_3$ solution. The aqueous phase was extracted three times with DCM, and the combined organic phases were washed with brine, dried over MgSO$_4$ and concentrated under reduced pressure. 5c was purified by flash chromatography using DCM and MeOH as eluents.

Yield: 343 mg (0.512 mmol).

MS: m/z 669.37=[M+H]$^+$, (calculated=669.95).

Synthesis of Linker Reagent 5d:

Fmoc-Aib-loaded TCP resin (980 mg, ~0.9 mmol) was deprotected with DMF/piperidine, washed with DMF (5 times) and DCM (6 times) and dried in vacuo. The resin was treated with a solution of p-nitrophenyl chloroformate (364 mg, 1.81 mmol) and collidine (398 µL, 3.0 mmol) in anhydrous THF (6 mL) and shaken for 30 min. The reagent solution was removed by filtration and the resin was washed with THF (5 times) before a solution of amine 5c (490 mg, 0.7 mmol) and DIEA (1.23 mL, 7.1 mmol) in anhydrous THF (6 mL) was added. After shaking for 18 h at RT, the reagent solution was removed by filtration and the resin was washed with DCM (5 times). The linker reagent was cleaved from the resin and purified by RP-HPLC. Product fractions were brought to pH 6 by addition of sat. aq. NaHCO$_3$ and concentrated under reduced pressure. The resulting slurry was partitioned between saturated aqueous NaCl and DCM, and the aqueous layer was extracted with DCM. The combined organic fractions were concentrated to dryness to afford linker reagent 5d.

Yield: 230 mg, (0.29 mmol).

MS m/z 798.41=[M+H]$^+$, (calculated=798.1).

Example 6

Synthesis of Linker Reagent 6c

Linker reagent 6c was synthesized according to the following scheme:

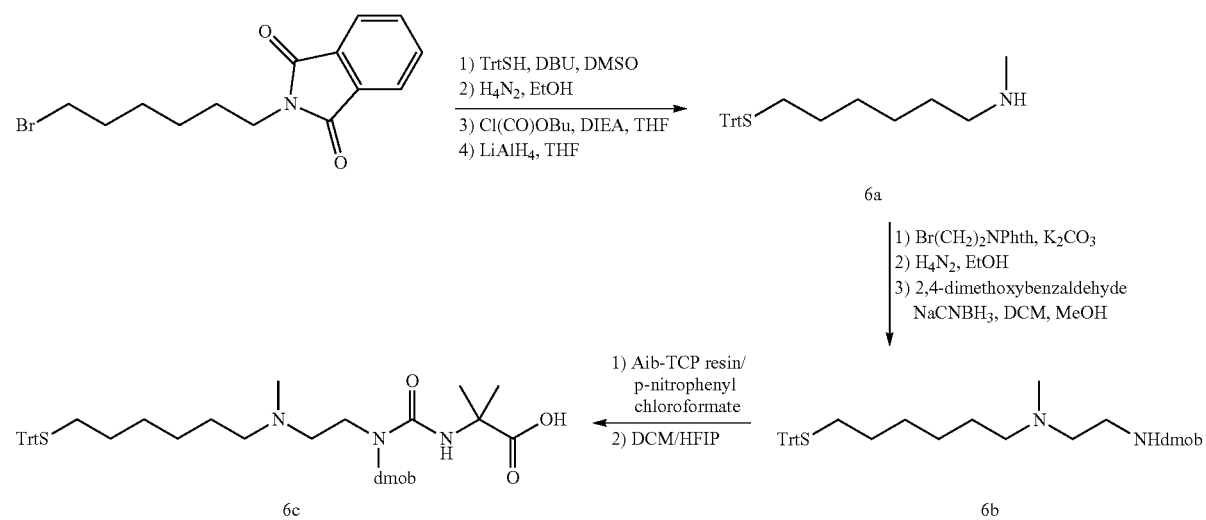

Synthesis of Amine 6a:

Triphenylmethanethiol (11.90 g, 43.08 mmol) was suspended in DMSO (40 mL). DBU (7.41 mL, 49.55 mmol) and 6-bromohexylphthalimide (13.32 g, 42.94 mmol) were added, and the mixture was allowed to react for approximately 15 min. The reaction mixture was partitioned between ethyl acetate (700 mL) and 0.1 M HCl (200 mL). The aqueous phase was extracted with ethyl acetate (3×50 mL), and the combined organic fractions were washed with NaHCO$_3$ sat. (80 mL) and brine (80 mL), dried over MgSO$_4$, filtered and concentrated. The crude yellow oil was recrystallized from n-heptane/ethyl acetate. The intermediate 6-(S-Trityl-)mercaptohexylphthalimide was obtained as a white solid (13.3 g, 26.4 mmol, 62%).

6-(S-Trityl-)mercaptohexylphthalimide (14.27 g, 28.2 mmol) was suspended in ethanol (250 mL). Hydrazine hydrate (3.45 mL, 70.5 mmol) was added, and the mixture was heated to reflux for 2 h. The mixture was filtered and the filtrate was concentrated in vacuo. Chloroform (180 mL) was added to the residual oil and the resulting suspension was stirred at room temperature for 1.5 h. The mixture was filtered, and the filtrate was extracted with water (60 mL) and brine (60 mL), dried over MgSO$_4$ and concentrated to yield crude 6-(tritylmercapto)-hexylamine (10.10 g, 26.87 mmol, 95%). MS: m/z 376.22=[M+H]$^+$, (calculated=376.20).

DIEA (1.41 mL, 8.11 mmol) and n-butyl chloroformate (908 μL, 7.14 mmol, in 1 mL THF) were added to a cooled (0° C.) solution of 6-(tritylmercapto)-hexylamine (2.44 g, 6.49 mmol) in THF (50 mL). LiAlH$_4$ (1 M in THF, 9.74 mL, 9.47 mmol) was added after 30 min, and the mixture was heated to reflux for 90 min. Addition of water, 3.75 M aq. NaOH and water led to the formation of a precipitate which was removed from the mixture by filtration. The filtrate was concentrated in vacuo to obtain 6a.

Yield: 2.41 g (6.20 mmol).

MS: m/z 390.22=[M+H]$^+$, (calculated=390.22).

Synthesis of linker reagent intermediate 6b: To a solution of 6a (2.1 g, 5.31 mmol) was added 2-bromoethylphthalimide (1.96 g, 7.7 mmol) and K$_2$CO$_3$ (1.09 g, 7.9 mmol) and the mixture was heated to reflux for 6 h. After filtration and concentration, the crude mixture was partitioned between ethyl acetate and saturated aqueous NaHCO$_3$. The crude intermediate (2-(N-methyl-N-(6-tritylmercaptohexyl-)amino-)ethyl)phthalimide was purified by flash chromatography.

Yield: 1.23 g (2.18 mmol).

MS: m/z: 563.27=[M+H]$^+$, (calculated=563.27).

To a solution of (2-(N-methyl-N-(6-tritylmercaptohexyl-)amino-)ethyl)phthalimide (672 mg, 1.19 mmol) in ethanol (12 mL) was added hydrazine monohydrate (208 μL, 4.17 mmol), and the mixture was heated to reflux for 1 h. The reaction mixture was filtered, concentrated and N-(2-aminoethyl+N-methyl-N-(6-tritylmercaptohexyl)amine purified by RP-HPLC.

Yield: 624 mg (0.944 mmol).

MS: m/z 433.27=[M+H]$^+$, (calculated=433.26).

To a solution of N-(2-aminoethyl-)-N-methyl-N-(6-tritylmercaptohexyl-)amine (151 mg, 0.229 mmol) and NaCNBH$_3$ (30 mg, 0.463 mmol) in anhydrous MeOH (6 mL) was added a soltution of 2,4-dimethoxybenzaldehyde in anhydrous CH$_2$Cl$_2$ (0.6 ML). After stirring for 1 h at RT, the reaction mixture was concentrated, redissolved in 2 mL water/acetonitrile 1/9 (v/v) and 6b purified by RP-HPLC.

Yield: 177 mg (0.219 mmol).

MS: m/z 583.33=[M+H]$^+$, (calculated=583.33).

Synthesis of Linker Reagent 6c

Linker reagent 6c was prepared from Fmoc-Aib-loaded resin (704 mg, ~0.6 mmol) as described for 5d, except for the use of amine 6b (as TFA salt, 430 mg, 0.53 mmol) instead of 5c.

Yield: 285 mg, (0.330 mmol).

MS: m/z 712.37=[M+H]$^+$, (calculated=712.37).

Example 7

Synthesis of Linker Reagent 7f

Linker reagent 7f was synthesized according to the following scheme:

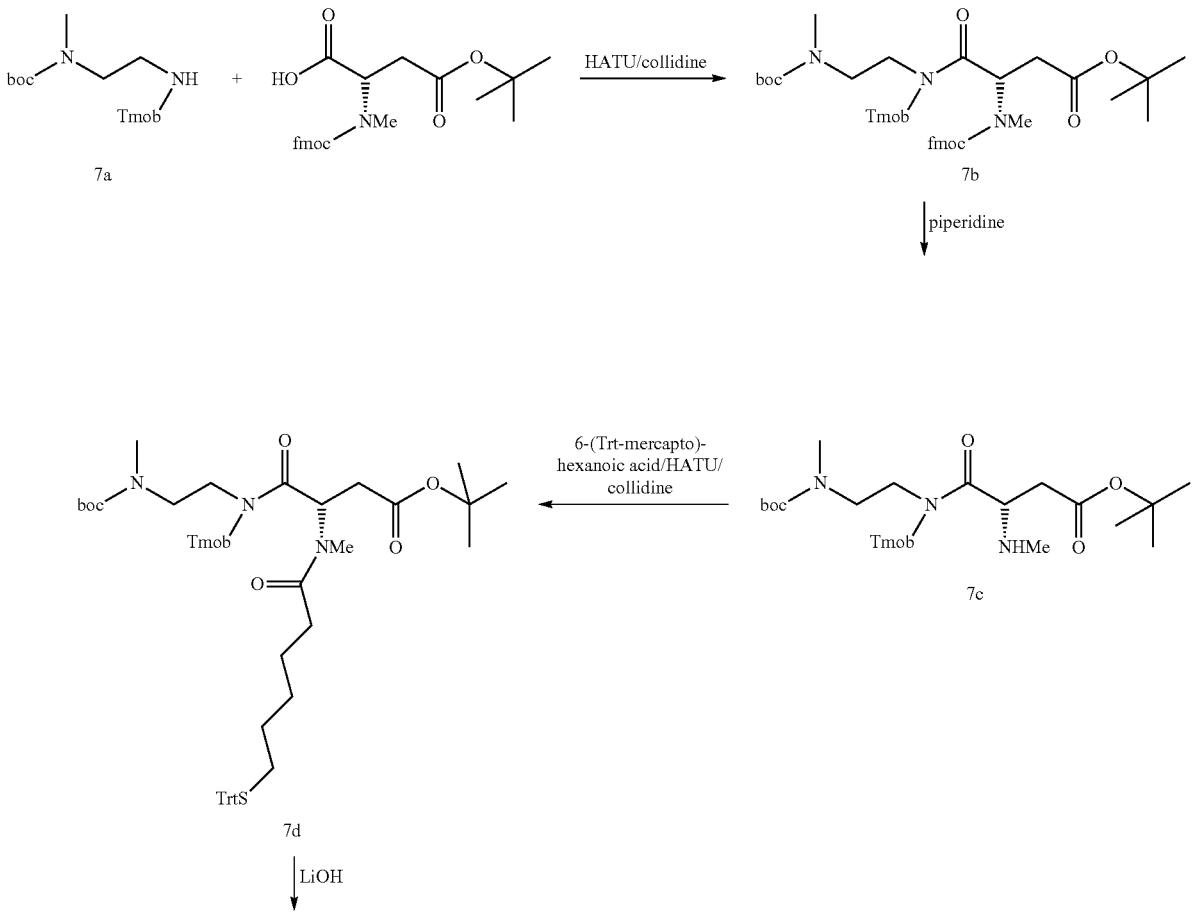

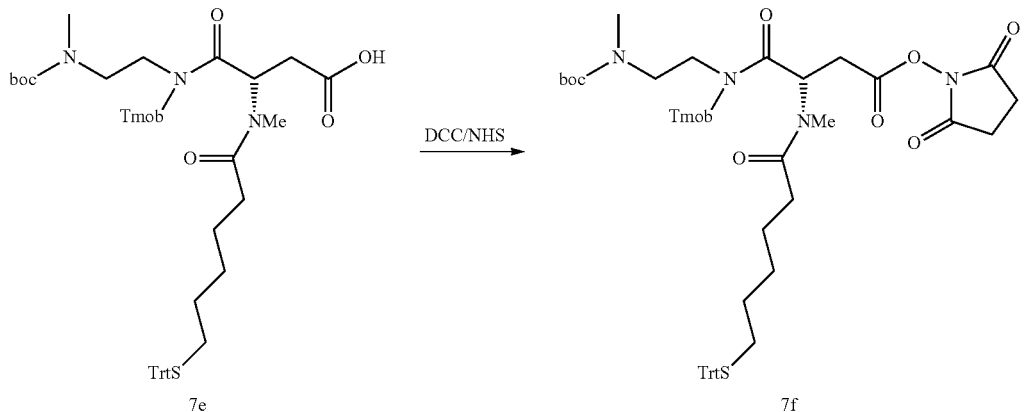

To a cooled (0° C.) solution of N-Methyl-N-boc-ethylendiamine (0.5 mL, 2.79 mmol) and NaCNBH$_3$ (140 mg, 2.23 mmol) in MeOH (10 mL) and acetic acid (0.5 mL) was added a solution of 2,4,6-trimethoxybenzaldehyde (0.547 mg, 2.79 mmol) in EtOH (10 mL). The mixture was stirred at RT for 2 h, acidified with 2 M HCl (1 mL) and neutralized with saturated aqueous Na$_2$CO$_3$ (50 mL). Evaporation of all volatiles, DCM extraction of the resulting aqueous slurry and concentration of the organic fractions yielded N-Methyl-N-boc-N'-tmob-ethylendiamine (7a) as a crude oil which was purified by RP-HPLC.

Yield: 593 mg (1.52 mmol)

MS: m/z 377.35=[M+Na]$^+$, (calculated=377.14).

N-Fmoc-N-Me-Asp(OtBu)-OH (225 mg, 0.529 mmol) was dissolved in DMF (3 mL) and 7a (300 mg, 0.847 mmol), HATU (201 mg, 0.529 mmol), and collidine (0.48 ml, 3.70 mmol) were added. The mixture was stirred at RT for 2 h to yield 7b. For fmoc deprotection, piperidine (0.22 mL, 2.16 mmol) was added and stirring was continued for 1 h. Acetic acid (1 mL) was added, and 7c was purified by RP-HLPC.

Yield: 285 mg (0.436 mmol as TFA salt)

MS: m/z 562.54=[M+Na]$^+$, (calculated=562.67).

6-Tritylmercaptohexanoic acid (0.847 g, 2.17 mmol) was dissolved in anhydrous DMF (7 mL). HATU (0.825 g, 2.17 mmol), and collidine (0.8 mL, 6.1 mmol) and 7c (0.78 g, 1.44 mmol) were added. The reaction mixture was stirred for 60 min at RT, acidified with AcOH (1 mL) and purified by RP-HPLC. Product fractions were neutralized with saturated aqueous NaHCO$_3$ and concentrated. The remaining aqueous phase was extracted with DCM and 7d was isolated upon evaporation of the solvent.

Yield: 1.4 g (94%)

MS: m/z 934.7=[M+Na]$^+$, (calculated=934.5).

To a solution of 7d (1.40 mg, 1.53 mmol) in MeOH (12 mL) and H$_2$O (2 nil) was added LiOH (250 mg, 10.4 mmol) and the reaction mixture was stirred for 14 h at 70° C. The mixture was acidified with AcOH (0.8 mL) and 7e was purified by RP-HPLC. Product fractions were neutralized with saturated aqueous NaHCO$_3$ and concentrated. The aqueous phase was extracted with DCM and 7e was isolated upon evaporation of the solvent.

Yield: 780 mg (60%)

MS: m/z 878.8=[M+Na]$^+$, (calculated=878.40).

To a solution of 7e (170 mg, 0.198 mmol) in anhydrous DCM (4 ml) were added DCC (123 mg, 0.59 mmol) and N-hydroxy-succinimide (114 mg, 0.99 mmol), and the reaction mixture was stirred at RT for 1 h. The mixture was filtered, and the filtrate was acidified with 0.5 ml AcOH and 7f purified by RP-HPLC. Product fractions were neutralized with saturated aqueous NaHCO$_3$ and concentrated. The remaining aqueous phase was extracted with DCM and 7f was isolated upon evaporation of the solvent.

Yield: 154 mg (0.161 mmol)

MS: m/z 953.4=[M+H]$^+$, (calculated=953.43).

Alternatively, linker reagent 7f was synthesized according to the following procedure:

Alternative Reaction Scheme:

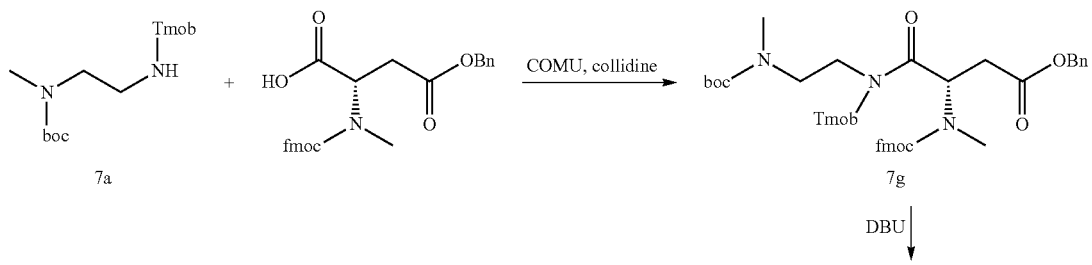

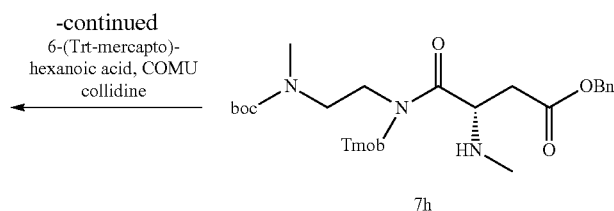
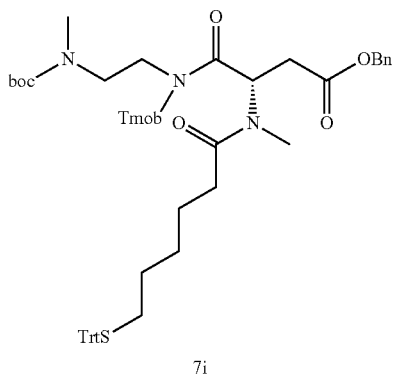
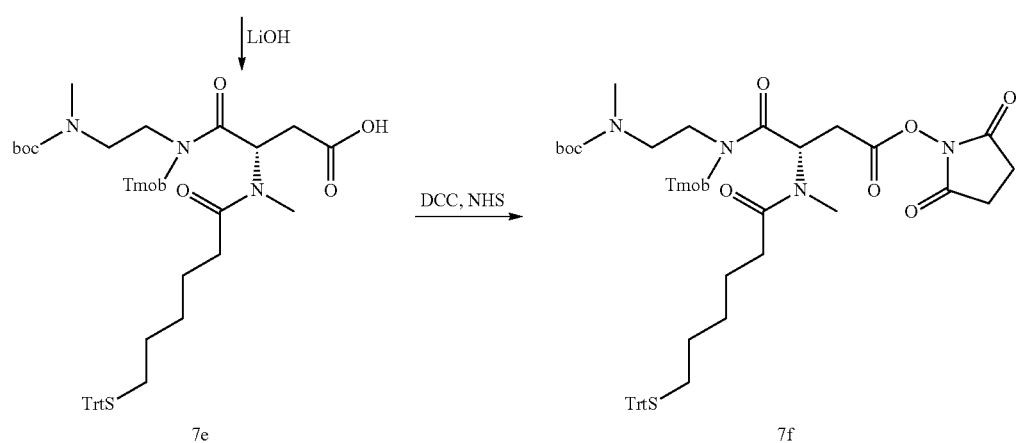

To a solution of N-Methyl-N-boc-ethylenediamine (2 g, 11.48 mmol) and NaCNBH$_3$ (819 mg, 12.63 mmol) in MeOH (20 mL) was added 2,4,6-trimethoxybenzaldehyde (2.08 mg, 10.61 mmol) portion wise. The mixture was stirred at RT for 90 min, acidified with 3 M HCl (4 mL) and stirred further 15 min. The reaction mixture was added to saturated NaHCO$_3$ solution (200 mL) and extracted 5× with CH$_2$Cl$_2$. The combined organic phases were dried over Na$_2$SO$_4$ and the solvents were evaporated in vacuo. The resulting N-Methyl-N-boc-N'-tmob-ethylenediamine (7a) was completely dried in high vacuum and used in the next reaction step without further purification.

Yield: 3.76 g (11.48 mmol, 89% purity, 7a: double Tmob protected product=8:1)

MS: m/z 355.22=[M+H]$^+$, (calculated=354.21).

To a solution of 7a (2 g, 5.65 mmol) in CH$_2$Cl$_2$ (24 ml) COMU (4.84 g, 11.3 mmol), N-Fmoc-N-Me-Asp(OBn)-OH (2.08 g, 4.52 mmol) and collidine (2.65 mL, 20.34 mmol) were added. The reaction mixture was stirred for 3 h at RT, diluted with CH$_2$Cl$_2$ (250 mL) and washed 3× with 0.1 M H$_2$SO$_4$ (100 ml) and 3× with brine (100 ml). The aqueous phases were re extracted with CH$_2$Cl$_2$ (100 ml). The combined organic phases were dried over Na$_2$SO$_4$, filtrated and the residue concentrated to a volume of 24 mL. 7g was purified using flash chromatography.

Yield: 5.31 g (148%, 6.66 mmol)

MS: m/z 796.38=[M+H]$^+$, (calculated=795.37).

To a solution of 7g [5.31 g, max. 4.51 mmol ref. to N-Fmoc-N-Me-Asp(OBn)-OH] in THF (60 mL) DBU (1.8 mL, 3% v/v) was added. The solution was stirred for 12 min at RT, diluted with CH$_2$Cl$_2$ (400 ml) and washed 3× with 0.1 M H$_2$SO$_4$ (150 ml) and 3× with brine (150 ml). The aqueous phases were re extracted with CH$_2$Cl$_2$ (100 ml). The combined organic phases were dried over Na$_2$SO$_4$ and filtrated. 7h was isolated upon evaporation of the solvent and used in the next reaction without further purification.

MS: m/z 574.31=[M+H]$^+$, (calculated=573.30).

7h (5.31 g, 4.51 mmol, crude) was dissolved in acetonitrile (26 mL) and COMU (3.87 g, 9.04 mmol), 6-Tritylmercapto-hexanoic acid (2.12 g, 5.42 mmol) and collidine (2.35 mL, 18.08 mmol) were added. The reaction mixture was stirred for 4 h at RT, diluted with CH$_2$Cl$_2$ (400 ml) and washed 3× with 0.1 M H$_2$SO$_4$ (100 ml) and 3× with brine (100 ml). The aqueous phases were re extracted with CH$_2$Cl$_2$ (100 ml). The combined organic phases were dried over Na$_2$SO$_4$, filtrated and 7i was isolated upon evaporation of the solvent. Product 7i was purified using flash chromatography.

Yield: 2.63 g (62%, 94% purity)

MS: m/z 856.41=[M+H]$^+$, (calculated=855.41).

To a solution of 7i (2.63 g, 2.78 mmol) in i-PrOH (33 mL) and H$_2$O (11 mL) was added LiOH (267 mg, 11.12 mmol) and the reaction mixture was stirred for 70 min at RT. The mixture was diluted with CH$_2$Cl$_2$ (200 ml) and washed 3× with 0.1 M H$_2$SO$_4$ (50 ml) and 3× with brine (50 ml). The aqueous phases were re-extracted with CH$_2$Cl$_2$ (100 ml). The combined organic phases were dried over Na$_2$SO$_4$, filtrated and 7e was isolated upon evaporation of the solvent. 7j was purified using flash chromatography.

Yield: 2.1 g (88%)

MS: m/z 878.4=[M+Na]$^+$, (calculated=878.40).

To a solution of 7e (170 mg, 0.198 mmol) in anhydrous DCM (4 mL) were added DCC (123 mg, 0.59 mmol), and a catalytic amount of DMAP. After 5 min N-hydroxy-succinimide (114 mg, 0.99 mmol) was added and the reaction mixture was stirred at RT for 1 h. The reaction mixture was filtered, the solvent was removed in vacuo and the residue was taken up in 90% acetonitrile plus 0.1% TFA (3.4 ml). The crude mixture was purified by RP-HPLC. Product fractions were neutralized with 0.5 M pH 7.4 phosphate buffer and concentrated. The remaining aqueous phase was extracted with DCM and 7f was isolated upon evaporation of the solvent.

Yield: 154 mg (81%)

MS: m/z 953.4=[M+H]$^+$, (calculated=953.43).

Example 8

Synthesis of N$^{\alpha A1}$-Insulin-Linker Conjugates 8b and 8c

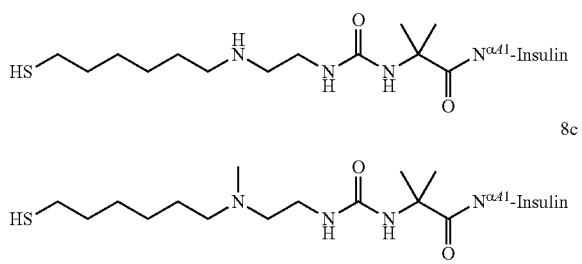

Synthesis of Protected Insulin Linker Conjugate 8a

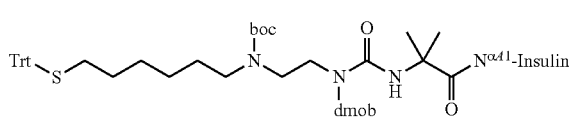

Linker reagent 5d was dissolved in DCM (20 mg/mL) and activated with N-cyclohexyl-carbodiimide-N'-methyl polystyrene-resin (1.9 mmol/g, 10 eq.) for 1h. The solution of the activated linker reagent was added to a solution of insulin (1.2 eq.) and DIEA (3.5 eq.) in DMSO (100 mg insulin/ml), and the mixture was shaken at RT for 45 min. The solution was acidified with acetic acid, the DCM was evaporated under reduced pressure, and N$^{\alpha A1}$-conjugated protected insulin-linker conjugate 8a was purified by RP-HPLC.

Lyophilized 8a was treated with a mixture of 90/10/2/2 (v/v/v/v) HFIP/TFA/water/triethylsilane (2 mL/100 mg of 8a) for 45 min at RT. The reaction mixture was diluted with water, and all volatiles were removed under a stream of nitrogen. N$^{\alpha A1}$-conjugated insulin-linker conjugate 8b was purified by RP-HPLC.

8b:
Yield: 139 mg (0.023 mmol) from 62 mg (0.078 mmol) linker 5d
MS: m/z 1524.45=[M+4H]$^{4+}$ (calculated=1524.75).

N$^{\alpha A1}$-conjugated insulin-linker conjugate 8c was synthesized as described for 8b except for the use of 6c (72 mg, 0.101 mmol) instead of 5d.

8c:
Yield: 237 mg (0.039 mmol)
MS: m/z 1528.23=[M+4H]$^{4+}$ (calculated=1528.28).

Example 9

Synthesis of N$^{\alpha B1}$-insulin-linker conjugate 9

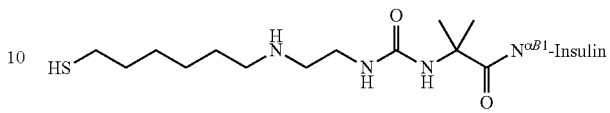

Double-protected N$^\alpha$-boc-Gly$^{A1}$-N$^\epsilon$-boc-Lys$^{B29}$-insulin was prepared as described previously (J. Markussen, J. Halstrøm, F. C. Wiberg, L. Schïffer, J. Biol. Chem. 1991, 266, 18814-18818). Linker reagent 5d (0.04 mmol) was dissolved in DCM (0.5 mL) and activated with N-cyclohexyl-carbodiimide-N'-methyl polystyrene resin (0.205 mmol) at RT for 2h. The resulting solution of the activated linker reagent was added to a solution of bis-boc-protected insulin (24 mg, 0.004 mmol) and DIEA (5 µL, 0.0229 mmol) and shaken at RT for 1 h. The reaction mixture was acidified with 100 µL of acetic acid and protected insulin-linker conjugate was purified by RP-HPLC.

Yield: 5 mg (0.00075 mmol).
MS: m/z 1660.27=[M+4H]$^{4+}$ (calculated=1660.43).

Lyophilized protected insulin-linker conjugate was treated with 1 mL 90/10/2/2 (v/v/v/v) HFIP/TFA/water/TES at RT for 45 min. The reaction mixture was diluted with 0.5 mL of water and all volatiles were removed under a stream of nitrogen. N$^{\alpha B}$-conjugated insulin-linker conjugate 9 was purified by RP-HPLC.

Yield: 4 mg (0.0007 mmol)
MS: m/z 1524.46=[M+4H]$^{4+}$ (calculated=1524.75).

Example 10

Synthesis of N$^{\epsilon B29}$-insulin linker conjugate 10

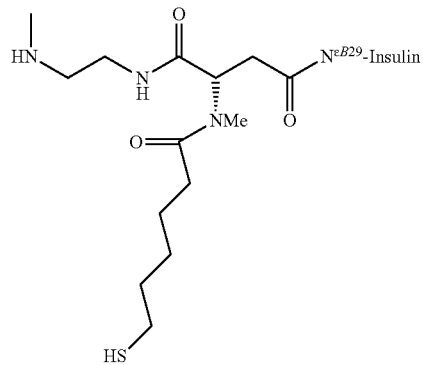

Insulin (644 mg, 0.111 mmol) was dissolved in 6.5 mL of DMSO. 3 mL of cooled (4° C.) 0.5 M sodium borate buffer (pH 8.5) and 7f (70 mg, 0.073 mmol) in 2.5 mL of DMSO were added and mixture was stirred for 5 min at RT. 400 µL AcOH were added and protected insulin conjugate was purified by RP HPLC.

Yield: 172 mg (0.025 mmol).
MS: m/z 1662.27=[M+4H]$^{4+}$ (calculated=1662.48).

Removal of protecting groups was affected by treatment of lyophilized product fractions with 6 mL of 90/10/2/2 (v/v/v/v) HFIP/TFA/TES/water for 1 h at RT. $N^{\alpha B29}$-conjugated insulin-linker conjugate 10 was purified by RP HPLC.

Yield: 143 mg (0.023 mmol).

MS: m/z 1531.46=$[M+4H]^{4+}$ (calculated=1531.71).

Example 11

Preparation of Insulin-Linker-Hydrogel 11a, 11b, 11c, 11d, 11Da, 11db, and 11dc

Insulin-linker-hydrogel 11a was washed 10 times with acetonitrile/water/TFA 1/1/0.001 (v/v/v) and stored at 4° C.

Insulin content was determined by total hydrolysis of an aliquot of insulin-linker-hydrogel under reductive conditions at pH 12 and subsequent insulin A-chain and insulin B-chain quantification by RP-HPLC.

Insulin loading of 11a: 175 mg insulin/g insulin-linker-hydrogel

Insulin amount in a 11a suspension in 10 mM sodium acetate buffer pH 5, 135 mM sodium chloride: 12 mg insulin per 1 ml 1.1a suspension.

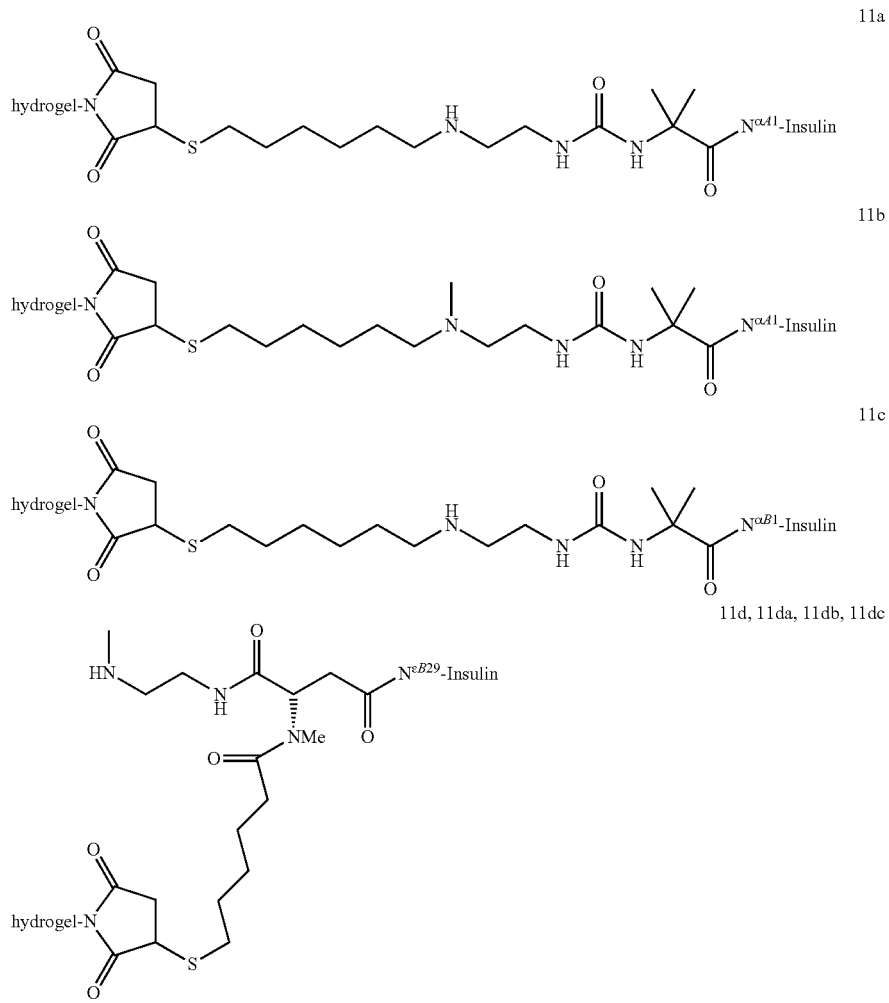

Dry maleimide functionalized hydrogel 4 (82 mg, 10.3 µmol maleimido groups) was filled into a syringe equipped with a filter frit. A solution of insulin-linker-thiol 8b (27.8 mg, 4.6 µmol) in 1.0 mL acetonitrile/water/TFA 1/1/0.001 (v/v/v) was added and the suspension was incubated for 5 min at RT. Acetate buffer (0.4 mL, pH 4.8, 1.0 M) was added and the sample was incubated at RT for 1 h. Consumption of thiol was monitored by Ellman test. Hydrogel was washed 10 times with 1/0.43/0.001 (v/v/v) acetonitrile/water/TFA and 2 times with 1/1/0.2/0.25 (v/v/v/v) 1.0 M sarcosine pH 7.4/acetonitrile/0.5 M phosphate buffer pH 7.4/water. Finally, the hydrogel was suspended in the sarcosine solution and incubated for 2 h at RT.

11b, 11c, and 11d were prepared as described above except for the use of 8c, 9, and 10, respectively, instead of 8b.

11da was prepared as described above except for the use of 10 and 4a instead of 8b and 4.

11db was prepared as follows: A suspension of maleimide functionalized hydrogel 4a in pH 2.5 HCl, 0.01% Tween-20 (5.0 mL, 119 µmol maleimido groups) was filled into a syringe equipped with a filter. A solution of insulin-linker-thiol 10 (166 mg, 24.4 µmol) in 8.0 mL HCl pH 2.5, 0.01% Tween-20 was added and the suspension was incubated for 5 min at RT. Sodium succinate buffer (3.9 mL, pH 4.0, 150 mM; 1 mM EDTA, 0.01% Tween-20) was added to yield pH 3.6 and the sample was incubated at RT for 90 min. Consumption of thiol was monitored by Ellman test. Hydrogel was washed 10 times with sodium succinate buffer (pH 3.0, 50 mM; 1 mM EDTA, 0.01% Tween-20) and 3 times with sodium succinate buffer (pH 3.0, 50 mM; 1 mM EDTA, 0.01% Tween-20) containing 200 mM acetyl cysteine. Finally, the hydrogel was suspended in the acetyl cysteine containing buffer and incubated for 1 h at RT.

Insulin-linker-hydrogel 11db was washed 10 times with succinate buffer (pH 3.0, 50 mM; 1 mM EDTA, 0.01% Tween-20) and 8 times with sodium acetate buffer (pH 5.0, 10 mM; 130 mM NaCl, 0.01% Tween-20).

Insulin loading of 11db: 6.12 mg insulin per mL insulin-linker-hydrogel suspension 11dc was prepared as follows: A suspension of maleimide functionalized hydrogel 4a in pH 2.5 HCl, 0.01% Tween-20 (58.3 mL, 958 µmol maleimido groups) was added to a solid phase synthesis reactor. A solution of insulin-linker-thiol 10 (117 mL, 460 µmol) in 2.5 HCl, 0.01% Tween-20 was added to 4a. The suspension was incubated at RT for 5 min. Succinate buffer (4.8 mL, pH 4.0, 150 mM; 1 mM EDTA, 0.01% Tween-20) was added to yield a pH of 3.6 and the suspension was incubated at RT for 90 min.

Consumption of thiol was monitored by Ellman test. Hydrogel was washed 10 times with succinate buffer (pH 3.0, 50 mM; 1 mM EDTA, 0.01% Tween-20) and 2 times with succinate buffer (pH 3.0, 50 mM; 1 mM EDTA, 0.01% Tween-20) containing 10 mM mercaptoethanol. Finally, the hydrogel was suspended in the mercaptoethanol containing buffer and incubated for 3 h at RT.

Insulin-linker-hydrogel 11dc was washed 10 times with succinate buffer (pH 3.0, 50 mM; 1 mM EDTA, 0.01% Tween-20) and 6 times with succinate/Tris buffer (pH 5.0, 10 mM; 85 g/L trehalose, 0.01% Tween-20).

Insulin loading of 11dc: 18.7 mg insulin per mL insulin-linker-hydrogel suspension Alternatively, maleimide derivatized hydrogel microparticles 4aa can be used instead of 4a.

Example 12

Release Kinetics In Vitro

Insulin-linker-hydrogel 11a, 11b, 11c and 11d, respectively, (insulin-linker-hydrogel containing ca. 1 mg insulin) were suspended in 2 ml 60 mM sodium phosphate, 3 mM EDTA, 0.01% Tween-20, pH 7.4, and incubated at 37° C. Suspensions were centrifuged at time intervals and supernatant was analyzed by RP-HPLC at 215 nm and ESI-MS. UV-signals correlating to liberated insulin were integrated and plotted against incubation time.

Curve-fitting software was applied to estimate the corresponding halftime of release.

In vitro half-lives of 16 d, 10 d, 30 d, and 14 d were determined for 11a, 11b, 11c and 11d, respectively.

Alternatively, insulin-linker-hydrogel 11db was transferred to syringes equipped with filters, suspended in 6 ml 60 mM sodium phosphate, 3 mM EDTA, 0.01% Tween-20, pH 7.4, and incubated at 37° C. At defined time points the supernatant was exchanged and liberated insulin was quantified by RP-HPLC at 215 nm. The amount of released insulin was plotted against incubation time. Curve-fitting software was applied and an in vitro halftime of 15 d was determined for 11db.

Alternatively, insulin-linker-hydrogel 11db was filled in a chromatography column and placed in a temperature controlled incubator (37° C.). Sodium phosphate (pH 7.4, 60 mM; 3 mM EDTA, 0.01% Tween-20) was pumped through the column with a constant flow of 0.25 mL/h (nominal) and collected outside the incubator. At defined time points the solution was analyzed by RP-HPLC at 215 nm. The amount of released insulin was plotted against incubation time. Curve-fitting software was applied and an in vitro halftime of 13 d was determined for 11db.

Example 13

Synthesis of a LysB29-Linker Conjugate of Insulin (12a) and a LysB28-Linker Conjugate of Insulin Lispro (12b)

Synthesis of LysB29-Linker Conjugate of Insulin (12a)

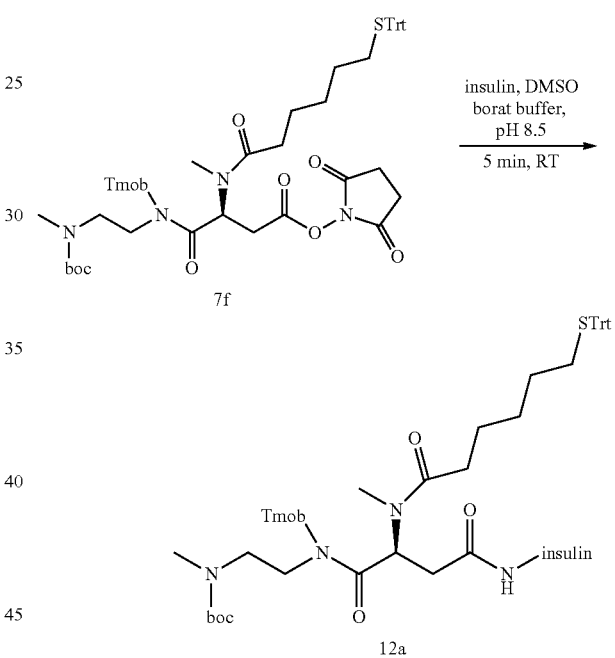

1.2 g (0.206 mmol, 0.85 eq) of insulin were dissolved in DMSO at RT. After 30 min the solution was cooled to 0° C. while borate buffer (0.5 M, pH 8.5, 21.6 ml) was added over a period of 4.40 min. The temperature of the solution was kept between 25 and 28° C. A solution of 228 mg (0.239 mmol, 1 eq) 7f was dissolved in 40 ml DMSO was added time-invariant over a period of 3 min. The ice bath was removed and the reaction mixture was stirred for 5 min at RT. The reaction was quenched by addition of 70 ml of MeCN/H$_2$O (1:1, 0.1% TFA) and 400 µl AcOH. 12a was purified by RP HPLC (solvent A: H$_2$O with 0.1% TFA, solvent B: MeCN with 0.1% TFA, gradient: 30-80% B over 14 min, flow: 40 ml/min).

Regio-selectivity according to UPLC analysis (before RP HPLC purification): 0.70% 7f attached to GlyA1 of insulin and 76.2% 7f attached to LysB29 of insulin (see FIG. 1a).

Yield: 862 mg (TFA-salt, 60%).

MS [M+H]$_{114}^+$=1662.25 g/mol ((MW+H)$_{1/4}$ calculated=1662.35 g/mol).

Synthesis of LysB28-Linker Conjugate of Insulin Lispro (12b)

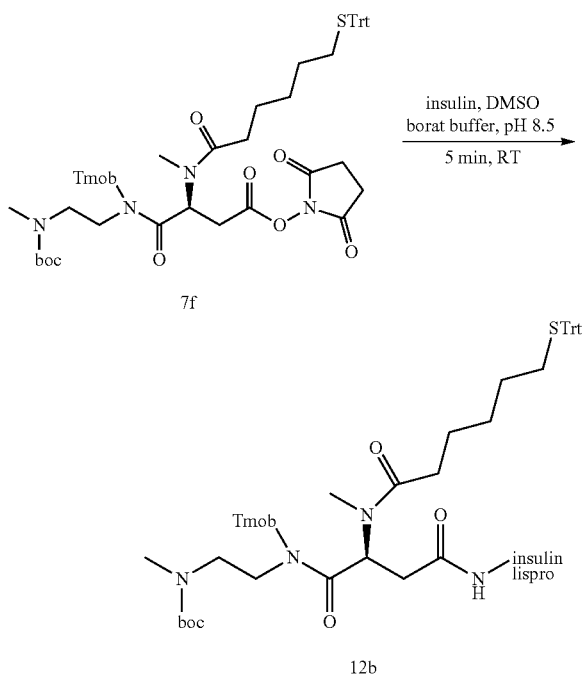

0.347 g (0.059 mmol, 0.85 eq) of insulin lispro were dissolved in 6 ml DMSO at RT. After 30 min the solution was cooled to 0° C. while borate buffer (0.5 M, pH 8.5, 5.64 ml) was added over a period of 1.40 min. The temperature of the solution was kept between 25 and 30° C. A solution of 67 mg (0.070 mmol, 1 eq) 7f dissolved in 8 ml DMSO was added time-invariant over a period of 2 min. The ice bath was removed and the reaction mixture was stirred for 5 min at RT. The reaction was quenched by addition of 20 ml of MeCN/ $H_2O$ (1:1, 0.1% TFA) and 1 ml AcOH. 12b was purified by RP HPLC (solvent A: $H_2O$ with 0.1% TFA, solvent B: MeCN with 0.1% TFA, gradient: 30-80% B over 14 min, flow: 40 ml/min).

Figure 1B:
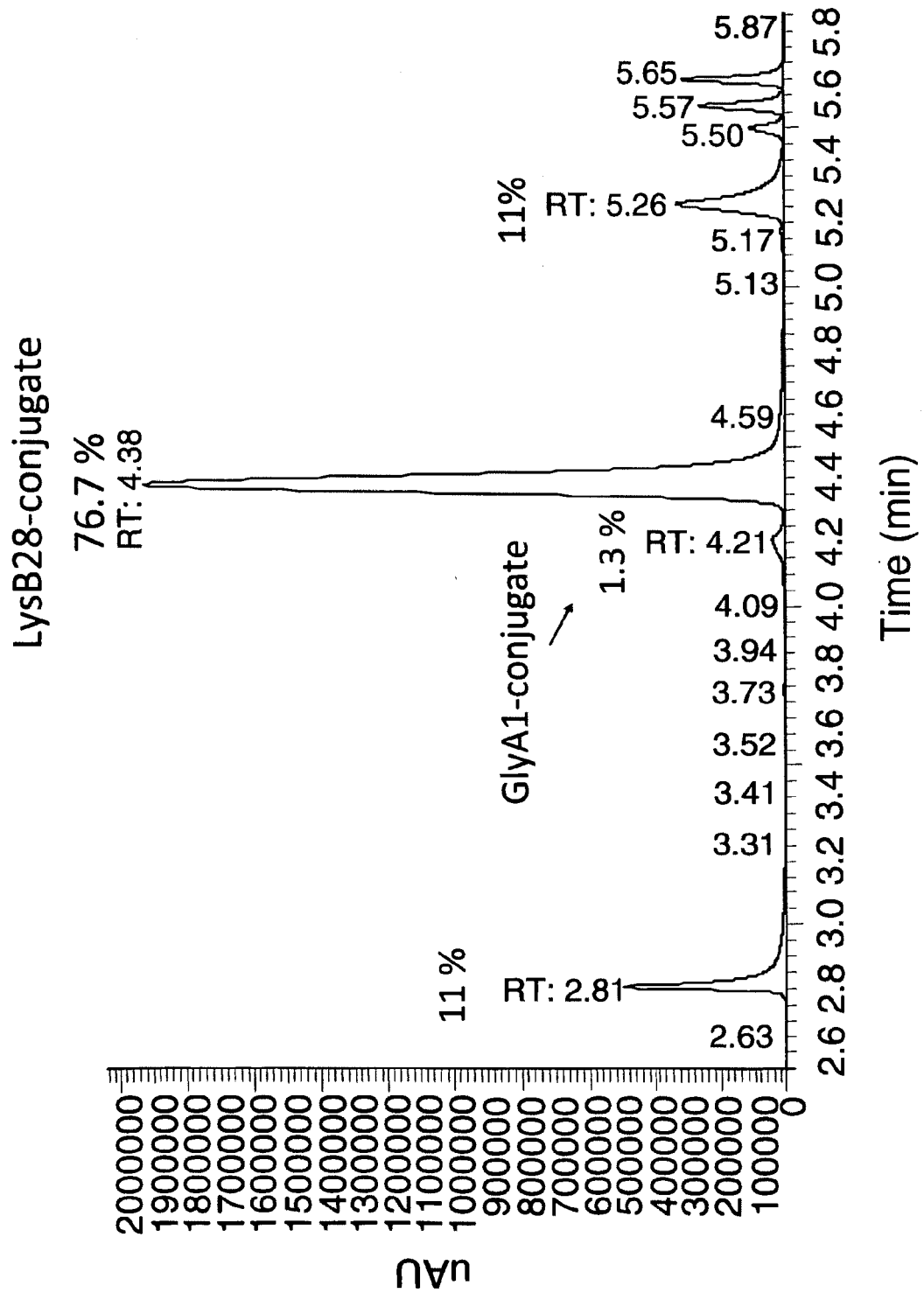
FIG. 1b: UPLC chromatogram of insulin-linker conjugate 12b.

Regio-selectivity according to UPLC analysis (before RP HPLC purification): 1.3% of the product was 7f attached to GlyA1 of insulin lispro, 76.7% of the product was 7f attached to LysB28 of insulin lispro (see FIG. 1b).

Yield: 305 mg (TFA-salt, 72%).

MS $[M+H]_{1/4}^+$=1662.25 g/mol $((MW+H)_{1/4}$ calculated=1662.35 g/mol).

Example 14

Pharmacokinetics Study in Rat

The pharmacokinetics of 11a were determined by measuring the plasma insulin concentration after subcutaneous application of a single dose into rats.

Figure 2:
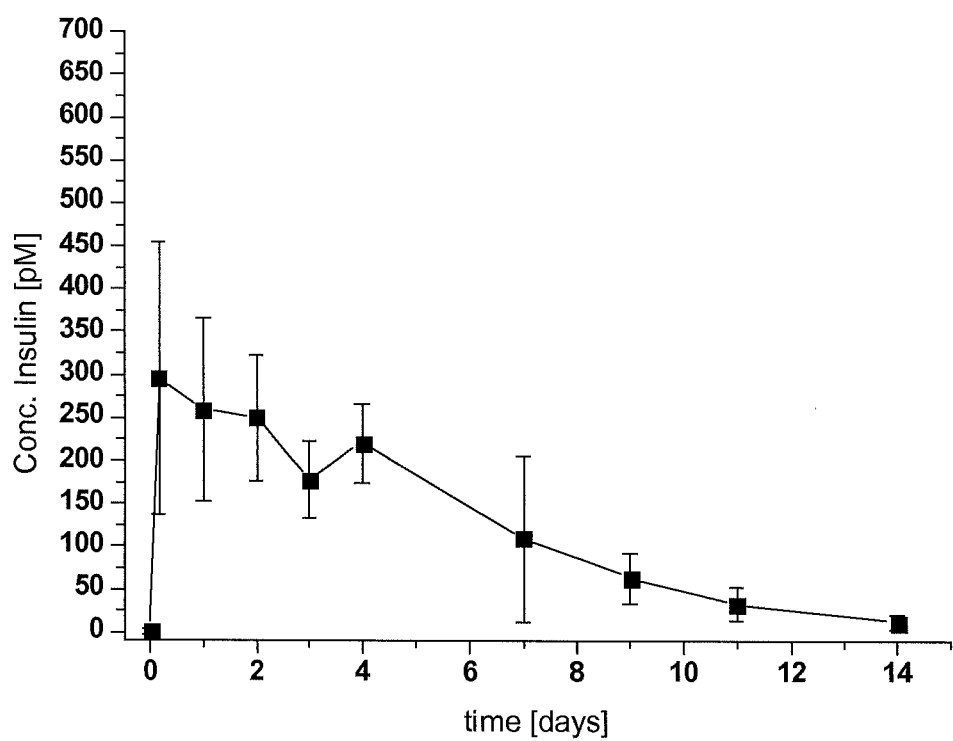
FIG. 2 shows the average plasma insulin concentration of animals 1-10 after a single subcutaneous dose of test item 11a containing 6 mg insulin into healthy rats over a 2 week period. (Error bars are given as ±standard deviation as derived from all 10 animals, $t_0$ values were taken 3 days before dosage.)

One group consisting of 10 male Wistar rats (200-250 g) was used to study the plasma insulin levels over a period of 14 days. Each of the animals received a single subcutaneous injection of 500 µL 11a suspension in acetate buffer pH 5, containing 6 mg insulin (12 mg insulin/ml). Per animal and time point 200 µL of blood was withdrawn sublingually to obtain 100 µL Li-Heparin plasma. Samples were collected before application and after 4 h, 1, 2, 3, 4, 7, 9, 11 and 14 days post injection. Plasma samples were frozen within 15 min after blood withdrawal and stored at −80° C. until assayed. Plasma insulin concentrations were measured using an ultrasensitive Insulin ELISA kit (Mercodia) by following the manufacturer's protocol. Plasma samples were diluted in ELISA buffer (1:5 and 1:10 with calibrator 0) prior to measurement. Insulin concentrations were calculated from a calibration curve which was generated by measuring insulin standards in duplicate and fitting the values using linear regression. The insulin concentration was defined as the mean from two independent dilution series corrected by the respective dilution factor and plotted against time. Averaged plasma insulin concentrations for each time point were obtained by calculating the mean of all animals used as shown in FIG. 2.

A burstless and sustained release of insulin over 14 days was observed.

Example 15

Pharmacokinetics Study in Rat

The pharmacokinetics of 11da were determined by measuring plasma insulin concentrations over a period of 13 days in healthy rats.

Figure 3:
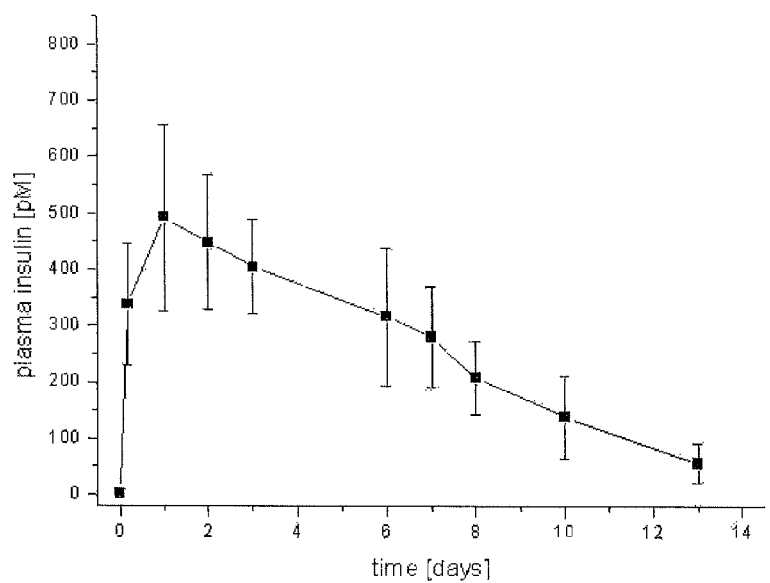
FIG. 3: Average plasma insulin concentration of animals 1-8 after a single subcutaneous dose of test item 11da containing 3 mg insulin into healthy rats over a period of 13 days. (Error bars are given as ±standard deviation as derived from all 8 animals, $t_0$ values were taken 1 day before dosage.)

8 Wistar rats (appr. 250 g body weight) received a single subcutaneous injection of 500 µL of test item 11da in acetate buffer pH 5, containing 3 mg insulin (approx. 12 mg/kg). Per animal and time point 200 µL of blood was withdrawn from the tail vein to obtain about 100 µL Li-Heparin plasma. Samples were collected 1 day before and 4h, 1d, 2d, 3d, 6d, 7d, 8d, 10d and 13d after test item administration. Plasma samples were frozen and stored at −80° C. until assayed. The insulin content of the plasma samples was measured using a human insulin ultrasensitive ELISA Kit (DRG Instruments GmbH, Germany) following the manufacturer's instructions. Blanks (calibrator 0) were included in the calibration curve and were subtracted from the sample values and the calibration curve was fitted using a 3rd order polynomic equation. Before analysis plasma samples were vortexed and diluted in reaction tubes (1:5 and 1:10 with calibrator 0). For analysis OD at 450 nm was measured with a microtiter plate reader (Tecan Ultra) without reference wavelength correction. Results of plasma insulin content up to day 13 for all animals being investigated are shown in FIG. 3.

After a single subcutaneous injection of 500 µL 11d that contained 3 mg insulin the average plasma insulin level rose to a maximum of about 500 pM on day 1. As expected the plasma insulin concentration subsequently decreased continuously within 2 weeks. The peak to trough ratio of plasma insulin levels within the first week of the study was approximately 1.7

Example 16

Pharmacokinetics and Pharmacodynamics Study in Rats

The amount and the bioactivity of the released insulin was investigated by analyzing the plasma insulin concentration and the blood glucose lowering effect in an exploratory pharmacokinetic/pharmacodynamic study using diabetic Sprague-Dawley (SD) rats.

Figure 4:
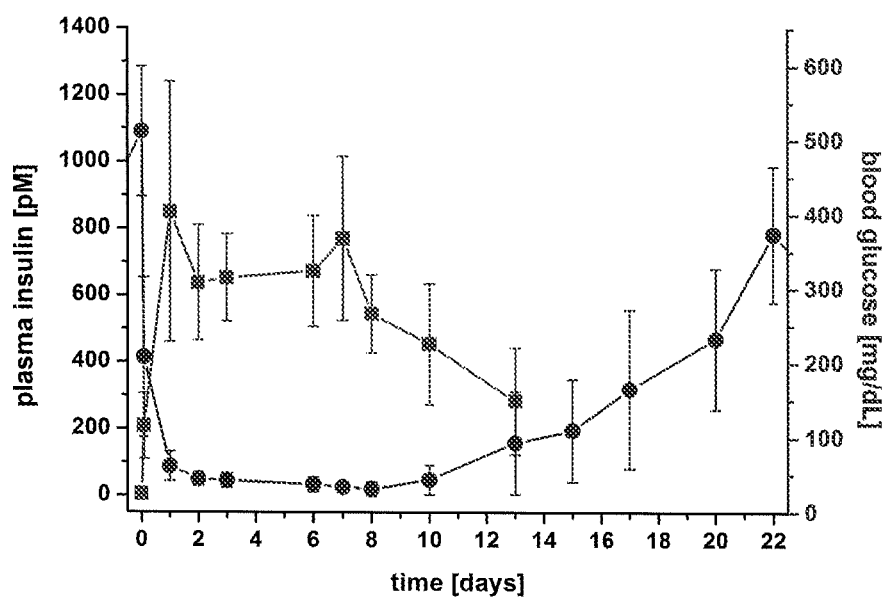
FIG. 4: Plasma insulin concentration (squares) and blood glucose level (circles) after a single subcutaneous dose of test item 11da containing 6.4 mg insulin into diabetic rats (n=7). (Error bars are given as ±standard deviation as derived from all 7 animals, $t_0$ values were taken 4 days before dosage.)

For this purpose diabetes was induced in 8 rats with streptozotocin (STZ) and all animals with blood glucose levels above 350 mg/dL on day 0 were included in this study. 7 out of 8 SD rats became diabetic and received a single subcutaneous injection of 500 µL test item 11da in acetate buffer pH 5, containing 6.4 mg insulin. Per animal and time point 200 µL of blood was withdrawn from the tail vein to obtain about 100 µL Li-Heparin plasma. Samples were collected 4 days before and 2h, 1d, 2d, 3d, 6d, 7d, 8d, 10d and 13d after test item administration. Plasma samples were frozen and stored at −80° C. until assayed. Blood glucose was measured with an AccuChek Comfort device from the tail vein 3 times before injection and 2h, 1d, 2d, 3d, 6d, 7d, 8d, 10d, 13d, 15d, 17d, 20d, 22d and 24d after test item administration. The insulin content of the plasma samples was measured using a human insulin ELISA Kit (DRG Instruments GmbH, Germany) following the manufacturer's instructions. Blanks (calibrator 0) were included in the calibration curve and were subtracted from the sample values and the calibration curve was fitted using a 3rd order polynomic equation. Before analysis plasma samples were vortexed and diluted in reaction tubes (1:5 and 1:10 with calibrator 0). For analysis OD at 450 nm was measured with a microtiter plate reader (Tecan Ultra) without reference wavelength correction. The plasma insulin level was monitored over 2 weeks and blood glucose level over a 3 week period as shown in FIG. 4.

After a single subcutaneous injection of insulin hydrogel 11da the blood glucose level was effectively lowered over a period of 10 days with values below 100 mg/dL without any symptoms for hypoglycemia. Due to the higher dosage of 6.4 mg insulin per animal, the maximal plasma insulin concentration was approx. 800 pM on day 1 and decreased continuously within 2 weeks to approx. 300 pM. Simultaneously the blood glucose values began to rise after 10 days and reached predose levels after 3 weeks.

Example 17

Pharmacokinetics Study Over 24 Hours (Burst Study) in Rats

In order to prove that insulin is released from insulin-linker-hydrogel without a burst the plasma insulin concentration was monitored over a period of 24 hours in healthy rats.

Figure 5:
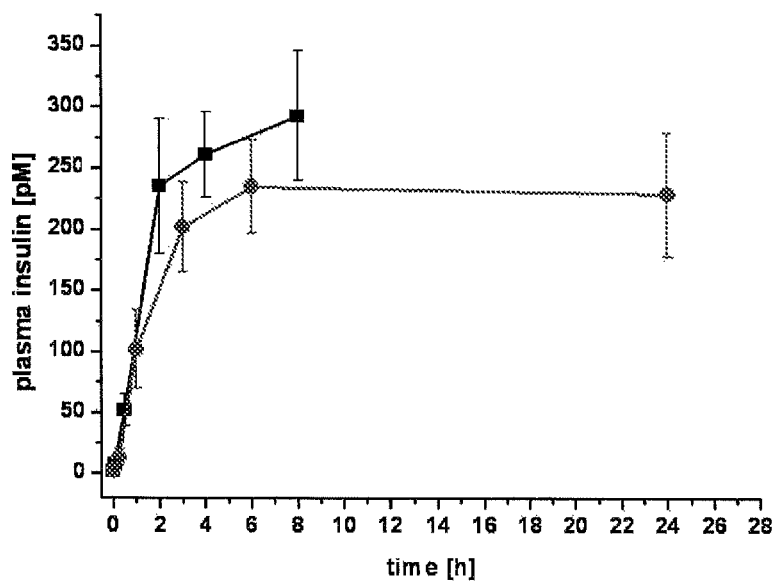
FIG. 5: Average plasma insulin level after a single subcutaneous dose of 8 mg/kg of test item 11db into healthy rats during the first 24 hours after dosage (burst analysis). 8 rats were divided into 2 groups and blood samples for pharmacokinetics were taken alternating between both groups. In neither group was a burst effect perceivable. (Error bars are given as ±standard deviation as derived from all animals per group, $t_0$ values were taken 1 day before dosage.)

8 Sprague-Dawley rats (200-250 g body weight) were divided into 2 groups and received a single subcutaneous injection of 2 mL of test item 11db in acetate buffer pH 5 per kg body weight. The test item had a concentration of 4 mg/mL insulin so that each animal received 8 mg insulin per kg body weight. Per animal and time point 200 µL of blood was withdrawn from the tail vein to obtain about 100 µL Li-Heparin plasma. Group A samples were collected predose and 5 min, 30 min, 2 h, 4 h and 8 h after application of test item and for group B predose and 15 min, 1 h, 3 h, 6 h and 24 h after test item administration. Plasma samples were frozen and stored at −80° C. until assayed. The insulin content of the plasma samples was measured using a human insulin ultrasensitive ELISA Kit (DRG Instruments GmbH, Germany) following the manufacturer's instructions. Blanks (calibrator 0) were included in the calibration curve and were subtracted from the sample values and the calibration curve was fitted using a 3rd order polynomic equation. Before analysis plasma samples were vortexed and diluted in reaction tubes (1:5 and 1:10 with calibrator 0). For analysis OD at 450 nm was measured with a microtiter plate reader (Tecan Ultra) without reference wavelength correction. The result is shown in FIG. 5 and clearly indicates that insulin is released without any burst.

Example 18

Pharmacokinetics and Pharmacodynamics Multiple Dose Study in Rats

The pharmacokinetics and pharmacodynamics after 3 weekly doses of 11da were determined by measuring plasma insulin concentrations and blood glucose levels over a period of 4 weeks in diabetic rats.

Figure 6:
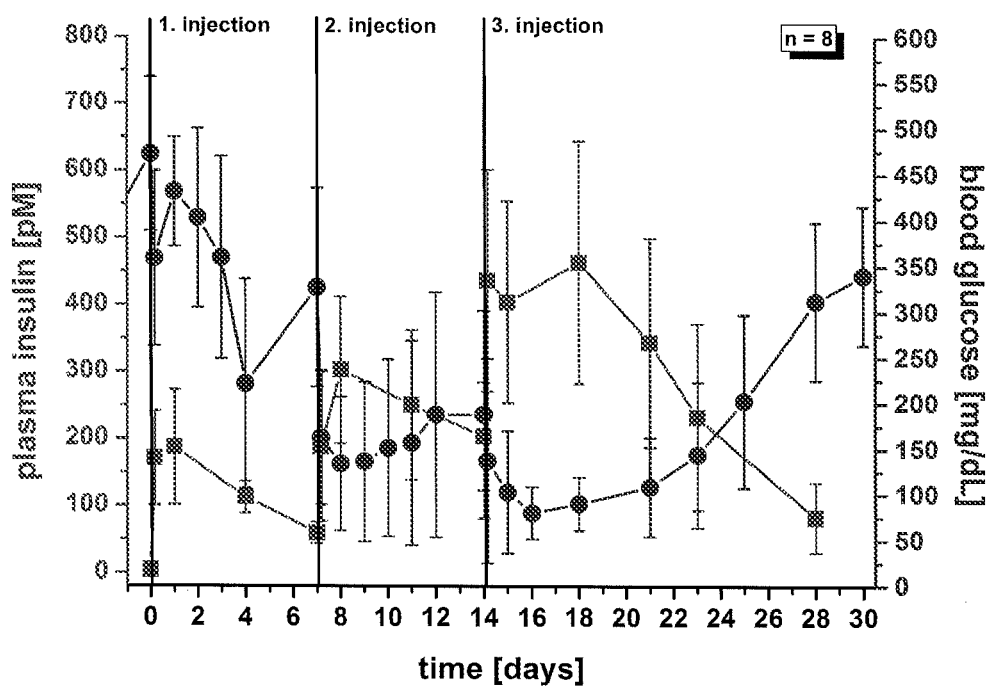
FIG. 6: Plasma insulin concentration (squares) and blood glucose level (circles) during a 4 week period after 3 weekly subcutaneous doses of 8 mg/kg of test item 11da into diabetic rats (n=8). (error bars are given as ±standard deviation as derived from all 8 animals, $t_0$ values were taken 3 days before dosage.)

8 Sprague-Dawley rats were used with a mean body weight of 239 g. Diabetes was induced with streptozotocin (STZ) and all animals with blood glucose levels above 350 mg/dL on day 0 (test item injection day) were included in the study. 8 of 8 animals which received STZ treatment became diabetic and received 3 weekly subcutaneous injections on day 0, 7 and 14 of 2 mL test item 11da in acetate buffer pH 5 per kg body weight. With a test item insulin concentration of 4 mg/mL the applied dose was 8 mg insulin per kg body weight. Per animal and time point 200 µl of blood was withdrawn from the tail vein to obtain about 100 µL Li-Heparin plasma. Samples were collected 3 days before and up to 28 days after test item administration. Plasma samples were frozen and stored at −80° C. until assayed. Blood glucose was measured with an AccuChek Comfort device from the tail vein 3 times before injection and up to 30 days post injection. The insulin content of the plasma samples was measured using a human insulin ELISA Kit (DRG Instruments GmbH, Germany) following the manufacturer's instructions. Blanks (calibrator 0) were included in the calibration curve and were subtracted from the sample values and the calibration curve was fitted using a 3rd order polynomic equation. Before analysis plasma samples were vortexed and diluted in reaction tubes (1:5 and 1:10 with calibrator 0). For analysis OD at 450 nm was measured with a microtiter plate reader (Tecan Ultra) without reference wavelength correction. The plasma insulin level and the blood glucose level were monitored over a 4 week period and are both shown in FIG. 6.

The shape of the curves indicate that the released insulin was bioactive by steadily lowering the blood glucose level to values about 100 mg/dL post 3rd injection which remained low for about a week. At the same time the maximal insulin concentration increased steadily starting from 200 pM after the first and 300 pM after the second dose to 400 pM following the third dose and subsequently decreased again within 2 weeks to values below 100 pM.

Example 19

Pharmacokinetics Study in Rat

The pharmacokinetics of 11dc were determined by measuring plasma insulin concentrations over a period of 13 days in healthy rats.

Figure 7:
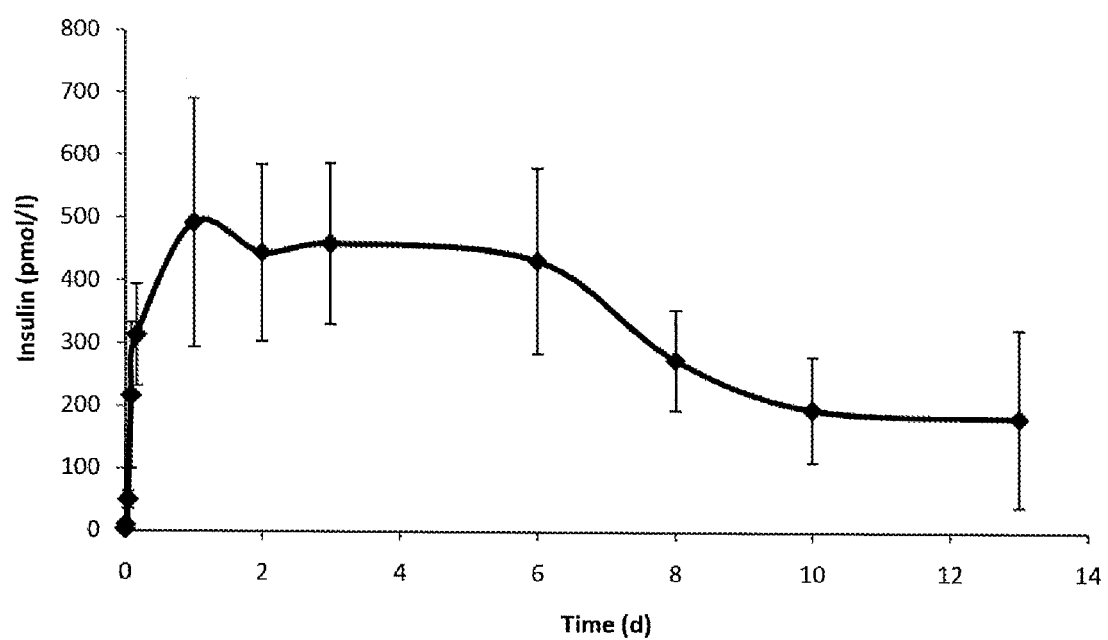
FIG. 7: Average plasma insulin concentration of animals 1-8 (animals 1-4 and animals 5-8 for 0.3, 1h, 2, and 4h value, respectively) after a single subcutaneous injection of 12 mg/kg insulin formulated in test item 11dc into healthy rats over a period of 13 days. (Error bars are given as +/−standard deviation as derived from all 8 animals, $t_0$ values were taken 4 days before dosage.)

8 Wistar rats (appr. 230 g body weight) received a single subcutaneous injection of 2 ml/kg of test item 11dc in succinate buffer pH 5 (10 mM succinate/tris, 85 g/l trehalose, 0.01% Tween-20, pH 5.0), containing 3 mg insulin (12 mg/kg dose). Per animal and time point 200 µL of blood was withdrawn from the tail vein to obtain about 100 µL Li-Heparin plasma. Samples were collected 4 days before and 0.3 h (4 animals), 1 h (4 animals), 2 h (4 animals), 4 h (4 animals), 1d, 2d, 3d, 6d, 8d, 10d and 13d after test item administration. Plasma samples were frozen and stored at −80° C. until assayed. The insulin content of the plasma samples was measured using a human insulin ultrasensitive ELISA Kit (DRG Instruments GmbH, Germany) following the manufacturer's instructions. Blanks (calibrator 0) were included in the calibration curve and were subtracted from the sample values and the calibration curve was fitted using a 3rd order polynomic equation. Before analysis plasma samples were vortexed and diluted in reaction tubes (1:5 and 1:10 with calibrator 0). For analysis OD at 450 nm was measured with a microtiter plate reader (Tecan Ultra) without reference wavelength correction. Results of plasma insulin content up to day 13 for all animals being investigated are shown in FIG. 7.

After a single subcutaneous injection of 12 mg/kg 11dc the average plasma insulin level rose to a maximum of about 500 pM on day 1. As expected the plasma insulin concentration subsequently decreased continuously within 2 weeks. The peak to trough ratio of plasma insulin within the first week was approximately 1.4.

Example 20

Real-Time Insulin Release and Hydrogel Degradation at pH 7.4

Insulin-linker hydrogel 11a (730 µL, containing 3.19 mg insulin) in pH 5.0 acetate buffer (10 mM, 130 mM NaCl, 0.01% (w/v) tween-20) was filled in a sample preparation tube, washed 3× with pH 7.4 release buffer (60 mM sodium phosphate, 3 mM EDTA, 0.01% (w/v) Tween-20) and filled-up to 1.00 mL. An Aliquot of the suspension (0.5 mL, 1.59 mg insulin) was filled in a chromatography column and placed in a temperature controlled incubator (37° C.). Release buffer (pH 7.4) was pumped through the column with a constant flow of 0.25 mL/h (nominal) and collected outside the incubator. At defined time points the solution was analyzed by RP-HPLC (215 nm). The amount of released insulin was plotted against incubation time and curve-fitting software was applied to estimate the corresponding halftime of release. A halftime of 9.4 d for the insulin release was determined.

Figure 8:
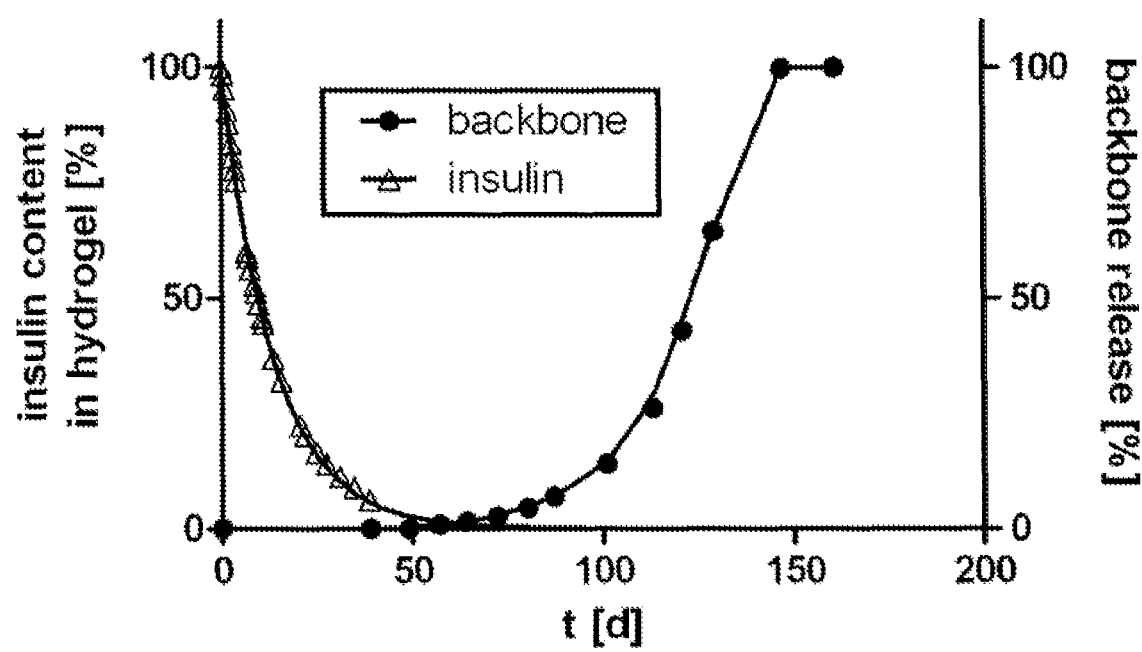
FIG. 8: Overlay of insulin release and hydrogel degradation of insulin-linker-hydrogel 11a. Amount of insulin content in insulin-linker-hydrogel (triangles) and backbone moieties release (circles) upon incubation of insulin-linker-hydrogel at pH 7.4 and 37° C. is plotted against incubation time.

After 39 d incubation at 37° C. the hydrogel suspension was transferred to a sample preparation tube, residual hydrogel was washed out of the column with pH 7.4 release buffer and the sample was filled-up to 1.00 mL. Two aliquots (300 µL each) were transferred to sterile sample preparation tubes, filled-up to 1.5 mL, and incubated at 37° C. Samples were taken at time intervals and analyzed by size exclusion chromatography. UV-signals corresponding to hydrogel released water-soluble degradation products comprising one or more backbone moieties (corresponding to reactive functional groups) were integrated and plotted against incubation time, see FIG. 8.

Example 21

Figure 9:
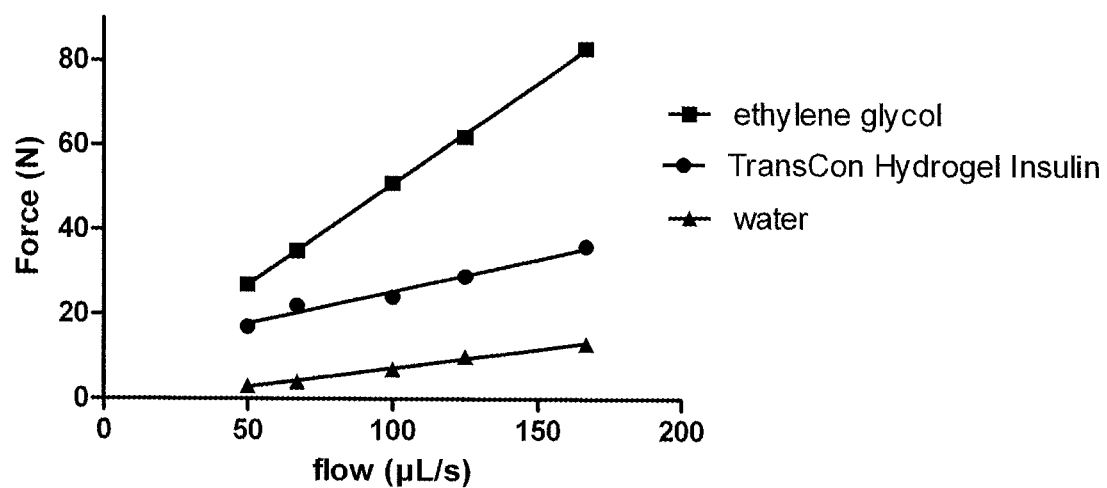
FIG. 9 shows a graph plotting force versus flow using a 30 G needle. Data points: squares=ethylene glycol; triangles=water; dots=hydrogel insulin prodrug.

Injectability of Insulin-Linker-Hydrogel Prodrug 5 mL insulin-linker-hydrogel prodrug 11dc (bead size distribution from 32-75 µm, 18 mg insulin/mil) in pH 5.0 succinic acid/tris (10 mM, 40 g/L mannitol; 10 g/L trehalose dihydrate; 0.05% TWEEN-20) was used. The insulin-linker-hydrogel prodrug suspension was filled into a 1 mL syringe (length 57 mm) via a 20 G needle. The 20 G needle was replaced by a 30 G needle and placed into the syringe mounting (Aqua Computer GmbH&Co. KG) and the measurement was started with a piston velocity of 172 mm/min (equals 50 µL/s) (Force test stand: Multitest 1-d, Data recording software: EvaluatEmperor Lite, Version 1.16-015, Forge Gauge: BFG 200 N (all Mecmesin Ltd., UK). Experiments with increasing piston velocities shown in the table below were carried out with a new insulin-linker-hydrogel prodrug sample. The experiments with water and ethylene glycol were carried out accordingly. For all of the experiments the same 30 G needle was used. Force versus flow using a 30 G needle is shown in FIG. 9.

| Flow/ (sec/mL) | Flow/ (µL/sec) | Velocity of piston/ (mm/min) | Force/N (water) | Force/N 11dc | Force/N (ethylene glycol) |
|---|---|---|---|---|---|
| 6 | 167 | 573 | 13 | 36 | 83 |
| 8 | 125 | 430 | 10 | 29 | 62 |
| 10 | 100 | 344 | 7 | 24 | 51 |
| 15 | 67 | 229 | 4 | 22 | 35 |
| 20 | 50 | 172 | 3 | 17 | 27 |

ABBREVIATIONS

AcOH acetic acid
AcOEt ethyl acetate
Aib 2-Aminoisobutyric acid
Bn benzyl
Boc t-butyloxycarbonyl
COMU (1-Cyano-2-ethoxy-2-oxoethylidenaminooxy)dimethylamino-morpholino-carbenium hexafluorophosphate
DBU 1,3-diazabicyclo[5.4.0]undecene
DCC N,N,-dicyclohexylcarbodiimid
DCM dichloromethane
DIEA diisopropylethylamine
DMAP dimethylamino-pyridine
DMF N,N-dimethylformamide
Dmob 2,4-dimethoxybenzyl
DMSO dimethylsulfoxide
EDC 1-Ethyl-3-(3-dimethylaminopropyl)carbodiimid
EDTA ethylenediaminetetraacetic acid
eq stoichiometric equivalent
ESI-MS electrospray ionization mass spectrometry
EtOH ethanol
Fmoc 9-fluorenylmethoxycarbonyl
HATU O-(7-Azabenzotriazol-1-yl)-N,N,N',N'-tetramethyluronium hexafluorophosphate
HFIP hexafluoroisopropanol
HPLC high performance liquid chromatography
HOBt N-hydroxybenzotriazole
iPrOH 2-propanol
LCMS mass spectrometry-coupled liquid chromatography
Mal 3-maleimido propyl
Mal-PEG6-NHS N-(3-maleimidopropyl)-21-amino-4,7,10,13,16,19-hexaoxa-heneicosanoic acid NHS ester
Me methyl
MeCN acetonitrile
MeOH methanol
Mmt 4-methoxytrityl
MS mass spectrum/mass spectrometry
MTBE methyl tert.-butyl ether
MW molecular mass
n.d. not determined
NHS N-hydroxy succinimide
OD optical density
OBu butyloxy
OtBu tert.-butyloxy
PEG poly(ethylene glycol)
Phth phthal-
PyBOP benzotriazole-1-yl-oxy-tris-pyrrolidino-phosphonium hexafluorophosphate
RP-HPLC reversed-phase high performance liquid chromatography
rpm rounds per minute RT room temperature
SEC size exclusion chromatography
Su succinimidyl
TCP 2-chlorotrityl chloride resin
TES triethylsilane
TFA trifluoroacetic acid
THF tetrahydrofurane
TMEDA N,N,N'N'-tetramethylethylene diamine
Tmob 2,4,6-trimethoxybenzyl
Trt triphenylmethyl, trityl
UPLC ultra performance liquid chromatography
UV ultraviolet
VIS visual

The invention claimed is:

1. A prodrug comprising:
a hydrogel (Z) with backbone moieties of formula C-(A-Hyp)$_4$, wherein:
each A is independently selected from the formula —(CH$_2$)$_{n1}$(OCH$_2$CH$_2$)$_n$X'—,
wherein:
n1 is 1 or 2;
n is an integer ranging from 5 to 50; and
X' is an amide linkage linking A and Hyp;
each Hyp is independently selected from hyperbranched polypeptides comprising lysine;
the backbone moieties are crosslinked by poly(ethylene glycol)-based crosslinker moieties, comprising m ethylene glycol units, wherein m is an integer ranging from 3-100, and terminated by at least two hydrolytically degradable bonds;
a linker $L^2$ connected to a backbone moiety, wherein:
$L^2$ is a single chemical bond or is a C$_{1-20}$ alkyl chain, which is optionally interrupted by one or more groups independently selected from —O— and C(O)N(R$^{3aa}$) and is optionally substituted with one or more groups independently selected from OH and C(O)N(R$^{3aa}$R$^{3aaa}$), wherein R$^{3aa}$ and R$^{3aaa}$ are independently selected from the group consisting of H and C$_{1-4}$ alkyl; and
$L^2$ is attached to Z via a terminal group selected from the group consisting of

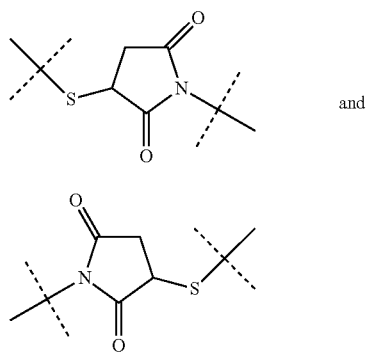

wherein $L^2$ is attached to the sulfur atom in structure X and Z is attached to the nitrogen atom in structure X or $L^2$ is attached to the nitrogen atom in structure XI and Z is attached to the sulfur atom in structure XI; and
an insulin-linker conjugate D-$L^1$, wherein:
D is insulin; and $L^1$ is:

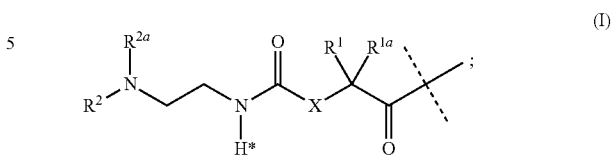

wherein:
the dashed line indicates the point of attachment of $L^1$ to one of the amino groups of insulin through an amide bond;
X is C(R$^3$R$^{3a}$);
R$^{1a}$ and R$^{3a}$ are independently selected from the group consisting of H, NH(R$^{2b}$), N(R$^{2b}$)C(O)R$^4$ and C$_{1-4}$ alkyl and optionally substituted with $L^2$-Z;
R$^1$, R$^2$, R$^{2a}$, R$^{2b}$, R$^3$, and R$^4$ are independently selected from the group consisting of H and C$_{1-4}$ alkyl, and optionally substituted with $L^2$-Z; and
$L^1$ is substituted with one $L^2$-Z provided that the hydrogen marked with the asterisk in formula (I) is not replaced;
or a pharmaceutically acceptable salt thereof, wherein said prodrug is in the form of microparticles.

2. The prodrug of claim 1, wherein in formula (I) R$^2$ is replaced by $L^2$-Z.

3. The prodrug of claim 1, wherein in formula (I) R$^1$ is replaced by $L^2$-Z.

4. The prodrug of claim 1, wherein R$^{3a}$ is N(R$^{2b}$)C(O)R$^4$.

5. The prodrug of claim 1, wherein R$^{3a}$ is $L^2$-Z.

6. The prodrug of claim 1, wherein R$^{3a}$ is N(R$^{2b}$)-$L^2$-Z.

7. The prodrug of claim 1, wherein the insulin is attached to $L^1$ through the nitrogen N$^{\alpha A1}$.

8. The prodrug of claim 1, wherein the insulin is recombinant human insulin.

9. The prodrug of claim 8, wherein the recombinant human insulin is attached to $L^1$ through the nitrogen of a lysine side chain of the insulin.

10. The prodrug of claim 1, wherein the crosslinker moieties have a molecular weight in the range of from 0.5 kDa to 5 kDa.

11. The prodrug of claim 1, wherein $L^2$ is attached to Z via a terminal group having the structure:

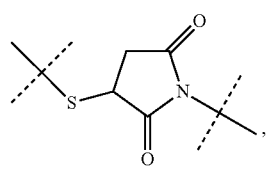

wherein the dashed lines indicate the attachment to $L^2$ and Z, respectively.

12. The prodrug of claim 1, of formula (IIa):

(IIa)

wherein $N^\epsilon$-Insulin refers to insulin connected via one lysine side chain.

13. The prodrug of claim 1, wherein the backbone moieties comprise a branching core of the following formula:

wherein the dashed line indicates attachment to the remainder of the backbone moiety.

14. The prodrug of claim 1, wherein the backbone moieties comprise a structure of the following formula:

C—[(CH$_2$)$_{n1}$(OCH$_2$CH$_2$)$_n$—N]$_4$— wherein n is an integer ranging from 5 to 50, n1 is 1, and the dashed line indicates attachment to the rest of the molecule.

15. The prodrug of claim 1, wherein the backbone moieties comprises a hyperbranched moiety Hyp of the following formula:

-continued wherein the dashed lines indicate attachment to the rest of the molecule and carbon atoms marked with asterisks indicate S-configuration.

16. The prodrug of claim 1, wherein the backbone moieties are attached to at least one spacer of the following formula:

wherein one of the dashed lines indicates attachment to the hyperbranched moiety Hyp and the second dashed line indicates attachment to the rest of the molecule; and wherein m' is an integer ranging from 2 to 4.

17. The prodrug of claim 1, wherein the backbone moieties are attached to at least one spacer of the following formula:

wherein the dashed line marked with the asterisk indicates the bond between the hydrogel and the nitrogen of the thiosuccinimide group of structure X, wherein the other dashed line indicates attachment to Hyp, and wherein p is an integer ranging from 0 to 10.

18. The prodrug of claim 16, wherein the poly(ethylene glycol)-based crosslinker moieties are symmetrically connected through ester bonds to two alpha, omega-aliphatic dicarboxylic acid spacers.

19. The prodrug of claim 1, wherein the microparticles have a diameter ranging from 1 to 500 μm.

20. An insulin-linker conjugate of formula (IIIa)

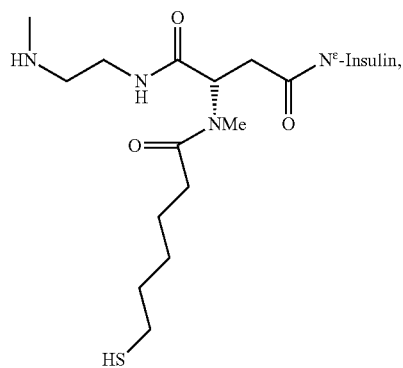

wherein $N^\epsilon$-Insulin refers to insulin connected via one lysine side chain.

21. A pharmaceutical composition comprising a prodrug of claim 1 or a pharmaceutically acceptable salt thereof together with a pharmaceutically acceptable excipient.

22. A dry pharmaceutical composition according to claim 21.

23. A lyophilized pharmaceutical composition according to claim 22.

24. A single dose pharmaceutical composition according to any one of claims 21 to 23.

25. The pharmaceutical composition of claim 21, comprising one or more additional biologically active agents.

26. A suspension comprising the pharmaceutical composition according to claim 21 or 25.

27. A method of treating a disease or disorder chosen from the group consisting of hyperglycemia, pre-diabetes, impaired glucose tolerance, diabetes type I, and diabetes type II, comprising administering to a patient in need thereof a prodrug according to claim 1, thereby treating the disease or disorder.

* * * * *

UNITED STATES PATENT AND TRADEMARK OFFICE
CERTIFICATE OF CORRECTION

PATENT NO. : 9,138,462 B2
APPLICATION NO. : 13/387940
DATED : September 22, 2015
INVENTOR(S) : Harald Rau et al.

It is certified that error appears in the above-identified patent and that said Letters Patent is hereby corrected as shown below:

On the Title page of the Patent:

Page 1, right-hand side column, section "OTHER PUBLICATIONS", line 1-3: please replace "Muller, Prodrug Approaches for Enhancing the Bioavailability of Drugs eith Low Solubility, Chemistry & Biodiversity, 2009, 6, pp. 2071-2083.*" with --Muller, Prodrug Approaches for Enhancing the Bioavailability of Drugs with Low Solubility, Chemistry & Biodiversity, 2009, 6, pp. 2071-2083.*--;

Page 2, right-hand side column, section "OTHER PUBLICATIONS", lines 20-23: please replace "Izutsu, Stabilization of Therapeutic Proteins by Chemica I and Physica I Methods, from Therapeutic proteins, methods and protocols, Edited by C. Mark Smales and David C. James, Humana press, 2005, pp. 1-8.*" with --"Izutsu, Stabilization of Therapeutic Proteins by Chemical and Physical Methods, from Therapeutic proteins, methods and protocols, Edited by C. Mark Smales and David C. James, Humana press, 2005, pp. 1-8.*"--;

Page 2, right-hand side column, section "OTHER PUBLICATIONS", lines 34-36: please replace ""Beaumont et al., Design of Ester Prodrugs to Enhance Oral Absorption of Poorly Permeable Compounds: Challenges to theDiscovery Scientist, Current Drug Metabolism, 2003, 4, 461-485."" with --"Beaumont et al., Design of Ester Prodrugs to Enhance Oral Absorption of Poorly Permeable Compounds: Challenges to the Discovery Scientist, Current Drug Metabolism, 2003, 4, 461-485."--;

Signed and Sealed this
Twenty-first Day of June, 2016

Michelle K. Lee
*Director of the United States Patent and Trademark Office*

CERTIFICATE OF CORRECTION (continued)
U.S. Pat. No. 9,138,462 B2

Page 3, left-hand side column, section "OTHER PUBLICATIONS", line 11: please add --Definition of mimetics, from http://www.thefreedictionary.com/p/mimetic, pp. 1-2, accessed Oct. 11, 2013.
Definition of moiety, from http://dictionary.reference.com/browse/moieties, pp. 1-3, accessed Aug. 26, 2010.--;

Page 3, left-hand side column, section "OTHER PUBLICATIONS", lines 25-26: please replace "Ellman et al., "A new and rapid colorimetric determinationof acetylcholinesterase activity." Biochem. Pharmacol., 1961, 7, 88-95." with --Ellman et al., "A new and rapid colorimetric determination of acetylcholinesterase activity," Biochem. Pharmacol., 1961, 7, 88-95.--;

Page 3, left-hand side column, section "OTHER PUBLICATIONS", lines 40-43: please replace "Goke et al., "Exendin-4 Is a High Potency Agonist and Truncated Exendin-(9-39)-amide an Antagonist at the Glucagon-like Peptide 1-(7-36)-amide Receptor ofInsulin-secreting B-Cells", J. of Biolo. Chern., Sep. 15, 1993, pp. 19650-19655, vol. 268, No. 26, US." with --Goke et al., "Exendin-4 Is a High Potency Agonist and Truncated Exendin-(9-39)-amide an Antagonist at the Glucagon-like Peptide 1-(7-36)-amide Receptor of Insulin-secreting B-Cells", J. of Biolo. Chem., Sep. 15, 1993, pp. 19650-19655, vol. 268, No. 26, US.--;

Page 3, left-hand side column, section "OTHER PUBLICATIONS", lines 46-48: please replace "Grayson et al., "Convergent Dendrons and Dendrimers: from Synthesis to Applications", Chern. Rev., 2001, pp. 3819-3867, vol. 101, Berkeley, CA, US." with --Grayson et al., "Convergent Dendrons and Dendrimers: from Synthesis to Applications", Chem. Rev., 2001, pp. 3819-3867, vol. 101, Berkeley, CA, US.--;

Page 3, left-hand side column, section "OTHER PUBLICATIONS", lines 57-60: please replace "Greenwald et al., "Drug Delivery Systems Employing 1,4- or 1,6-Eiimination: Poly( ethylene glycol) Prodrugs of Amine-Containing Compounds", "J. Med. Chem.", 1999, pp. 3657-3667, vol. 42, Publisher: American Chemical Society." with --Greenwald et al., "Drug Delivery Systems Employing 1,4- or 1,6-Elimination: Poly(ethylene glycol) Prodrugs of Amine-Containing Compounds", "J. Med. Chem.", 1999, pp. 3657-3667, vol. 42, Publisher: American Chemical Society.--;

CERTIFICATE OF CORRECTION (continued)
U.S. Pat. No. 9,138,462 B2

Page 3, right-hand side column, section "OTHER PUBLICATIONS", lines 1-3: please replace "Gutniak et al., "Antidiabetogenic effect of glucagon-like peptide-! (7-36)amide in normal subjects and patients with diabetes mellitus", NE J. of Med., May 14, 1992, pp. 1316-1322, vol. 326, No. 20." with --Gutniak et al., "Antidiabetogenic effect of glucagon-like peptide-1 (7-36)amide in normal subjects and patients with diabetes mellitus", NE J. of Med., May 14, 1992, pp. 1316-1322, vol. 326, No. 20.--;

Page 3, right-hand side column, section "OTHER PUBLICATIONS", line 22: please add --Human insulin amino acid sequence, from http://dailymed.nlm.nih.gov/dailymed/fda/fdaDrugXsl.cfm?id~7043, p. 1, accessed Oct. 16, 2013.--;

Page 3, right-hand side column, section "OTHER PUBLICATIONS", lines 28-31: please replace "Young et al., "Glucose-Lowering and Insulin-Sensitizing Actions ofExendin-4: Studies in Obese Diabetic (ob/ob, db/db) Mice, Diabetic Fatty Zucker Rats, and Diabetic Rhesus Monkeys (Macaca mulatta)", Diabetes, May 1999, pp. 1026-1034, vol. 48." with --Young et al., "Glucose-Lowering and Insulin-Sensitizing Actions of Exendin-4: Studies in Obese Diabetic (ob/ob, db/db) Mice, Diabetic Fatty Zucker Rats, and Diabetic Rhesus Monkeys (Macaca mulatta)", Diabetes, May 1999, pp. 1026-1034, vol. 48.--;

Page 3, right-hand side column, section "OTHER PUBLICATIONS", line 50: please add --Diabetes Mellitus, from Merck Manual, pp. 1-22, accessed Apr. 2, 2013.--;

Page 3, right-hand side column, section "OTHER PUBLICATIONS", lines 52-54: please replace "Wathier et al., Dendritic macromers as in situ polymerizing biomaterials for securing , J. Am. Chem. Soc., 2004 vol. 126, pp. 12744-12746." with --Wathier et al., Dendritic macromers as in situ polymerizing biomaterials for securing cataract incisions , J. Am. Chem. Soc., 2004 vol. 126, pp. 12744-12745.--;

Page 3, right-hand side column, section "OTHER PUBLICATIONS", lines 63-69: please replace "Kanjickal et al., "Effects of sterilization on poly( ethylene glycol) hydrogels", J. Biomed. Mater. Res. Part A., Jan. 9, 2008, pp. 608-617, Wiley InterSciencc (www.interscience.wiley.com). Kim et al., "Effects of Once-Weekly Dosing of a Long-Acting Release Formulation ofExenatide on Glucose Control and Body Weight in Subjects With Type 2 Diabetes", Diabetes Care, Jun. 2007, pp.

CERTIFICATE OF CORRECTION (continued)
U.S. Pat. No. 9,138,462 B2 hydrogels", J. Biomed. Mater. Res. Part A., Jan. 9, 2008, pp. 608-617, Wiley InterScience (www.interscience.wiley.com).
Kim et al., "Effects of Once-Weekly Dosing of a Long-Acting Release Formulation of Exenatide on Glucose Control and Body Weight in Subjects With Type 2 Diabetes", Diabetes Care, Jun. 2007, pp. 1487-1493, vol. 30, No. 6.--;

Page 4, left-hand side column, section "OTHER PUBLICATIONS", lines 20-23: please replace "Minkov et al., "Structural Studies of Radiation-corsslinked Polyethylene oxide)", J. Polymer Sci: Part B: Polymer Phys., 1989, pp. 621-642, vol. 27, John Wiley & Sons, Inc., Hoboken, NJ." with --Minkova et al., "Structural Studies of Radiation-crosslinked Poly(ethylene oxide)", J. Polymer Sci: Part B: Polymer Phys., 1989, pp. 621-642, vol. 27, John Wiley & Sons, Inc., Hoboken, NJ.--;

Page 4, left-hand side column, section "OTHER PUBLICATIONS", lines 66-68: please replace "Shao et al., Stabilization of pH-induced degradationof porcine insulin in biodegradable polyester microspheres, Pharm. Dev. Technol. 4(4):633-642, 1999." with --Shao et al., Stabilization of pH-induced degradation of porcine insulin in biodegradable polyester microspheres, Pharm. Dev. Technol. 4(4):633-642, 1999.--;

Page 4, right-hand side column, section "OTHER PUBLICATIONS", lines 14-17: please replace "Sohma et al., "Development of water-soluble prodrugs of the HIV-1 protease inhibitor KNI-727: Importance of the conversion time for higher gastrointestinal absorption of prodrugs based on spontaneous chemica I cleavage." J. Med. Chem., 46(19):4124-4135, 2003." with --Sohma et al., "Development of water-soluble prodrugs of the HIV-1 protease inhibitor KNI-727: Importance of the conversion time for higher gastrointestinal absorption of prodrugs based on spontaneous chemical cleavage." J. Med. Chem., 46(19):4124-4135, 2003.--;

Page 5, left-hand side column, section "OTHER PUBLICATIONS", lines 13-15: please replace "Belikov, "Fannazevticheskaya Khimiya", M., Vysshaya shoka, 1993, t. I, str. 43-47 (= Phamlaccutical Chemistry, Moscow, High School, 1993, vol. 1 p. 43-47) (article in Russian with English abstract)." with --Belikov, "Fannazevticheskaya Khimiya", M., Vysshaya shoka, 1993, t. I, str. 43-47 (= Pharmaceutical Chemistry, Moscow, High School, 1993, vol. 1 p. 43-47) (article in Russian with English abstract).--; and

CERTIFICATE OF CORRECTION (continued)
U.S. Pat. No. 9,138,462 B2

Page 5, right-hand side column, section "OTHER PUBLICATIONS", lines 20-22: please replace "Nektar, Inc., "Nektar Molecule Engineering- Polyethylene Dlycol and Derivatives for Advanced PEGylation", "Nektar Advanced PEGylation (Catalog 2004)", 2003." with --Nektar, Inc., "Nektar Molecule Engineering- Polyethylene Glycol and Derivatives for Advanced PEGylation", "Nektar Advanced PEGylation (Catalog 2004)", 2003.--.

In the Claims:

At Column 73, claim number 15, line number 46: please replace "comprises" with --comprise--.